United States Patent
Kaufman et al.

(10) Patent No.: US 11,850,241 B1
(45) Date of Patent: Dec. 26, 2023

(54) COMPOSITIONS OF 1-(4-BROMO-5-(1-ETHYL-7-(METHYL-AMINO)-2-OXO-1,2-DIHYDRO-1,6-NAPHTHYRIDIN-3-YL)-2-FLUOROPHEYL)-3-PHENYLUREA

(71) Applicant: Decipher Pharmaceuticals, LLC, Waltham, MA (US)

(72) Inventors: Michael D. Kaufman, Waltham, MA (US); Scott Bone, Bend, OR (US); Corey Bloom, Bend, OR (US); Fred Jordan, Bend, OR (US)

(73) Assignee: Decipher Pharmaceuticals, LLC, Waltham, MA (US)

( * ) Notice: Subject to any disclaimer, the term of this patent is extended or adjusted under 35 U.S.C. 154(b) by 0 days.

(21) Appl. No.: 18/448,333

(22) Filed: Aug. 11, 2023

Related U.S. Application Data

(63) Continuation of application No. 18/178,789, filed on Mar. 6, 2023, which is a continuation of application No. 18/148,766, filed on Dec. 30, 2022, which is a continuation of application No. 17/735,820, filed on May 3, 2022, now Pat. No. 11,612,591, which is a continuation of application No. 17/180,241, filed on Feb. 19, 2021, now Pat. No. 11,395,818, which is a continuation of application No. PCT/US2020/067560, filed on Dec. 30, 2020.

(60) Provisional application No. 62/968,695, filed on Jan. 31, 2020, provisional application No. 62/968,724, filed on Jan. 31, 2020, provisional application No. 62/955,062, filed on Dec. 30, 2019, provisional application No. 62/955,073, filed on Dec. 30, 2019.

(51) Int. Cl.
*A61K 31/4375* (2006.01)
*A61K 47/38* (2006.01)
*A61K 9/00* (2006.01)
*A61K 9/10* (2006.01)

(52) U.S. Cl.
CPC ........ *A61K 31/4375* (2013.01); *A61K 9/0053* (2013.01); *A61K 9/10* (2013.01); *A61K 47/38* (2013.01)

(58) Field of Classification Search
CPC .... A61K 31/4375; A61K 9/0053; A61K 9/10; A61K 47/38
See application file for complete search history.

(56) References Cited

U.S. PATENT DOCUMENTS

| | | | |
|---|---|---|---|
| 3,528,980 A | 9/1970 | Islip | |
| 3,818,024 A | 6/1974 | Krenzer | |
| 3,939,122 A | 2/1976 | Merten et al. | |
| 3,949,002 A | 4/1976 | Feasey et al. | |
| 4,093,624 A | 6/1978 | Revankar et al. | |
| 4,296,237 A | 10/1981 | Cragoe, Jr. et al. | |
| 4,366,189 A | 12/1982 | Burdeska et al. | |
| 4,432,992 A | 2/1984 | Cragoe, Jr. et al. | |
| 4,525,450 A | 6/1985 | Itoh et al. | |
| 4,816,454 A | 3/1989 | Zoller et al. | |
| 5,103,014 A | 4/1992 | Musser et al. | |
| 5,162,360 A | 11/1992 | Creswell et al. | |
| 5,189,045 A | 2/1993 | Peglion et al. | |
| 5,319,099 A | 6/1994 | Kamata et al. | |
| 5,494,925 A | 2/1996 | Court et al. | |
| 5,514,691 A | 5/1996 | Chan et al. | |
| 5,614,532 A | 3/1997 | Carling et al. | |
| 5,621,010 A | 4/1997 | Sueda et al. | |
| 5,658,924 A | 8/1997 | Matsuura et al. | |
| 5,721,231 A | 2/1998 | Moriwaki et al. | |
| 5,811,456 A | 9/1998 | Seman et al. | |
| 6,020,357 A | 2/2000 | Pinto et al. | |
| 6,028,085 A | 2/2000 | Bromidge | |
| 6,080,763 A | 6/2000 | Regan et al. | |
| 6,123,964 A | 9/2000 | Asgharnejad et al. | |
| 6,147,088 A | 11/2000 | Goulet et al. | |
| 6,197,599 B1 | 3/2001 | Chin et al. | |
| 6,235,786 B1 | 5/2001 | Dai et al. | |
| 6,294,573 B1 | 9/2001 | Curtin et al. | |
| 6,319,921 B1 | 11/2001 | Cirillo et al. | |
| 6,410,254 B1 | 6/2002 | Finer et al. | |
| 6,500,628 B1 | 12/2002 | Robison | |
| 6,525,046 B1 | 2/2003 | Cirillo et al. | |
| 6,645,990 B2 | 11/2003 | Askew et al. | |

(Continued)

FOREIGN PATENT DOCUMENTS

| | | |
|---|---|---|
| CN | 101528744 A | 9/2009 |
| CN | 101553232 A | 10/2009 |

(Continued)

OTHER PUBLICATIONS

U.S. Appl. No. 11/963,740, filed Dec. 21, 2007 Patented U.S. Pat. No. 8,163,756.

(Continued)

*Primary Examiner* — Genevieve S Alley
(74) *Attorney, Agent, or Firm* — Goodwin Procter LLP

(57) ABSTRACT

Provided herein are low impurity compositions comprising a compound represented by Formula (I):

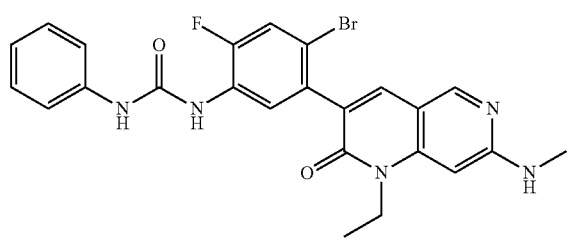

Formula (I)

which are useful in the treatment of disorders related to the activity of the c-KIT and PDGFRα kinases, and oncogenic forms thereof.

12 Claims, No Drawings

(56) References Cited

U.S. PATENT DOCUMENTS

| | | |
|---|---|---|
| 6,763,607 B2 | 7/2004 | Beyerinck et al. |
| 6,916,924 B2 | 7/2005 | Tan et al. |
| 6,973,741 B2 | 12/2005 | Beyerinck et al. |
| 7,071,199 B1 | 7/2006 | Hirst et al. |
| 7,135,550 B2 | 11/2006 | Come et al. |
| 7,144,911 B2 | 12/2006 | Flynn et al. |
| 7,202,257 B2 | 4/2007 | Flynn et al. |
| 7,211,575 B2 | 5/2007 | Moss et al. |
| 7,279,576 B2 | 10/2007 | Flynn et al. |
| 7,342,037 B2 | 3/2008 | Flynn et al. |
| 7,531,566 B2 | 5/2009 | Flynn et al. |
| 7,666,895 B2 | 2/2010 | Flynn et al. |
| 7,737,283 B2 | 6/2010 | Flynn et al. |
| 7,790,756 B2 | 9/2010 | Flynn et al. |
| 7,897,762 B2 | 3/2011 | Flynn et al. |
| 8,143,293 B2 | 3/2012 | Flynn et al. |
| 8,163,756 B2 | 4/2012 | Flynn et al. |
| 8,188,113 B2 | 5/2012 | Flynn et al. |
| 8,278,331 B2 | 10/2012 | Flynn et al. |
| 8,343,550 B2 | 1/2013 | Beyerinck et al. |
| 8,461,179 B1 | 6/2013 | Flynn et al. |
| 8,486,951 B2 | 7/2013 | Flynn et al. |
| 8,569,319 B2 | 10/2013 | Flynn et al. |
| 8,586,565 B2 | 11/2013 | Flynn et al. |
| 8,637,672 B2 | 1/2014 | Flynn et al. |
| 8,669,289 B2 | 3/2014 | Li |
| 8,741,911 B2 | 6/2014 | Allgeier et al. |
| 8,828,443 B2 | 9/2014 | Beyerinck et al. |
| 8,921,565 B2 | 12/2014 | Flynn et al. |
| 8,940,756 B2 | 1/2015 | Flynn et al. |
| 9,012,635 B2 | 4/2015 | Flynn et al. |
| 9,133,183 B2 | 9/2015 | Flynn et al. |
| 9,181,223 B2 | 11/2015 | Kaufman et al. |
| 9,187,474 B2 | 11/2015 | Flynn et al. |
| 9,193,719 B2 | 11/2015 | Flynn et al. |
| 9,248,584 B2 | 2/2016 | Friesen et al. |
| 9,265,731 B2 | 2/2016 | Ray et al. |
| 9,309,224 B2 | 4/2016 | Flynn et al. |
| 9,334,267 B2 | 5/2016 | Flynn et al. |
| 9,339,467 B2 | 5/2016 | Beyerinck et al. |
| 9,382,228 B2 | 7/2016 | Flynn et al. |
| 9,387,202 B2 | 7/2016 | Flynn et al. |
| 9,457,019 B2 | 10/2016 | Flynn et al. |
| 9,545,407 B2 | 1/2017 | Shu et al. |
| 9,724,664 B2 | 8/2017 | Friesen et al. |
| 10,300,443 B2 | 5/2019 | Friesen et al. |
| 10,383,941 B2 | 8/2019 | Beyerinck et al. |
| 10,675,602 B2 | 6/2020 | Friesen et al. |
| 10,966,966 B2 | 4/2021 | Soto et al. |
| 11,103,507 B2 | 8/2021 | Flynn et al. |
| RE48,731 E | 9/2021 | Flynn et al. |
| 11,185,535 B2 | 11/2021 | Kaufman et al. |
| 11,266,635 B2 | 3/2022 | Soto et al. |
| 11,344,536 B1 | 5/2022 | Soto et al. |
| 11,395,818 B2 | 7/2022 | Kaufman et al. |
| 11,426,390 B2 | 8/2022 | Soto et al. |
| 11,433,056 B1 | 9/2022 | Soto et al. |
| 11,529,336 B2 | 12/2022 | Soto et al. |
| 11,534,432 B2 | 12/2022 | Soto et al. |
| 11,576,903 B2 | 2/2023 | Kaufman et al. |
| 11,576,904 B2 | 2/2023 | Soto et al. |
| 11,612,591 B2 | 3/2023 | Kaufman et al. |
| 2002/0058678 A1 | 5/2002 | Cirillo et al. |
| 2002/0077486 A1 | 6/2002 | Scarborough et al. |
| 2002/0165394 A1 | 11/2002 | Dumas et al. |
| 2002/0193405 A1 | 12/2002 | Askew et al. |
| 2003/0060455 A1 | 3/2003 | Moss et al. |
| 2003/0105139 A1 | 6/2003 | Gaster et al. |
| 2003/0144278 A1 | 7/2003 | Riedl et al. |
| 2003/0181442 A1 | 9/2003 | Riedl et al. |
| 2003/0207870 A1 | 11/2003 | Dumas et al. |
| 2003/0216396 A1 | 11/2003 | Dumas et al. |
| 2003/0232865 A1 | 12/2003 | Cirillo et al. |
| 2004/0043388 A1 | 3/2004 | Come et al. |
| 2004/0067938 A1 | 4/2004 | Zhang et al. |
| 2004/0102636 A1 | 5/2004 | Miller et al. |
| 2004/0157827 A1 | 8/2004 | Pevarello et al. |
| 2004/0167224 A1 | 8/2004 | Ozaki et al. |
| 2004/0171075 A1 | 9/2004 | Flynn et al. |
| 2004/0180906 A1 | 9/2004 | Flynn et al. |
| 2004/0229937 A1 | 11/2004 | Dumas et al. |
| 2005/0014753 A1 | 1/2005 | Ding et al. |
| 2005/0148605 A1 | 7/2005 | Grotzfeld et al. |
| 2005/0165024 A1 | 7/2005 | Milanov et al. |
| 2005/0165031 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0192314 A1 | 9/2005 | Mehta et al. |
| 2005/0197371 A1 | 9/2005 | Milanov et al. |
| 2005/0256174 A1 | 11/2005 | Wood et al. |
| 2005/0261315 A1 | 11/2005 | Mehta et al. |
| 2005/0267182 A1 | 12/2005 | Milanov et al. |
| 2005/0288286 A1 | 12/2005 | Flynn et al. |
| 2006/0229337 A1 | 10/2006 | Brittelli et al. |
| 2006/0247186 A1 | 11/2006 | Carter et al. |
| 2007/0037794 A1 | 2/2007 | Ungashe et al. |
| 2007/0078121 A1 | 4/2007 | Flynn et al. |
| 2007/0155764 A1 | 7/2007 | Lang et al. |
| 2007/0179130 A1 | 8/2007 | Bannen |
| 2007/0191336 A1 | 8/2007 | Flynn et al. |
| 2007/0244120 A1 | 10/2007 | Dumas et al. |
| 2007/0293685 A1 | 12/2007 | Fritch et al. |
| 2008/0009527 A1 | 1/2008 | Dumas et al. |
| 2008/0045531 A1 | 2/2008 | Flynn et al. |
| 2008/0045706 A1 | 2/2008 | Flynn et al. |
| 2008/0064717 A1 | 3/2008 | Iyengar et al. |
| 2008/0090856 A1 | 4/2008 | Flynn et al. |
| 2008/0113967 A1 | 5/2008 | Flynn et al. |
| 2008/0114006 A1 | 5/2008 | Flynn et al. |
| 2008/0132506 A1 | 6/2008 | Flynn et al. |
| 2008/0176846 A1 | 7/2008 | Chianelli et al. |
| 2008/0187978 A1 | 8/2008 | Flynn et al. |
| 2008/0194836 A1 | 8/2008 | Gharbaoui et al. |
| 2008/0200530 A1 | 8/2008 | Unett et al. |
| 2008/0207699 A1 | 8/2008 | Hoelzemann et al. |
| 2008/0214545 A1 | 9/2008 | Lee et al. |
| 2008/0220497 A1 | 9/2008 | Flynn et al. |
| 2008/0221192 A1 | 9/2008 | Wan et al. |
| 2008/0248487 A1 | 10/2008 | Flynn et al. |
| 2008/0248548 A1 | 10/2008 | Flynn et al. |
| 2008/0300281 A1 | 12/2008 | Dumas et al. |
| 2009/0069310 A1 | 3/2009 | Flynn et al. |
| 2009/0075986 A1 | 3/2009 | Flynn et al. |
| 2009/0093526 A1 | 4/2009 | Miller et al. |
| 2009/0099190 A1 | 4/2009 | Flynn et al. |
| 2009/0105230 A1 | 4/2009 | Flynn et al. |
| 2009/0124633 A1 | 5/2009 | Jonczyk et al. |
| 2009/0137021 A1 | 5/2009 | Flynn et al. |
| 2009/0192307 A1 | 7/2009 | Michelotti et al. |
| 2009/0215799 A1 | 8/2009 | Stieber et al. |
| 2009/0281089 A1 | 11/2009 | Gunzner et al. |
| 2009/0312349 A1 | 12/2009 | Flynn et al. |
| 2009/0325945 A1 | 12/2009 | Niculescu-Duvaz et al. |
| 2010/0075971 A1 | 3/2010 | Dumas et al. |
| 2010/0160292 A1 | 6/2010 | Whitney et al. |
| 2010/0209420 A1 | 8/2010 | Lamb et al. |
| 2010/0286215 A1 | 11/2010 | Pelcman et al. |
| 2010/0298290 A1 | 11/2010 | Anand et al. |
| 2011/0077240 A1 | 3/2011 | Mannion et al. |
| 2011/0092461 A1 | 4/2011 | Gunzner et al. |
| 2011/0098293 A1 | 4/2011 | Mannion et al. |
| 2011/0112193 A1 | 5/2011 | Nilsson et al. |
| 2011/0124640 A1 | 5/2011 | Liu et al. |
| 2011/0136760 A1 | 6/2011 | Flynn et al. |
| 2011/0136809 A1 | 6/2011 | Lee et al. |
| 2011/0183997 A1 | 7/2011 | Chianelli et al. |
| 2011/0195110 A1 | 8/2011 | Smith et al. |
| 2011/0237563 A1 | 9/2011 | Costantini |
| 2012/0094980 A1 | 4/2012 | Gunzner et al. |
| 2012/0114605 A1 | 5/2012 | Li |
| 2012/0214808 A1 | 8/2012 | Bloxham et al. |
| 2012/0225057 A1 | 9/2012 | Flynn et al. |
| 2012/0270878 A1 | 10/2012 | Miller et al. |

(56) References Cited

U.S. PATENT DOCUMENTS

| | | |
|---|---|---|
| 2012/0289540 A1 | 11/2012 | Flynn et al. |
| 2013/0071403 A1 | 3/2013 | Rolland et al. |
| 2013/0225581 A1 | 8/2013 | Furuta et al. |
| 2013/0296326 A1 | 11/2013 | Pollock |
| 2014/0088075 A1 | 3/2014 | Flynn et al. |
| 2014/0107100 A1 | 4/2014 | Rice et al. |
| 2014/0147415 A1 | 5/2014 | Moussy et al. |
| 2014/0179632 A1 | 6/2014 | Mannion et al. |
| 2014/0296248 A1 | 10/2014 | Bernards et al. |
| 2014/0296267 A1 | 10/2014 | Fry et al. |
| 2014/0336210 A1 | 11/2014 | Christopher et al. |
| 2015/0031648 A1 | 1/2015 | Le Tiran et al. |
| 2015/0073141 A1 | 3/2015 | Teegarden et al. |
| 2015/0105550 A1 | 4/2015 | Gunzner et al. |
| 2015/0111879 A1 | 4/2015 | Gunzner et al. |
| 2015/0133462 A1 | 5/2015 | Singh et al. |
| 2015/0218652 A1 | 8/2015 | Doebele et al. |
| 2015/0225369 A1 | 8/2015 | Wucherer-Plietker et al. |
| 2015/0246033 A1 | 9/2015 | Flynn et al. |
| 2015/0275306 A1 | 10/2015 | Bernards et al. |
| 2015/0320759 A1 | 11/2015 | Flynn et al. |
| 2016/0009709 A1 | 1/2016 | Cheve et al. |
| 2016/0045532 A1 | 2/2016 | Roberts et al. |
| 2016/0152569 A1 | 6/2016 | Gunzner-Toste et al. |
| 2016/0166679 A1 | 6/2016 | Low et al. |
| 2016/0222012 A1 | 8/2016 | Ruan |
| 2016/0243150 A1 | 8/2016 | Wood et al. |
| 2016/0289663 A1 | 10/2016 | Kiyokawa et al. |
| 2016/0374990 A1 | 12/2016 | Teegarden et al. |
| 2017/0015627 A1 | 1/2017 | Gunzner-Toste et al. |
| 2017/0121321 A1 | 5/2017 | Crews et al. |
| 2017/0174750 A1 | 6/2017 | Lim et al. |
| 2017/0349880 A1 | 12/2017 | Doucey et al. |
| 2017/0360791 A1 | 12/2017 | Joshi-Hangal et al. |
| 2018/0000771 A1 | 1/2018 | Inoue et al. |
| 2018/0071302 A1 | 3/2018 | Abella et al. |
| 2018/0071303 A1 | 3/2018 | Abella et al. |
| 2019/0091217 A1 | 3/2019 | Flynn et al. |
| 2020/0129489 A1 | 4/2020 | Flynn et al. |
| 2020/0253973 A1 | 8/2020 | Flynn et al. |
| 2020/0352920 A1 | 11/2020 | Flynn et al. |
| 2020/0354346 A1 | 11/2020 | Flynn et al. |
| 2020/0354352 A1 | 11/2020 | Flynn et al. |
| 2021/0015801 A1 | 1/2021 | Flynn et al. |

FOREIGN PATENT DOCUMENTS

| | | |
|---|---|---|
| CN | 102731385 A | 10/2012 |
| CN | 105461699 A | 4/2016 |
| CN | 106573002 A | 4/2017 |
| CN | 106822128 A | 6/2017 |
| CN | 108379591 A | 8/2018 |
| CN | 111328283 A | 6/2020 |
| CN | 114902895 A | 8/2022 |
| DE | 1115350 B | 10/1961 |
| DE | 4343831 A1 | 6/1995 |
| EP | 0021228 A1 | 1/1981 |
| EP | 0025232 A1 | 3/1981 |
| EP | 0154190 A1 | 9/1985 |
| EP | 0661276 A1 | 7/1995 |
| EP | 0692483 A4 | 11/1995 |
| EP | 0739884 A2 | 10/1996 |
| EP | 0867435 A1 | 9/1998 |
| EP | 0927555 A1 | 7/1999 |
| EP | 928790 A | 7/1999 |
| EP | 0956855 A1 | 11/1999 |
| EP | 1281399 A2 | 2/2003 |
| EP | 2858646 A1 | 4/2015 |
| EP | 2827900 B1 | 3/2018 |
| FR | 2337554 A1 | 8/1977 |
| FR | 2396549 A2 | 2/1979 |
| GB | 971307 A | 9/1964 |
| GB | 1410279 A | 10/1975 |
| GB | 2220206 A | 1/1990 |
| JP | 59-177557 A | 8/1984 |
| JP | 9-221476 | 8/1997 |
| JP | 2000275886 A | 10/2000 |
| JP | 2001-2687 A | 1/2001 |
| JP | 2010-506948 A | 3/2010 |
| JP | 2015-520186 A | 7/2015 |
| JP | 59-15247 B2 | 5/2016 |
| KR | 20130065368 A | 6/2013 |
| WO | WO-1991/19708 A1 | 12/1991 |
| WO | WO-1992/08693 A1 | 5/1992 |
| WO | WO-1994/18176 A1 | 8/1994 |
| WO | WO-1994/21617 | 9/1994 |
| WO | WO-1994/24095 A1 | 10/1994 |
| WO | WO-1995/006044 A1 | 3/1995 |
| WO | WO-1995/15954 A1 | 6/1995 |
| WO | WO-1995/29902 A1 | 11/1995 |
| WO | WO-1995/34540 A1 | 12/1995 |
| WO | WO-1996/16046 A2 | 5/1996 |
| WO | WO-1996/19477 A1 | 6/1996 |
| WO | WO-1996/023783 A1 | 8/1996 |
| WO | WO-1997/34900 A1 | 9/1997 |
| WO | WO-1997/037989 A2 | 10/1997 |
| WO | WO-1997/40028 A1 | 10/1997 |
| WO | WO-1997/045400 A1 | 12/1997 |
| WO | WO-1998/22103 A1 | 5/1998 |
| WO | WO-1998/52558 A1 | 11/1998 |
| WO | WO-1999/15164 A1 | 4/1999 |
| WO | WO-1999/23091 A1 | 5/1999 |
| WO | WO-1999/23093 A1 | 5/1999 |
| WO | WO-1999/3 7622 A1 | 7/1999 |
| WO | WO-1999/32106 | 7/1999 |
| WO | WO-1999/32110 A1 | 7/1999 |
| WO | WO-1999/32111 | 7/1999 |
| WO | WO-1999/32455 | 7/1999 |
| WO | WO-1999/59959 A1 | 11/1999 |
| WO | WO-2000/06550 A1 | 2/2000 |
| WO | WO-2000/07980 A1 | 2/2000 |
| WO | WO-2000/18738 A1 | 4/2000 |
| WO | WO-2000/21927 A2 | 4/2000 |
| WO | WO-2000/41698 A1 | 7/2000 |
| WO | WO-2000/042012 A1 | 7/2000 |
| WO | WO-2000/43384 A1 | 7/2000 |
| WO | WO-2000/055139 A2 | 9/2000 |
| WO | WO-2000/59506 A1 | 10/2000 |
| WO | WO-2000/071515 A2 | 11/2000 |
| WO | WO-2001/12621 A1 | 2/2001 |
| WO | WO-2001/14372 A2 | 3/2001 |
| WO | WO-2001/74771 A1 | 10/2001 |
| WO | WO-2001/96298 A2 | 12/2001 |
| WO | WO-2002/00647 A1 | 1/2002 |
| WO | WO-2002/14291 A1 | 2/2002 |
| WO | WO-2002/014311 A2 | 2/2002 |
| WO | WO-2002/026712 A2 | 4/2002 |
| WO | WO-2002/28835 A1 | 4/2002 |
| WO | WO-2002/34 727 A2 | 5/2002 |
| WO | WO-2002/060869 A2 | 8/2002 |
| WO | WO-2002/060876 A1 | 8/2002 |
| WO | WO-2002/062763 A2 | 8/2002 |
| WO | WO-2002/070662 A2 | 9/2002 |
| WO | WO-2003/005999 A2 | 1/2003 |
| WO | WO-2003/047579 A1 | 6/2003 |
| WO | WO-2003/053368 A2 | 7/2003 |
| WO | WO-2003/059373 A2 | 7/2003 |
| WO | WO-2003/068223 A1 | 8/2003 |
| WO | WO-2003/068229 A1 | 8/2003 |
| WO | WO-2003/072577 A1 | 9/2003 |
| WO | WO-2003/084539 A2 | 10/2003 |
| WO | WO-2004/004720 A1 | 1/2004 |
| WO | WO-2004/056783 A1 | 7/2004 |
| WO | WO-2004/060305 A2 | 7/2004 |
| WO | WO-2004/060306 A2 | 7/2004 |
| WO | WO-2004/061084 A2 | 7/2004 |
| WO | WO-2004/078128 A2 | 9/2004 |
| WO | WO-2004/078746 A2 | 9/2004 |
| WO | WO-2004/113352 A1 | 12/2004 |
| WO | WO-2005/002673 A1 | 1/2005 |
| WO | WO-2005/012254 A1 | 2/2005 |
| WO | WO-2005/024755 A2 | 3/2005 |
| WO | WO-2005/034869 A2 | 4/2005 |
| WO | WO-2005/048948 A2 | 6/2005 |

(56) References Cited

FOREIGN PATENT DOCUMENTS

| | | |
|---|---|---|
| WO | WO-2005/103011 A1 | 11/2005 |
| WO | WO-2005/110994 A2 | 11/2005 |
| WO | WO-2006/014290 A2 | 2/2006 |
| WO | WO-2006/014325 A2 | 2/2006 |
| WO | WO-2006/018662 A2 | 2/2006 |
| WO | WO-2006/028958 A2 | 3/2006 |
| WO | WO-2006/039718 A2 | 4/2006 |
| WO | WO-2006/040056 A1 | 4/2006 |
| WO | WO-2006/046552 A1 | 5/2006 |
| WO | WO-2006/052936 A2 | 5/2006 |
| WO | WO-2006/062984 A2 | 6/2006 |
| WO | WO-2006/071940 A2 | 7/2006 |
| WO | WO-2006/072589 A2 | 7/2006 |
| WO | WO-2006/078610 A1 | 7/2006 |
| WO | WO-2006/081034 A2 | 8/2006 |
| WO | WO-2006/081335 A2 | 8/2006 |
| WO | WO-2006/099075 A2 | 9/2006 |
| WO | WO-2006/105844 A1 | 10/2006 |
| WO | WO-2007/008917 A2 | 1/2007 |
| WO | WO-2007/042321 A2 | 4/2007 |
| WO | WO-2007/064872 A2 | 6/2007 |
| WO | WO-2007/076473 A2 | 7/2007 |
| WO | WO-2007/081690 A2 | 7/2007 |
| WO | WO-2007/115670 A1 | 10/2007 |
| WO | WO-2007/125330 A1 | 11/2007 |
| WO | WO-2007/136465 A2 | 11/2007 |
| WO | WO-2007/137107 A2 | 11/2007 |
| WO | WO-2008/033858 A2 | 3/2008 |
| WO | WO-2008/033999 A2 | 3/2008 |
| WO | WO-2008/034008 A2 | 3/2008 |
| WO | WO-2008/046003 A2 | 4/2008 |
| WO | WO-2008/051757 A1 | 5/2008 |
| WO | WO-2008/131227 A1 | 10/2008 |
| WO | WO-2008/131253 A1 | 10/2008 |
| WO | WO-2008/140895 A1 | 11/2008 |
| WO | WO-2009/030887 A2 | 3/2009 |
| WO | WO-2009/076454 A2 | 6/2009 |
| WO | WO-2009/109035 A1 | 9/2009 |
| WO | WO-2009/126863 A2 | 10/2009 |
| WO | WO-2009/127822 A2 | 10/2009 |
| WO | WO-2009/138758 A2 | 11/2009 |
| WO | WO-2010/011837 A1 | 1/2010 |
| WO | WO-2010/051373 A1 | 5/2010 |
| WO | WO-2010/124283 A2 | 10/2010 |
| WO | WO-2010/135524 A1 | 11/2010 |
| WO | WO-2011/067306 A1 | 6/2011 |
| WO | WO-2011/123788 A1 | 10/2011 |
| WO | WO-2011/137342 A1 | 11/2011 |
| WO | WO-2011/139891 A1 | 11/2011 |
| WO | WO-2011/150198 A1 | 12/2011 |
| WO | WO-2012/008563 A1 | 1/2012 |
| WO | WO-2012/019015 A2 | 2/2012 |
| WO | WO-2012/035131 A1 | 3/2012 |
| WO | WO-2012/071519 A1 | 5/2012 |
| WO | WO-2012/097021 A1 | 7/2012 |
| WO | WO-2012/138783 A2 | 10/2012 |
| WO | WO-2013/036232 A2 | 3/2013 |
| WO | WO-2013/043569 A1 | 3/2013 |
| WO | WO-2013/066440 A1 | 5/2013 |
| WO | WO-2013/078295 A2 | 5/2013 |
| WO | WO-2013/134243 A1 | 9/2013 |
| WO | WO-2013/134252 A1 | 9/2013 |
| WO | WO-2013/134298 A1 | 9/2013 |
| WO | WO-2013/177420 A2 | 11/2013 |
| WO | WO-2013/184119 A1 | 12/2013 |
| WO | WO-2014/015056 A2 | 1/2014 |
| WO | WO-2014/032755 A2 | 3/2014 |
| WO | WO-2014/036387 A2 | 3/2014 |
| WO | WO-2014/037480 A1 | 3/2014 |
| WO | WO-2014/040242 A1 | 3/2014 |
| WO | WO-2014/040549 A1 | 3/2014 |
| WO | WO-2014/058317 A1 | 4/2014 |
| WO | WO-2014/102376 A1 | 7/2014 |
| WO | WO-2014/102377 A1 | 7/2014 |
| WO | WO-2014/139458 A1 | 9/2014 |
| WO | WO-2014/145004 A1 | 9/2014 |
| WO | WO-2014/145015 A2 | 9/2014 |
| WO | WO-2014/145023 A1 | 9/2014 |
| WO | WO-2014/145025 A2 | 9/2014 |
| WO | WO-2014/145028 A2 | 9/2014 |
| WO | WO-2014/145029 A2 | 9/2014 |
| WO | WO-2014/160183 A1 | 10/2014 |
| WO | WO-2014/182643 A2 | 11/2014 |
| WO | WO-2015/011399 A1 | 1/2015 |
| WO | WO-2015/051252 A1 | 4/2015 |
| WO | WO-2015/069217 A1 | 5/2015 |
| WO | WO-2015/069266 A1 | 5/2015 |
| WO | WO-2015/076213 A1 | 5/2015 |
| WO | WO-2015/092423 A1 | 6/2015 |
| WO | WO-2015/106292 A1 | 7/2015 |
| WO | WO-2015/106294 A1 | 7/2015 |
| WO | WO-2015/148620 A2 | 10/2015 |
| WO | WO-2015/184443 A1 | 12/2015 |
| WO | WO-2016/061228 A1 | 4/2016 |
| WO | WO-2016/061231 A1 | 4/2016 |
| WO | WO-2016/096903 A1 | 6/2016 |
| WO | WO-2016/103223 A1 | 6/2016 |
| WO | WO-2016/114322 A1 | 7/2016 |
| WO | WO-2016/135046 A1 | 9/2016 |
| WO | WO-2016/154524 A1 | 9/2016 |
| WO | WO-2016/196141 A1 | 12/2016 |
| WO | WO-2017/013160 A1 | 1/2017 |
| WO | WO-2017/042944 A1 | 3/2017 |
| WO | WO-2017/079267 A1 | 5/2017 |
| WO | WO-2017/117182 A1 | 7/2017 |
| WO | WO-2017/146794 A1 | 8/2017 |
| WO | WO-2017/146795 A1 | 8/2017 |
| WO | WO-2017/214514 A1 | 12/2017 |
| WO | WO-2018/005737 A1 | 1/2018 |
| WO | WO-2018/052053 A1 | 3/2018 |
| WO | WO-2018/053189 A2 | 3/2018 |
| WO | WO-2018/106595 A1 | 6/2018 |
| WO | WO-2018/195450 A1 | 10/2018 |
| WO | WO-2018/222173 A1 | 12/2018 |
| WO | WO-2018/222644 A1 | 12/2018 |
| WO | WO-2019/084462 A1 | 5/2019 |
| WO | WO-2020/185812 A1 | 9/2020 |

OTHER PUBLICATIONS

U.S. Appl. No. 11/870,388, filed Oct. 10, 2007, Patented, U.S. Pat. No. 7,790,756.
U.S. Appl. No. 12/829,561, filed Jul. 2, 2010, Patented, U.S. Pat. No. 8,586,565.
U.S. Appl. No. 11/854,354, filed Sep. 12, 2007, Patented, U.S. Pat. No. 8,188,113.
U.S. Appl. No. 10/746,460, filed Dec. 24, 2003, Patented, U.S. Pat. No. 7,144,911.
U.S. Appl. No. 10/886,329, filed Jul. 6, 2004, Patented, U.S. Pat. No. 7,202,257.
U.S. Appl. No. 11/450,840, filed Jun. 9, 2006, Patented, U.S. Pat. No. 7,342,037.
U.S. Appl. No. 11/336,708, filed Jan. 20, 2006, Patented, U.S. Pat. No. 7,531,566.
U.S. Appl. No. 11/450,850, filed Jun. 9, 2006, Patented, U.S. Pat. No. 7,666,895.
U.S. Appl. No. 10/746,607, filed Dec. 24, 2003, Patented, U.S. Pat. No. 7,279,576.
U.S. Appl. No. 11/854,293, filed Sep. 12, 2007, Patented, U.S. Pat. No. 7,897,762.
U.S. Appl. No. 12/105,408, filed Apr. 18, 2008, Patented, U.S. Pat. No. 8,143,293.
U.S. Appl. No. 13/590,955, filed Aug. 21, 2012, Patented, U.S. Pat. No. 8,486,951.
U.S. Appl. No. 11/450,849, filed Jun. 9, 2006, Patented, U.S. Pat. No. 7,737,283.
U.S. Appl. No. 13/785,575, filed Mar. 5, 2013, Patented, U.S. Pat. No. 8,741,911.
U.S. Appl. No. 12/608,578, filed Oct. 29, 2009, Patented, U.S. Pat. No. 8,278,331.

(56) References Cited

OTHER PUBLICATIONS

U.S. Appl. No. 13/098,247, filed Apr. 29, 2011, Patented, U.S. Pat. No. 8,569,319.
U.S. Appl. No. 13/559,170, filed Jul. 26, 2012, Patented, U.S. Pat. No. 8,637,672.
U.S. Appl. No. 14/214,134, filed Mar. 14, 2014, Patented, U.S. Pat. No. 9,133,183.
U.S. Appl. No. 14/383,803, filed Mar. 5, 2013, Patented, U.S. Pat. No. 9,187,474.
U.S. Appl. No. 13/491,394, filed Jun. 7, 2012, Patented, U.S. Pat. No. 8,461,179.
U.S. Appl. No. 13/098,247, filed Mar. 13, 2013, Patented, U.S. Pat. No. 8,940,756.
U.S. Appl. No. 16/387,315, filed Apr. 17, 2019, Pending.
U.S. Appl. No. 14/214,127, filed Mar. 14, 2014, Patented, U.S. Pat. No. 9,012,635.
U.S. Appl. No. 13/683,277, filed Nov. 21, 2012, Patented, U.S. Pat. No. 8,921,565.
U.S. Appl. No. 14/549,125, filed Nov. 20, 2014, Patented, U.S. Pat. No. 9,387,202.
U.S. Appl. No. 14/214,160, filed Mar. 14, 2014, Patented, U.S. Pat. No. 9,193,719.
U.S. Appl. No. 14/214,171, filed Mar. 14, 2014, Patented, U.S. Pat. No. 9,181,223.
U.S. Appl. No. 14/214,185, filed Mar. 14, 2014, Patented, U.S. Pat. No. 9,382,228.
U.S. Appl. No. 14/214,179, filed Mar. 14, 2014, Patented, U.S. Pat. No. 9,309,224.
U.S. Appl. No. 14/383,799, filed Mar. 5, 2013, Patented, U.S. Pat. No. 9,334,267.
U.S. Appl. No. 14/535,900, filed Nov. 7, 2014, Patented, U.S. Pat. No. 9,457,019.
U.S. Appl. No. 16/943,821, filed Jul. 30, 2020, Pending, US 2021-0145805 A1.
U.S. Appl. No. 16/943,871, filed Jul. 30, 2020, Pending, US 2020-0352920 A1.
U.S. Appl. No. 16/725,282, filed Dec. 23, 2019, Patented, U.S. Pat. No. 11,103,507.
U.S. Appl. No. 16/870,384, filed May 8, 2020, Patented, U.S. Pat. No. 11,530,206.
U.S. Appl. No. 16/870,418, filed May 8, 2020, Patented, U.S. Pat. No. 11,518,758.
U.S. Appl. No. 16/902,989, filed Jun. 16, 2020, Patented, U.S. Pat. No. 11,590,134.
U.S. Appl. No. 16/991,644, filed Aug. 12, 2020, Pending, US 2022-0047573 A1.
U.S. Appl. No. 17/028,640, filed Sep. 22, 2020, Patented, U.S. Pat. No. 10,966,966.
U.S. Appl. No. 17/180,234, filed Feb. 19, 2021, Patented, U.S. Pat. No. 11,185,535.
U.S. Appl. No. 17/180,241, filed Feb. 19, 2021, Patented, U.S. Pat. No. 11,395,818.
U.S. Appl. No. 17/504,133, filed Oct. 18, 2021, Patented, U.S. Pat. No. 11,576,103.
U.S. Appl. No. 18/314,348, filed May 9, 2023, Pending.
U.S. Appl. No. 17/358,137, filed Jun. 25, 2021, Patented, U.S. Pat. No. 11,679,110.
U.S. Appl. No. 17/598,977, filed Jan. 25, 2022, Patented, U.S. Pat. No. 11,426,390.
U.S. Appl. No. 17/583,985, filed Jan. 25, 2022, Patented, U.S. Pat. No. 11,344,536.
U.S. Appl. No. 17/727,307, filed Apr. 22, 2022, Patented, U.S. Pat. No. 11,534,432.
U.S. Appl. No. 17/735,820, filed May 3, 2022, Patented, U.S. Pat. No. 11,612,591.
U.S. Appl. No. 18/148,766, filed Dec. 30, 2022, Pending, US 2023-0201175 A1.
U.S. Appl. No. 17/845,275, filed Jun. 21, 2022, Pending, US 2022-0370423 A1.
U.S. Appl. No. 17/845,278, filed Jun. 21, 2022, Pending, US 2022-0370424 A1.
U.S. Appl. No. 17/180,218, filed Feb. 19, 2021, Patented, U.S. Pat. No. 11,266,635.
U.S. Appl. No. 17/583,977, filed Jan. 25, 2022, Patented, U.S. Pat. No. 11,426,390.
U.S. Appl. No. 17/869,108, filed Jul. 20, 2022, Pending, US 2022-0370426.
U.S. Appl. No. 17/583,985, filed Jan. 25, 2022, Patented, U.S. Pat. No. 11,344,546.
U.S. Appl. No. 17/735,678, filed May 3, 2022, Patented, U.S. Pat. No. 11,529,336.
U.S. Appl. No. 17/735,682, filed May 3, 2022, Patented, U.S. Pat. No. 11,576,904.
U.S. Appl. No. 17/938,353, filed Oct. 6, 2022, Pending.
U.S. Appl. No. 17/735,862, filed May 3, 2022, Patented, U.S. Pat. No. 11,433,056.
U.S. Appl. No. 18/091,743, filed Dec. 30, 2022, Pending, US 2023-0145926 A1.
U.S. Appl. No. 18/140,942, filed Apr. 28, 2023, Pending.
U.S. Appl. No. 17/833,272, filed Jan. 25, 2022, Pending, US 2023-0039712 A1.
U.S. Appl. No. 17/832,224, filed Jun. 3, 2022, Pending, US 2023-0047915 A1.
U.S. Appl. No. 18/078,269, filed Dec. 9, 2022, Pending.
U.S. Appl. No. 18/078,271, filed Dec. 9, 2022, Pending.
U.S. Appl. No. 18/073,721, filed Dec. 9, 2022, Pending.
U.S. Appl. No. 18/152,993, filed Jan. 11, 2023, Pending.
"A Safety, Tolerability and PK Study of DCC-2618 in Patients With Advanced Malignancies," ClinicalTrials.gov, Jan. 12, 2018, pp. 1-11. Retrieved from the Internet: URL: <https://clinicaltrials.gov/ct2/show/NC>.
"Additions and Corrections", Journal of Medicinal Chemistry, 32(12):2583 (1989).
"NHLBI LBC Computational Biophysics Scetion", CHARMM Documentation Index, http://www.lobos.nih.gov/Charmm/chmdoc.html, printed Mar. 4, 2005.
"Trilateral Project WM4—Comparative Studies in New Technologies: Report on Comparative Study on Protein 3-Dimensional Structure Related Claims—ANNEX 3: Comments of the USPTO", Vienna, Austria, Nov. 4-8, pp. 58-79 (2002).
Advisory Action of U.S. Appl. No. 17/180,241 dated Jan. 7, 2022, 4 pages.
Aklilu, et al., "Increased PTHRP Production by a Tyrosine Kinase Oncogene, Tpr-Met: Rose of the Ras Signaling Pathway", The American Physiological Society, pp. E277-E283 (1996).
Albericio, et al., "Synthesis of a Sulfaydantion Library", J. Comb. Chem., 3:290-300 (2001).
Almerico, et al., "On the Preparation of 1-aryl-2-heteroaryl- and 2-aryl-1-heteroaryl-pyrroles as Useful Building Blocks for Biologically Interesting Heterocycles", ARKIVOC, Rudy Abramovitch Issue, pp. 129-142 (2001).
Antonescu, et al., "Acquired Resistance to Imatinib in Gastrointestinal Stromal Tumor Occurs Through Secondary Gene Mutation," Clinical cancer research : an official journal of the American Association for Cancer Research, 11(11):4182-4190 (2005).
Anzai, et al., "Alkyl- and Arylthiation of Uracil and Indole", J. Heterocyclic Chem., 16:567-569 (1979).
Askew, et al., "Molecular Recognition with Convergent Functional Groups: 6. Synthetic and Structural Studies with a Model Receptor for Nucleic Acid Components", J. Am. Chem., 111:1082-1090 (1989).
Assessment Report for Tukysa (tucatinib), European Medicines Agency, Dec. 10, 2020.
Avruch, J. et al., "Ras Activation of the Raf Kinase: Tyrosine Kinase Recmitment of the MAP Kinase Cascade," Recent Prag Harm. Res. (2001) 56: 127-155.
Bai et al., "Targeting the KITactivating switch control pocket: a novel mechanism to inhibit neoplastic mast cell proliferation and mast cell activation," *Leukemia* (2013), vol. 27, pp. 278-285.
Bais, et al., "Inhibition of Endogenous Wxalate Production: Biochemical Consideration of the Roles of Glycollate Oxidase and Lactate Dehydrogenase", Clinical Science, 76:303-309 (1989).

(56) References Cited

OTHER PUBLICATIONS

Baker, et al., "Irreversible Enzyme Inhibitors. 188. Inhibition of Mammalian Thymidine Phosphorylase", Journal of Medicinal Chemistry, 14:612-616 (1971).

Banks et al., Discovery and pharmacological characterization of AZD3229, a potent KIT/PDGFR inhibitor fortreatment of gastrointestinal stromal tumors, Sci. Transl. Med. 12, (2020).

Barker, et al., "Characterization of pp60c-src Tyrosine Kinase Activities Using a Continuous Assay: Autoactivation of the Enzyme is an Intermolecular Autophosphorylation Process", Biochemist, 35:14843-14851 (1995).

Barvian, et al., "Pyrido[2,3-d]pyrimidin-7-one Inhibitors of Cyclin-Dependent Kinases," J Med Chem. (2000) 43: 4606-4616.

Bausch, et al., "Proton-Transfer Chemistry of Urazoles and Related Imides, and Diacyl H drazides", J. Org. Chem., 56:5643-5651 (1991).

Beghini, et al., "C-kit mutations in core binding factor leukemias," Blood Journal, 95(2):726-727 (2000).

Benvenuti, et al., "Crystallization of Soluble Proteins in Vapor Diffusion for X-Ray Crystallography", Nature Protocols, 2(7):1633-1651 (2007).

Blay, et al., "Ripretinib in patients with advanced gastrointestinal stromal tumours (INVICTUS): a double-blind, randomised, placebo-controlled, phase 3 trial", Lancet Oncology, 21:923-934 (2020).

Bolton, et al., "Chapter 17. Ras Oncogene Directed Approaches in Cancer Chemotherapy," Ann. Rep. Med. Chem. (1994) 29: 165-174.

Bosca, et al., "Circular Dichroism Analysis of Ligand-Induced Conformational Changes in Protein Kinase C", Biochem. J., 290:827-832 (1993).

Boschelli, et al., "4-Anilino-3-quinolinecarbonitriles: An Emerging Class of Kinase Inhibitors", Current Topics in Medicinal Chemist, 2:1051-1063 (2002).

Bourdon NEC, et al., "Synthesis and Pharmacological Evaluation of New Pyrazolidine-3,5-diones as AT 1 Angiotensin II Receptor Antagonists", J. Med. Chem., 43:2685-2697 (2000).

Boyer, "Small Molecule Inhibitors of KDR (VEGFR-2) Kinase: An Overview of Structure Activit Relationships", Current Topics in Medicinal Chemist, 2:973-1000 (2002).

Brady, et al., "Fast Prediction and Visualization of Protein Binding Pockets with PASS". Journal of Computer-Aided Molecular Desi n, 14:383-401 (2000).

Branford, et al., "High Frequency of Point Mutations Clustered Within the Adenosine Triphosphate-binding Region of BCR/ABL in Patients With Chronic Myeloid Leukemia or Ph-positive Acute Lymphoblastic Leukemia Who Develop Imatinib (ST1571)resistance," Blood (2002) vol. 99, pp. 3472-3475.

Brasher, et al., "C-Abul has High Intrinsic Tyrosine Kinase Activity that is Stimulated by Mutation of the Src Homology 3 Domain and by Autophosphorylation at Two Distinct Re ulator T rosines", Journal of Biolo ical Chemistr, 275:35631-35637 (2000).

Bullock, et al., "Prospects for Kinase Activity Modulators in the Treatment of Diabetes and Diabetic Complications", Current Topics in Medicinal Chemistr, 2:915-938 (2002).

Byron, et al., "The Synthesis of some Substituted Biphenyl-4-carboxylic Acids, 4-Biphenylylacetic Acids, and 4-Aminobiphenyls", J. Chem. Soc. (C), Organic, pp. 840-845 (1966).

Cardillo, et al., "Su lie 1,2-difenil-3.5-dichetopirazolidine", Gazz. Chim., Ital., 9:973-985 (1966).

Carr, J. B., et al., "Isoxazolc Anthelmintics," .J /'vied. Chem (1977) vol. 20, No. 7, pp. 934-939.

Chan et al., "Copper promoted C—N and C—O bond cross-coupling with phenyl and pyridylboronates," *Tetrahedron Letters* (2003) vol. 44, pp. 3863-3865.

Chan, "Promotion of Reaction of N—H Bonds with Triarylbismuth and Cupric Acetate," *Tetrahedron Letters* (1996) vol. 37, No. 50, pp. 9013-9016.

Chan, et al., "New N- and O-Arylations with Phenylboronic Acids and Cupric Acetate," Tetrahedron Lett. (1998) 39: 2933-2936.

Chen, et al., "Biochemical Evidence for the Autophosphorylation and Transphosphorylation of Transforming Growth Factor 13 Receptor Kinases", Proc. Natl. Acad. Sci. USA, 92:1565-1569 (1995).

Cheng, et al., "Novel Solution Phase Strategy for the Synthesis of Chemical Libraries Containing Small Organic Molecules", J. Am. Chem. Soc., 118:2567-2573 (1996).

Cheng, et al., "Synthesis and SAR of Heteroaryl-phenyl-substituted Pyrazole Derivatives as Highly Selective and Potent Canine COX-2 Inhibitors", Bioorganic & Medicinal Chemistry Letters, 16:2076-2080 (2006).

Chu, et al., "Using Affinity Capillary Electrophoresis to Determine Binding Stoichiometries of Protein-Ligand Interactions", Biochemistry, 33:10616-10621 (1994).

Cirillo, et al. "The Non-Diaryl Heterocycle Classes of p38 MAP Kinase Inhibitors", Current Topics in Medicinal Chemistry, 2:1021-1035 (2002).

Clinical trial NCT03353753 Phase 3 Study of DCC-2618 vs Placebo in Advanced GIST Patients Who Have Been Treated With Prior Anticancer Therapies (invictus)—clinicaltrials.gov—Nov. 27, 2017.

Clinical trial NCT02571036—A Safety, Tolerability and PK Study of DCC-2618 in Patients With Advanced Malignancies—clinicaltrials.gov—Dec. 16, 2015.

Clinical trial NCT02571036—A Safety, Tolerability and PK Study of DCC-2618 in Patients With Advanced Malignancies—clinicaltrials.gov—Feb. 10, 2016.

Clinical trial NCT02571036—A Safety, Tolerability and PK Study of DCC-2618 in Patients With Advanced Malignancies—clinicaltrials.gov—May 25, 2017.

Clinical trial NCT02571036—A Safety, Tolerability and PK Study of DCC-2618 in Patients With Advanced Malignancies—clinicaltrials.gov—Nov. 3, 2015.

Clinical trial NCT02571036—A Safety, Tolerability and PK Study of DCC-2618 in Patients With Advanced Malignancies—clinicaltrials.gov—Oct. 29, 2015.

Clinical trial NCT02571036—A Safety, Tolerability and PK Study of DCC-2618 in Patients With Advanced Malignancies—clinicaltrials.gov—Oct. 8, 2015.

Clinical trial NCT02571036—A Safety, Tolerability and PK Study of DCC-2618 in Patients With Advanced Malignancies—clinicaltrials.gov—Sep. 17, 2018.

Clinical trial NCT03353753 Phase 3 Study of DCC-2618 vs Placebo in Advanced GIST Patients Who Have Been Treated With Prior Anticancer Therapies (invictus)—clinicaltrials.gov—Nov. 21, 2018.

Closier, et al., "Nitrofuryl Heterocyclics. 1", Journal of Medicinal Chemistry, 13(4):638-640 (1970).

Cockerill, et al., "Small Molecule Inhibitors of the Class 1 Receptor Tyrosine Kinase Family", Current Topics in Medicinal Chemistry, 2:1001-1010 (2002).

Colton, et al., "Affinity Capillary Electrophoresis: A Physical-Organic Tool for Studying Interactions in Biomolecular Recoqnition", Electrophoresis, 19:367-382 (1998).

Corless, et al., "Biology of Gastrointestinal Stromal Tumors," Journal of Clinical Oncology, 22(18):3813-3825 (2004).

Cortes, et al., "Results of Imatinib Mesylate Therapy in Patients with Refractory or Recurrent Acute Myeloid Leukemia, High-Risk Myelodysplastic Syndrome, and Mveloproliferative Disorders", Cancer, 97(11 ):2760-2766 (2003).

Cortes, Javier, et al., "Eribulin Monotherapy Versus Treatment of Physician's Choice in Patients With Metastatic Breast Cancer (EMBRACE): A Phase 3 Open-label Randomised Study", The Lancet, vol. 377, No. 9769, Mar. 1, 2011 (Mar. 1, 2011), pp. 914-923, ISSN: 0140-6736, DOI: 10.1016/S0140-6736(11 )60070-6.

Cross, et al., "Inhibition of Glycogen Synthase Kinase-3 by Insulin Mediated by Protein Kinase B", Nature, 378:785- 789 (1995).

Cudney, "Preface: Protein Crystallization and Dumb Luck", The Rigaku Journal, 16(1):1-7 (1999).

Dajani, et al., "Crystal Structur of Glycogen Synthase Kinas 3j3: Structural Basis for Phosphate-Primed Substrate Specificity and Autoinhibition", Cell, 105:721-732 (2001).

(56) References Cited

OTHER PUBLICATIONS

Dajani, et al., "Structural Basis for Recruitment of Glycogen Synthase Kinase 313 to the Axin-APC Scaffold Complex", EMBO, 22(3):494-501 (2003).
Daley, et al., "Induction of Chronic Myelogenous Leukemia in Mice by the P21 otcriat, Gene of the Philadelphia Chromosome," Science (Feb. 16, 1990) vol. 247, pp. 824-830.
Database Registry [Online] Chemical Abstracts Service, Columbus, Ohio, US; May 27, 2010, XP002777425, retrieved from STN accession No. 1225278-16-9 RN (2 pages).
Davies, H. et al., "Mutations of the BRAF gene in human cancer," Nature (Jun. 2002) 41 7: 949-954.
Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).
De Boer, et al., "Synthesis and Characterization of Conjugated Mono- and Dithiol Oligomers and Characterization of Their Self-Assembled Monolayers", Langmuir, 19:4272-4284 (2003).
De Palma et al., "Angiopoietin-2 TIEs Up Macrophages in Tumor Angiogenesis" Clin Cancer Res; 17(16) Aug. 15, 2011.
De Silva, et al., "Gastrointestinal Stromal Tumors (GIST): C-kin Mutations, CD117 Expression, Differential Diagnosis and Targeted Cancer Therapy with Imatinib", Pathology Oncology Research, 9(1):13-19 (2003).
Debiec-Rychter, et al., "Mechanisms of Resistance to Imatinib Mesylate in Gastrointestinal Stromal Tumors and Activity of the PKC412 Inhibitor Against Imatinib-Resistant Mutants," Gastroenterology, 128(2):270-279 (2005).
Deciphera Pharmaceuticals LLC, "DCC-2618, a small molecule inhibitor of normal and mutant KIT kinase for treatment of refractory gastrointestinal stromal tumors (GIST)" (Presented on Sep. 24, 2011 at GIST Summit 2011 on "Gastrointestinal stromal tumors.").
Deciphera Pharmaceuticals LLC, "Deciphera Pharmaceuticals announces positive top-line results from INVICTUS pivotal phase 3 clinical study of Ripretinib in patients with advanced gastrointestinal stromal tumors", 1-3 (2019).
Deciphera Pharmaceuticals LLC, "Deciphera Pharmaceuticals Initiates Pivotal Phase 3 Clinical Study of Ripretinib (DCC-2618) in Second-line Patients with Gastrointestinal Stromal Tumors ("INTRIGUE" Study)", 1-2 (2018).
Deciphera Pharmaceuticals LLC, "Qinlock Full Prescribing Information", 1-18 (2020).
Deng, et al., "Expression, Characterization, and Crystallization of the Pyrophosphate-Dependent Phosphofructo-1-Kinase of Borrelia Burgdorferi", Archives of Biochemistry and Biophysics, 371(2):326-331 (1999).
Dess, et al., "A Useful 12-1-5 Triacetoxyperiodiane (the Dess-Martin Periodiane) for Selective Oxidation of Primary or Secondary Alcohols and a Variety of Related 12-1-5 Species", J. Am. Chem. Soc., 113:7277-7287 (1991).
Dong, J., Overcoming Resistance TO BRAF And MEK inhibitors by Simultaneous Suppression of CDK4. InTech. Jan. 30, 2013. Melanoma—From Early Detection to Treatment, Chapter 1; abstract; p. 7, second paragraph; p. 9, figure 4; DOI: 10.5772/53620.
Dumas, "Preface", Current Topics in Medicinal Chemistry (2002).
Dumas, "Protein Kinase Inhibitors: Emerging Pharmacophores", Exp. Opin. Ther. Patent, 11:405-429 (2001).
Dumas, et al., "Discovery of a New Class of p38 Kinase Inhibitors", Bioorganic & Medicinal Chemistry Letters, 10:204 7-2050 (2000).
Dumas, et al., "Recent Developments in the Discovery of Protein Kinase Inhibitors From the Urea Ciass," Current Opinion in Drug Discovery & Development (2004) vol. 7, No. 5, pp. 600-616.
Ettmayer, et al., "Lessons Learned from Marketed and Investigational Prodrugs," Journal of Medicinal Chemistry (May 6, 2004) vol. 47, No. 10, pp. 2393-2404.
Ewing, "Critical Evaluation of Search Algorithms for Automated Molecular Docking and Database Screening", Journal of Computational Chemistry, 18(9):1175-1189 (1997).

Examination Report in Indian Patent App. No. 11241/DELNP/2014 dated Apr. 1, 2019.
Faderl et al., "The Biology of Chronic Myeloid Leukemia," The New England Journal of Medicine (Jul. 15. 1999) vol. 341. No. 3. pp. 164-172.
Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).
Fathalla, "Synthesis of New Pyrazolo[1,5-a]pyrimidine Derivative Using 5-Aminouracil and Ketene Dithiacetal", Arch Pharm Res, 22(6):571-574 (1999).
Fathalla, et al., "Synthesis of New Uracil-5-Sulfonamide Derivatives and Immuno-Stimulatory Effect of a Chemically Modified Hemolymph of Biomphalaria Alexandrina on Schistosoma Manosi Infected Mice", Arch Pharm Res., 26(5):358-366 (2003).
Fathalla, et al., "Synthesis of New Uracil-5-Sulphonamide-p-Phenyl Derivatives and Their Effect on *Biomphalaria alexandrina* Snail's Nucleoproteins", Arch. Pharm. Res., 23(2):128-138 (2000).
Flatt, et al., "Synthesis of Thiol Substituted Oligoanilines for Molecular Device Candidates", Tetrahedron Letters, 44:6699-6702 (2003).
Fletcher, et al., "Diagnosis of Gastrointestinal Stromal Tumors: A Consensus Approach", 33(5):459-465 (2002).
Fletcher, et al., "KIT Mutations in GIS, Current Opinion in Genetics & Development," Science Direct, p. 3-7 (2007).
Frame, et al., "A Common Phosphate Binding Site Explains the Unique Substrate Specificity of GSK3 and Its Inactivation by Phosphorylation", Molecular Cell, 7:1321-1327 (2001).
Furyua, et al., "Addition of 4-Ethoxyimidazoles to Dimethyl Acetylenedicarboxylate and Transformation of the Adducts to Pyrimidian-5-yl Acetates", Chem. Pharm. Bull., 36(5):1669-1675 (1988).
Gajiwala, et al., "KIT kinase mutants show unique mechanisms of drug resistance to imatinib and sunitinib in gastrointestinal stromal tumor patients," Proceedings of the National Academy of Sciences of the USA 106(5):1542-1547 (2009).
Garcia-Tellado, et al., "Molecular Recognition in the Solid Waste State: Controlled Assembly of Hydrogen-Bonded Molecular Sheets", J. Am. Chem. Soc., 113:9265-9269 (1991).
George, et al., "Initial Results of Phase 1 Study of DCC-2618, a Broad-Spectrum Kit and PDGFRA Inhibitor, in Patients (PTS) with Gastrointestinal Stromal Tumor (GIST) by Number of Prior Regimes", European Society for Medical Oncology, 1-13 (2018).
Gishizky, et al., "Efficient transplantation of BCR-ABL-induced Chronic Myelogenous Leukemia-like Syndrome in Mice," Proc. Natl. Acad. Sci. (Apr. 1993) vol. 90, pp. 3755-3759.
Gorre et al., "Clinical Resistance to STI-571 Cancer Therapy Caused by BCR-ABL Gene Mutation or Amplification," Science (Aug. 3, 2001) vol. 293, pp. 876-880.
Greene, et al., "Chapter 7: Protection for the Amino Group", in Protective Groups in Organic Synthesis, Third Edition, pp. 494-653 (1999).
Griffith, et al., "TPAP: Tetra-n-propylammonium Perruthenate, A Mild and Convenient Oxidant for Alcohols", Aldrichimica Acta, 23(1):13-19 (1990).
Guzel, "Investigation of the Relationship Between the Inhibitory Activity of Glycolic Acid Oxidase (GAO) and its Chemical Structure: Electron-Topological Approach", Journal of Molecular Structure, 366:131-137 (1996).
Haar, et al., "Structure of GSK313 Reveals a Primed Phosphorylation Mechanism", Nature Structural Bioloav, 8(7):593-596 (2001).
Hackler, et al., "The Syntheses of 5-Amino-3- t-butylisothiazole and 3-Amino-5- t-butylisothiazole," J. Heterocyclic Chem. (Nov.-Dec. 1989) vol. 26, pp. 1575-1578.
Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).
Hearing Notice in Indian Patent App. No. 11241/DELNP/2014 mailed Jan. 24, 2020.
Heegaard, et al., "Affinity Capillary Electrophoresis: Important Application Areas and Some Recent Developments", Journal of Chromatography B, 715:29-54 (1998).

(56) References Cited

OTHER PUBLICATIONS

Heinrich, et al., "Molecular Correlates of Imatinib Resistance in Gastrointestinal Stromal Tumors," Journal of Clinical Oncology, 24(29):4764-4774 (2006).
Heinrich, et al., "Primary and Secondary Kinase Genotypes Correlate With the Biological and Clinical Activity of Sunitinib in Imatinib-Resistant Gastrointestinal Stromal Tumor," Journal of Clinical Oncology, 26(33):5352-5359 (2008).
Honda, et al., "Determination of the Association Constant of Monovalent Mode Protein-Sugar Interaction by Capillary Zone Electrophoresis", Journal of Chromatography, 597:377-382 (1992).
Hu, et al., "Capillary Electrophoresis for the Analysis of Biopolymers", Anal., Chem., 74:2833-2850 (2002).
Huang, et al., "Inhibition of Nucleoside Transport by Protein Kinase Inhibitors", The Journal of Pharmacolo and Experimental Therapeutics, 304 2 :753-760 (2003).
Hubbard, "Crystal Structure of the Activated Insulin Receptor Tyrosine Kinase in Complex with Peptide Substrate and ATP Analo ", EMBO, 16(18):5573-5581 (1997).
Hubbard, et al., "Crystal Structure of the Tyrosine Kinase Domain of the Human Insulin Receptor", Nature, 374:746-754 (1994).
Hughes, et al., "Modulation of the Glycogen Synthase Kinase-3 Family by Tyrosine Phosphor lation", EMBO, 12 2 :803-808 (1993).
Huse et al., "The Conformational Plasticity of Protein Kinases," Cell (May 3, 2002) vol. 109, pp. 275-282.
Huse, et al., "Crystal Structure of the Cytoplasmic Domain of the Type I TGFl3 Receptor in Complex with FKBP12", Cell, 96:425-436 (1999).
Huse, et al., "The TGFl3 Receptor Activation Process: An Inhibitor-to Substrate-Binding Switch", Molecular Cell, 8:671-682 (2001).
Igarashi, et al., "Antimicrobial Activities of 2-arylthio-N-alkylmaleimides", Journal of Industrial Microbiolo, 9:91-96 (1992).
International Human Genome Sequencing Consortium, "Initial Sequencing and Analysis of the Human Genome", Nature, 409:860-921 (2001).
International Search Report and Written Opinion from PCT/US2012/041378, dated Sep. 17, 2012.
International Search Report and Written Opinion from PCT/US2017/035005, dated Feb. 22, 2018.
International Search Report and Written Opinion from PCT/US2019/016148, dated Apr. 17, 2019.
International Search Report and Written Opinion from PCT/US2019/016161, dated Apr. 23, 2019.
International Search Report and Written Opinion from PCT/US2020/045876, dated Oct. 22, 2020.
International Search Report and Written Opinion from PCT/US2020/067557, dated Apr. 23, 2021.
International Search Report and Written Opinion from PCT/US2020/067560, dated Apr. 23, 2021.
International Search Report and Written Opinion from WO2008/034008 A3, dated Apr. 11, 2008.
International Search Report issued for PCT/US2008/060833, dated Sep. 30, 2008.
International Search Report issued for PCT/US2008/060867, dated Sep. 29, 2008.
International Search Report issued for PCT/US2008/060896, dated Sep. 29, 2008.
Ishida, et al., "Molecular Arrangement and Electrical Conduction of Self-Assembled Monola ers Made from Terphen I Thiols", Surface Sciences, 514:187-193 (2002).
Islip, et al., "Nitrofuryl Heterocyclics 3", Journal of Medicinal Chemistry, 16(11):1309-1310 (1973).
Jackson, et al., "N-Terminal Mutations Activate the Leukemogenic Potential of the M risto lated form of c-abl", EMBO, 8(2):449-456 (1989).
Jackson, et al., "Pyridinylimidazole Based p38 MAP Kinase Inhibitors", Current Topics in Medicinal Chemist, 2:1011-1020 (2002).

Janku F et al., "DCC-2618, a pan KIT and PDGFR switch control inhibitor, achieves proof-of-concept in a first-in-human study," Late Breaking Abstracts, Plenary Session 6, Dec. 1, 2016, p. s4.
Janku Filip et al., "Pharmacokinetic-driven phase I study of DCC-2618 a pan-KIT and PDGFR inhibitor in patients (pts) with gastrointestinal stromal tumor (GIST) and other solid tumors," J. Clin. Oncol. (2017) No. 15, Suppl 2515.
Janku, et al., "Abstract CT058: Ripretinib (DCC-2618) pharmacokinetics (PK) in a Phase I study in patients with gastrointestinal stromal tumors (GIST) and other advanced malignancies: A retrospective evaluation of the PK effects of proton pump inhibitors (PPIs)", American Association for Cancer Research, 79(13):1-4 (2019).
Jiang, et al., ""Soft Docking": Matching of Molecular Surface Cubes", J. Mol. Biol., 219:79-102 (1991).
Jiang, et al., "Synthesis and SAR Investigations for Novel Melanin-Concentrating Hormone 1 Receptor (MCH1) Antagonists Part 1. The Discovery of Arylacetamides as Viable Replacements for the Dihydropyrimidione Moiety of an HTS Hit", J. Med. Chem., 50:3870-3882 (2007).
Johnson, "Circular Dichroism Spectroscopy and The Vacuum Ultraviolet Region", Ann. Rev. Phys. Chem., 29:93-114 (1978).
Johnson, "Protein Secondary Structure and Circular Dichroism: A Practical Guide", PROTEINS: Structure, Function, and Genetics, 7:205-214 (1990).
Johnson, et al., "An Evaluation of the Effect of Light Stabilisers on the Exterior Durability of Polyester Powder Coatings for the Architectural Market", Surface Coatings International, 3:134-141 (1999).
Johnson, et al., "The Stereochemistry of Oxidation at Sulfur Oxidation of 2-Thiabicyclo[2.2.1]Hpetane", Tetrahedron, 25:5649-5653 (1969).
Katritzky, et al., "Novel Chromophoric Heterocycles Based on Maleimide and Naphthoquinone", J. Heterocyclic Chem., 26:885-892 (1989).
Kern, et al., "Synthese von Makromolekeln einheitlicher Brol3e. Il Mitt: Syntheses neuer Diololigo-urethane nach dem Duplikationsverfahren", Makromolekulara Chemie, 16:89-107 (1955).
Kettle et al., "Discovery of N-(4-{[5-Fluoro-7-(2-methoxyethoxy)quinazolin-4-yl]amino}phenyl)-2-[4-(propan-2-yl)-1H-1,2,3-triazol-1-yl]acetamide (AZD3229), a Potent Pan-KIT Mutant Inhibitor for the Treatment of Gastrointestinal Stromal Tumors" Journal of Medicinal Chemistry (2018), 61(19), 8797-8810.
Kim, et al., "Solid Phase Synthesis of Benzamidine and Butylamine-Derived Hydantoin Libraries", Molecular Diversity, 3:129-132 (1998).
Klayman, et al., "The Reaction of S-Methiodide Derivatives of Activated Thioureas with Hydroxylic Compounds. A Novel Synthesis of Mercaptans", J. Org. Chem., 37(10):1532-1537 (1972).
Kleywegt, et al., "Detection, Delineation, Measurement and Display of Cavities in Macromolecular Structures", Acta Cryst, D50:178-185 (1994).
Koch, et al., "QSAR and Molecular Modelling for a Series of Isomeric X-Sulfanilamido-1-phenylpyrazoles", Quant. Struct. Act. Relat., 12:373-382 (1993).
Kolch, W., "Meaningful relationships: the regulation of the Ras/Raf/MEKJERK pathway by protein interactions," Biochern. J (2000) 351: 289-305.
Konopka, et al., "Cell Lines and Clinical Isolates Derived From Ph-positive Chronic Myelogenous Leukemia Patients Express c-abl Proteins With a Common Structural Alteration," Proc. Natl. Acad. Sci. (Mar. 1985) vol. 82, pp. 1810-1814.
Krasovitskii, et al., "Synthesis and Spectral-Luminescence Properties of Hetarylethylene Derivatives of 2,5-Diphenyloxazole and 2,5-Diphenyl-1,3,4-Oxadiazole", Khimiya Geterotsikllicheskikh Soedinenii, 5:617-621 (1982).
Kuhn, et al., "The Genesis of High-Throughput Structure-Based Drug Discovery using Protein Crystallography", Analytical Techniques, Current Opinion in Chemical Biology, 6:704-710 (2002).
Kumar, et al., "P38 Map Kinases: Key Signalling Molecules as Therapeutic Targets for Inflammatory Diseases", Nature Reviews Drug Discovery, 2:717-726 (2003).
Kundrot, "Which Strategy for a Protein Crystallization Project", CMLS, Cell. Mol. Life Sci., 61:525-536 (2004).
Kundu, et al., "Depropargylation Under Palladium-Copper Catatlysis: Synthesis of Diaryl Sulfides", Tetrahedron, 57:5885-5895 (2001).

(56) References Cited

OTHER PUBLICATIONS

Kurogi, et al., "Discovery of Novel Mesangial Cell Proliferation Inhibitors Using a Three-Dimensional Database Searchinq Method", J. Med. Chem., 44:2304-2307 (2001).

Kuse, et al., Synthesis of azide-fluoro-dehydrocoelentcrazine analog as a photoaffinitylabeling probe and photolysis of azide-fluorocoelenterazine; Tetrahedron Lett. (2005) 61:5754-5762.

Kwong, et al., "A General, Efficient, and Inexpensive Catalyst System for the Coupling Aryl lodides and Thiols", Organic Letters, 4(20):3517-3520 (2002).

Laskowski, "SURFNET: A Program for Visualizing Molecular Surfaces, Cavities, and Intermolecular Interactions", Journal of Molecular Graphics, 13:323-330 (1995).

Leca, et al., "A New Practical One-Pot Access to Sulfonimidates", Organic Letters, 4(23):4093-4095 (2002).

Lefevre, et al., "Roles of Stem Cell Factor/c-Kit and Effects of Glivec@/STI571 in Human Uveal Melanoma Cell Turmorigenesis", Journal of Biological Chemistry, 279(30):31769-31779 (2004).

Lesort, et al., "Insulin Transiently Increases Tau Phosphorylation: Involvement of Glycogen Synthase Kinase-3f3 and Fyn Tyrosine Kinase", Journal of Neurochemistry, 72(2):576-584 (1999).

Leung, et al., "The Difluoromethylensulfonic Acid Groups as a Monoanionic Phosphate Surrogate for Obtaining PTP1 B Inhibitors", Bioorganic & Medicinal Chemistry, 10:2309-2323 (2002).

Li, et al., "Targeting Serine/Threonine Protein Kinase B/Akt and Cell-cycle Checkpoint Kinases for Treating Cancer", Current Topics in Medicinal Chemistry, 2:939-971 (2002).

Li, et al., "The P190, {210, and P230 Forms of the BCR/ABL Oncogene Induce a Similar Chronic Myeloid Leukemia-like Syndrome in Mice but Have Different Lymphoid Leukemogenic Activity", J. Exp. Med., 189(9):1399-1412 (1999).

Lim et al., "Current research and treatment for gastrointestinal stromal tumors" World Journal of Gastroenterology (2017), 23(27), 4856-4866 Publisher: Baishideng Publishing Group Inc.

Link, et al., "Synthesis of 8-Substituted 5-Deazaflavins", J. Heterocyclic Chem, 22:841-848 (1985).

Lipinski, et al., "Experimental and Computational Approaches to Estimate Solubility and Permeability in Drug Discovery and Development Settings", Advanced Drug Delivery Reviews, 23:3-25 (1997).

Longley et al., "Somatic c-KIT activating mutation in urticaria pigmentosa and aggressive mastocytosis: establishment of clonality in a human mast cell neoplasm," Nature Genetics, 12(3):312-314 (1996).

Loren, et al., "NH-1,2,3-Triazoles from Azidomethyl Pivalate and Carbamates: Base-Labile N-Protecting Groups", SYNLETT, 18:2847-2850 (2005).

Lorenzi, et al., "Amino Acid Ester Prodrugs of 2-Bromo-5, 6-dichloro-1-([3-D-ribofuranosyl)benzimidazole Enhance Metabolic Stability In Vitro and In Vivo," The Journal of Phannaco/ogy and Experimental Therapeutics (2005) vol. 314, No. 2 pp. 883-890.

Lowinger, et al., "Design and Discovery of Small Molecules Targeting Raf-1 Kinase", Current Pharmaceutical Design, 8:2269-2278 (2002).

Lu Jiade et al., "Advanced in the targeted therapy of cancer: multi targeted Raf kinase inhibitor," China Oncology, vol. 17, No. 1, (Dec. 31, 2007), pp. 1-7.

Ma, et al., "C-MET Mutational Analysis in Small Cell Lung Cancer: Novel Juxtamembrane Domain Mutations Regulating Cytoskeletal Functions", Cancer Research, 63:6272-6281 (2003).

Ma, et al., "C-Met: Structure, Functions and Potential for Therapeutic Inhibition", Cancer and Metastasis Reviews, 22:309-325 (2003).

Magnuson, et al., "The Raf-I serine/threonine protein kinase," Seminars in Cancer Biology. (1994) 5: 247-253.

Mallakpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).

Mamaev, et al., "Synthesis of 2,5'-Bipyrimidines from Substituted 5-Cyanopyrimidines", Khimiya Geterotsiklicheskikh Soedinenni, 24(3):371-375- (1988).

March's Advanced Organic Chemisto.:: Reactions Mechanisms and Structure Fifth Edition, Smith and March Editors, Wiley-Interscience Publication (2001).

March, et al., "Tautomerism", from March's Advanced Organic Chemisto.::, 4th Edition, WileyInterscience, pp. 69-74.

Martinez, et al., "First Non-ATP Competitive Glycogen Synthase Kinase 313 (GSK-313) Inhibitors: Thiadizolidinones (TDZD) as Potential Drugs for the Treatment of Alzheimers Disease", J. Med. Chem., 45(2002)1292-1299 (2002).

Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunoloav, pp. 4170-4177 (2000).

Mazzieri, R et al., Targeting The ANG2/TIE2 Axis Inhibits Tumor Growth and Metastasis by impairing Angiogenesis and Disabling Rebounds of Proangiogenic Myelid Cells. Cell. Apr. 12, 2001, vol. 19, pp. 512-526; DOI: 10.1016/j.ccr.2001.02.005.

McPherson, "Current Approaches to Macromolecular Crystallization", Eur. J. Biochem., 189:1-23 (1990).

Medebielle, et al., "A Convenient Synthesis of Perfluoroalkylated and Fluorinated-Aryl Nitrogen Bases by Electrochemically Induced SRN1 Substitution", J. Org. Chem., 61:1331- 1340 (1996).

Medebielle, et al., "A New Convenient Synthesis of 5-Aryl Uracils Using SRN1 Aromatic Nucleophilic Substitution", Tetrahedron Letters, 34(21 ):3409-3412 (1993).

Mikhaleva, et al., "Relative Reactivities of the Chlorine Atoms of 2,2',4-Trichloro-4',5-Dipyrimidinyl in its Reaction with Piperidine", Khimiya Geterotsiklicheskikh Soedinenii, 6:821-826 (1979).

Mol, "Structural Basis for the Autoinhibition and STI-571 Inhibition of c-Kit Tyrosine Kinase," The Journal Of Biological Chemistry, 279(30):31655-31663 (2004).

Morris, et al., "Automated Docking of Flexible Ligands to Macromolecules", AutoDock Website, www.scripps.edu/mb/olson/doc/autodock/, printed Mar. 3, 2005.

Morris, et al., "Automated Docking Using a Lamarckian Genetic Algorithm and an Empirical Binding Free Energy Function", Journal of Computational Chemistry, 19(14):1639-1662 (1998).

Morstyn, et al., "Stem Cell Factor Is a Potent Synergistic Factor in Hematopoiesis", Oncology, 51:205-214 (1994).

Moss, et al., Basic Terminology of Stereochemistry, Pure & Appl. Chem., 6812):2193-2222 (1996).

Muller, "Glossary of Terms Used in Physical Organic Chemistry", Pure & Appl. Chem., 66(5):1077-1184 (1994).

Muller, et al., "A General Synthesis of 4-Substituted 1,1-Dioxo-1,2,5-thiadiazolidin-3-ones Derived from α-Amino Acids", J. Org. Chem., 54:4471-473 (1989).

Murayama, et al., "JNK (c-Jun NH2 Terminal Kinase) and p38 During Ischemia Reperfusion Injury in the Small Intestine" Transplantation, 81(9):1325-1330 (2006).

Mutlib, et al., "Disposition of 1-[3-(Aminomethyl)phenyl]-N-[3-fluoro-2'-(methylsulfonyl)-[1, 1 '-biphenyl]-4-yl]-3(trifluomethyl)-1 H-pyrazole-5-carboxamide (DPC 423) by Novel Metabolic Pathways. Characterization of Unusual Metabolites by Liquid Chromatography/Mass Spectrometrv and NMR", Chem. Res. Toxicol., 15:48-62 (2002).

Mutlib, et al., "P450-Mediated Metabolism of 1-[3-(Aminomethyl)phenyl]-N-[3-fluoro-2'- (methylsulfonyl)-[1, 1 '-biphenyl]-4-yl]-3(trifluomethyl)-1 H-pyrazole-5-carboxamide (DCP 423) and Its Analogues to Aldoximes. Characterization of Glutathione Conjugates of Postulated Intermediates Derived from Aloximes", Chem. Res. Toxicol., 15:63-75 (2002).

Nagano, M. et al. "Studies on Organic Sulfur Compounds. XIV. The Reaction of N-alkoxy-carbonyl-N'-(2-thiazolyl)thioureas with some oxidants." Chemical and Pharmaceutical Bulletin. vol. 21, No. 11, pp. 2408-2416. ISSN: 0009-2363. Nov. 1973.

Nagar, et al., "Crystal Structures of the Kinase Domain of c-Abl in Complex with the Small Molecule Inhibitors PD173955 and Imatinib (STI-571)", Cancer Research, 62:4236-4243 (2002).

Nagata, et al., "Identification of a point mutation in the catalytic domain of the protooncogene c-kit in peripheral blood mononuclear

(56) References Cited

OTHER PUBLICATIONS cells of patients who have mastocytosis with an associated hematologic disorder," Proc. Natl. Acad. Sci. USA, 92(23):10560-10564 (1995).
Nager, et al., "Structural Basis for the Autoinhibition of c-Abl Tyrosine Kinase," Cell (Mar. 21, 2003) vol. 112, pp. 859-871.
Nakopoulou, et al., "c-Met Tyrosine Kinase Receptor Expression is Associated with Abnormal !3-catenin Expression and Favourable Prognostic Factors in Invasive Breast Carcinoma", Histopatholoav, 36:313-325 (2000).
Nantaka-Namirski, et al., "Condensation Reaction of Ethyl (4-Uracil)-Acetate with Ethyl Orthoformate", ACTA Polon. Pharm XXVII, 28(5):455-463 (1971).
National Academy of Sciences, "Abstracts of Papers Presented at the Autumn Meetinq, Nov. 14-16, 1960", Science, 132:1488-1501 (1960).
Nicolaou, et al., "Molecular Design and Chemical Synthesis of a Highly Potent Epothilone", ChemMedChem, 1:41-44 (2006).
Nikolaev, et al., "Solubility Polytherm in the System HNO3-H2O-(C4H9O)PO(C4H9)2", Dokladv Akademii Nauk SSSR, 160(4):841-844 (1965).
Ning, et al., "Activating Mutations of c-Kit at Codon 816 Confer Drug Resistance in Human Leukemia Cells," Leukemia and Lymphoma, 41(5-6):513-522 (2001).
Nofal, et al., "Synthesis of Novel Uracil-5-Sulphonamide Derivatives of Possible Biological Activity", Egypt J. Chem., 33(4):375-380 (1990).
Nowell et al., "A Minute Chromosome in Human Chronic Granulocytic Leukemia," Science (Nov. 18, 1960) vol. 132, p. 1497.
O'Dell, et al., "Treatment of Rheumatoid Arthritis with Methotrexate Alone, Sulfasalazine and Hydroxychloroquine, or a Combination of All Three Medications", New England J. Med., 334(20):1287-1291(1996).
O'Neill, "Targeting Signal Transduction as a Strategy to Treat Inflammatory Diseases", Nature Review Drug Discovery, Published Online Jun. 9, 2006, www.nature.com/reviews/druqdisc.
Office Action of U.S. Appl. No. 17/180,234 dated Apr. 29, 2021, 6 pages.
Office Action of U.S. Appl. No. 17/180,241 dated Aug. 20, 2021, 11 pages.
Office Action of U.S. Appl. No. 17/180,241 dated May 7, 2021, 9 pages.
Okano, et al., "o-Bromophenylzinc Compound: A Readily Available and Efficient Synthetic Equivalent of o-Phenylene 1-Anion 2-Cation", Tetrahedron Letters 39:3001-3004 (1998).
Okishio, et al., "Differential Ligand Recognition by the Src and Phosphatidylinositol 3-Kinase Src Homology 3 Domains: Circular Dichroism and Ultraviolet Resonance Raman Studies", Biochemistrv, 42:208-216 (2003).
Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistrv, 40:15797-15804 (2001).
Okishio, et al., "Role of the Conserved Acidic Residue Asp21 in the Structure of Phosphatidylinositol 3-Kinase Src Homolgy 3 Domain: Circular Dichroism and Nuclear Maqnetic Resonance Studies", Biochemistrv 40:119-129 (2001).
Okram, Barun et al: "A General Strategy for Creating "Inactive-Conformation" Ab1 Inhibitors" Chemistry&Biology (Cambridge, MA, US), 13(7), 779-786 CODEN: CBOLE2; ISSN: 1074-5521, 2006, XP002469183 table 1 the whole document.
Palmer, Brian, D. et al: "Structure-Activity Relationships for 2-Anilino-6-Phenylpyrido[2,3-d]Pyrimidin-7(8H)-Ones as Inhibitors of the Cellular Checkpoint Kinase Wee1" Bioorganic & Medicinal Chemistry Letters, 15(7), 1931-1935 CODEN: BMCLE8; ISSN: 0960-894X, 2005, XP004789411 p. 1933.
Parang, et al., "Mechanism-based Design of a Protein Kinase Inhibitor", Nature Structural Bioloav, 8( 1 ):37-41 (2001).

Pargellis, et al., "Inhibition of p38 MAP Kinase by Utilizing a Novel Allosteric Binding Site", Nature Structural Bioloav, 9(4 ):268-272 (2002).
Park, et al., "Mechanism of met Oncogene Activation", Cell, 45:895-904 (1986).
Pearlman, et al., "Assisted Model Building with Energy Refinement", Amber Home Page, amber.scripts.edu.
Pedersen, "The Preparation of Some N-Methyl-1,2,3-Triazoles", Acta Chimica Scandinavica, 13(5):888-892 (1959).
Peng, et al., "Identification of Novel Inhibitors of BCR-ABL Tyrosine Kinase via Virtual Screening", Bioorganic & Medicinal Chemistry Letters, 13:3693-3699 (2003).
Pereira, et al., "The Role of c-kit and Imatinib Mesylate in Uveal Melanoma", Journal of Carcinogenesis, 4:19 (2005), downloaded from www.carcinogenesis.com/content/4/1/19, Sep. 3, 2008.
Peyssonnaux, C et al., "The RaflMEK/ERK pathway: new concepts of activation," Biol. Cell (2001) 93: 53-62.
Picard, et al., Inhibitors of Acyl-CoA: Cholesterol O-Acyltrasferase. 17. Structure-Activity Relationships of Several Series of Compounds.
Pierrat, et al., "Solid Phase Synthesis of Pyridine-Based Derivatives from a 2-Chloro-5-Bromopyridine Scaffold," J Comb. Chem. (2005) 7 (6): 879-886.
Pluk et al., "Autoinhibition of c-Abl," Cell (Jan. 25, 2002) vol. 108, pp. 247-259.
Ponzetto, et al., "A Novel Recognition Motif for Phosphatidylinositol 3-Kinase Binding Mediates Its Association with the Hepatocyte Growth Factor/Scatter Factor Receptor", Molecular and Cellular Bioloav, 13(8):4600-4608 (1993).
Procenko, S.A., "Targeted Therapy in Melanoma, Gastrointestinal Stromal Tumors, Dermatofibrosarcoma Protuberans", Practical Oncology, vol. 11, No. 3, https://practical-oncology.ru/articles/196.pdf, (2010), pp. 162-170.
Raimbaul T, et al., "Effects of pH and KCl on the Conformations of Creatine Kinase from Rabbit Muscle", Eur. J. Biochem., 234:570-578 (1995).
Ranatunge, et al, "Synthesis and Selective Cyclooxygenase-2 Inhibitory Activity of a Series of Novel, Nitric Oxide Donor-Containing Pyrazoles," J Med Chem. (2004) 47: 2180-2193.
Reardon, D. et al., "Effect of CYP3A-inducing anti-epileptics on sorafenib exposure: results of a phase II study of sorafenib plus daily temozolomide in adults with recurrent gliosblastoma", J. Neurooncol. (2011), 101: pp. 57-66.
Rebek, et al. "Convergent Functional Groups: Synthetic and Structural Studies", J. Am. Chem. Soc., 107:7476-7481 (1985).
Rebek, et al., "Convergent Functional Groups. 2. Structure and Selectivity in Olefin Epoxidation with Peracids", J. Org. Chem., 51:1649-1653 (1986).
Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).
Regan, et al., "Pyrazole Urea-Based Inhibitors of p38 MAP Kinase: From Lead Compound to Clinical Candidate", J. Med. Chem., 45:2994-3008 (2002).
Regan, et al., "Structure-Activity Relationships of the p38a MAP Kinase Inhibitor 1-(5-tert-Butyl-2-p-tolyl-2H-pyrazol-3-yl )-3-[4-(2-morpholi n-4-yl-ethoxy)naph-thalen-1-yl]urea (BI RB 796)", J. Med. Chem., 46:4676-4686 (2003).
Reis, R. et al., "Molecular characterization of PDGFR-α/PDGF-A and c-KIT/SCF in gliosarcomas", Cellular Oncology, 2005; 27: pp. 319-326.
Remington, The Science and Practice of Pharmacy, Nineteenth Edition—1995, pp. 710-712.
Response to Office Action of U.S. Appl. No. 14/351,840 dated Sep. 28, 2015, 11 pages.
Rooney, et al., "Inhibitors of Gylcolic Acid Oxidase. 4-Substituted 3-Hydroxy-1 H-pyrrole-2,5-dione Derivatives", J. Med. Chem., 26(5):700-714 (1983).
Roux, et al., "ERK and p38 MAPK-Activated Protein Kinases: a Family of Protein Kinases with Diverse Biological Functions", Microbiology and Molecular Biology Reviews, 68(2):320-344 (2004).

(56) References Cited

OTHER PUBLICATIONS

Rowley, "A New Consistent Chromosomal Abnormality in Chronic Myelogenous Leukaemia identified by Quinacrine Flourescence and Giemsa Staining," Nature (Jun. 1, 1973) vol. 243, pp. 290-293.
Rubin, et al., "Gastrointestinal stromal tumour," The Lancet Oncology, 369(9574):1731-1741 (2007).
Russell, et al., "3-[3-(Piperdin-1-yl)propyl]indoles as Highly Selective h5-HT1D Receptor", J. Med. Chem., 42:4981-5001 (1999).
Rutkowski, et al., "Gastrointestinal stromal tumours (GIST)—2018", Oncology in Clinical Practice, 14(6):399-407 (2019).
Saiga, et al., "Consecutive Cross-Coupling of o-Phenylenedizinc Compound with Acyl and/or Aryl Halides in the Presence of Pd(0)-tris(2,4,6-trimethoxyphenyl)phosphine", Tetrahedron Letters, 41:4629-4632 (2000).
Sakamoto, et al., "Condensed Heteroaromatic Ring Systems. XIX. Synthesis and Reactions of 5-(Tributylstannyl)Isoxazoles", Tetrahedron, 4 7(28):5111-5118 (1991).
Sakuma, et al., "C-kit Gene Mutations in Intracranial Germinomas", Cancer Sci, 95(9):716-720 (2004).
Salgia, "Studies on c-Kit and c-Met in Lung Cancer with Similarities to Stem Cells," Microscopy Society of America, 11(2):1-30 (2005).
Satsangi, et al., "1-(4-Substituted-thiazol-2-yl)hydatoins as Antiinflammatory and CNS- Active Agents", Pharmazie, 38:341-342 (1983).
Sawyers, "Chronic Myeloid Leukemia," *The New England Journal of Medicine* (Apr. 29, 1999) vol. 340, No. 17, pp. 1330-1340.
Schindler et al., "Structural Mechanism for STI-571 Inhibition of Abelson Tyrosine Kinase," Science (Sep. 15, 2000) vol. 289, pp. 1938-1942.
Schlosser, et al., "Regiochemically Flexible Substitutions of Di-, Tri-, and Tetrahalopy:ridines: The Trialkylsily Trick," J Org. Chem. (2005) 70: 2494-2502.
Schmidt, et al., "Germline and Somatic Mutations in the Tyrosine Kinase Domain of the MET proto-oncogene in Papillary Renal Carcinomas", Nature Genetics, 16:68-73 (1997).
Schmidt, et al., "Novel Mutations of the MET Proto-oncogene in Papillary Renal Carcinomas", Oncoqene, 18:2343-2350 (1999).
Schnessweiss Mathias, et al., "The KIT and PDGFRA switchcontrol inhibitor DCC-2618 blocks growth and survival of multiple neoplastic cell types in advanced mastocytosis," *Haematologica* (2018) vol. 103, No. 5, pp. 799-809.
Schneeweiss Mathias, et al., "The Multi-Kinase Inhibitor DCC-2618 Inhibits Proliferation and Survival of Neoplastic Mast Cells and Other Cell Types Involved in Systemic Mastocytosis," Blood (2016) vol. 128, No. 22, pp. 1965.
Seimiya, et al., "Telomere Shortening and Growth Inhibition of Human Cancer Cells by Novel Synthetic Telomerase Inhibitors MST-312, MST-295, and MST-199", Molecular Cancer Therapeutics, 1:657-665 (2002).
Seminario, et al., "Theoretical Study of a Molecular Resonant Tunneling Diode", J. Am. Chem. Soc., 122:3015-3020 (2000).
Seto, et al. "2-Substituted-4-aryl-6, 7 ,8,9-tetrahydro-5/ 1-p)'Timido [ 4, 5-b] [ 1,5 Joxazocin-5-oneasastructurallynewNK1 antagonist," Biorg Nied Chem. Tea. (2005) 15: 1485-1488.
Shah et al., "Overriding Imatinib Resistance with a Novel ABL Kinase Inhibitor," Science (Jul. 16. 2004) vol. 305, pp. 399-401.
Shah, et al., "Circular Dichroic Studies of Protein Kinase C and its Interactions with Calcium and Lipid Vesicles", Biochimica et Biophvsica Acta, 1119:19-26 (1992).
Shi, et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bull. Chem. Soc. Jpn., 65:3315-3321 (1992).
Shinkai, et al., "Coenzyme Models, Part 45. Synthesis of Atropisomeric Flavins and their Novel Redox-induced Racemisation", J. Chem. Soc. Perkin Trans., pp. 313-319 (1988).

Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).
Sihto, et al., "KIT and Platelet-Derived Growth Factor Receptor Alpha Tyrosine Kinase Gene 1-30 Mutations and KIT Amplifications in Human Solid Tumors," Journal of Clinical Oncology, 23(1):49-57 (2005).
Sircar et al., "Synthesis of 4-Hydroxy-N-[5-(hydroxymethyl)-3-isoxazolyI]2-methyl-2H-1,2-bsnzo-thiazine-3-carboxamide 1,1-Dioxide and [(5-Methyl-3-isoxazolyl)amino]oxoacetic Acid. Major Metabolites of Isoxicam," *J. Org. Chem.* (1985) vol. 50, pp. 5723-5727.
Smith et al., "Ripretinib (DCC-2618) is a switch control kinase inhibitor of a broad spectrum of oncogenic and drug-resistant KIT and PDGFRA variants," *Cancer Cell* (2019), vol. 35, No. 5, pp. 738-759.
STN Registry Database RN 1225278-16-9.
Stout, et al., "High-Throughput Structural Biology in Drug Discovery: Protein Kinases", Current Pharmaceutical Design, 10:1069-1082 (2004).
Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).
Szucs, Z. et al., "Promising novel therapeutic approaches in the management of gastrointestinal stromal tumors", Future Oncology, (2017), vol. 13(2), pp. 185-194.
Tanis, et al., "Two Distinct Phosphorylation Pathways Have Additive Effects on Abl Family Kinase Activation", Molecular and Cellular Bioloav, 23(11 ):3884-3896 (2003).
Tanno, F. et al., "Evaluation of Hypromellose Acetate Succinate (HPMCAS) as a Carrier in Solid Dispersions", Journal of Drug Development and Industrial Pharmacy, vol. 30, No. 1, pp. 9-17 (2004).
Tarn, et al., "Analysis of KIT Mutations in Sporadic and Familial Gastrointestinal Stromal Tumors: Therapeutic Implications through Protein Modeling," Clinical cancer research : an official journal of the American Association for Cancer Research, 11(10):3668-3677 (2005).
Teague, "Implications of Protein Flexibility for Drug Discovery", Nature Reviews, 2:527-541 (2003).
Tian, et al., "Activating c-kit Gene Mutations in Human Germ Cell Tumors," American Journal of Pathology, 154(6):1643-1647 (1999).
Tominaga, et al., "General model for Estimation of the Inhibition of Protein Kinases Using Monte Carlo Simulations", J. Med. Chem., 47:2534-2549 (2004).
Tremblay, et al., "Efficient Solid-Phase Synthesis of Sulfahydantoins", J. Comb. Chem., 4:429-435 (2002).
Tsuzuki, et al., "Synthesis and Structure-Activity Relationships of Novel ?—Substituted 1,4-Dihydro-4-oxo-1-(2-thiazolyl)-1,8-napthyridine-3-carboxylic Acids as Antitumor Agents. Part 2", J. Med. Chem., 47:2097-2109 (2004).
Van Etten, "Cycling, Stressed-out and Nervous: Ceiiuiar Functions of c-Abi," Trends in Cell Biology (May 1999) vol. 9, pp. 179-186.
Venter, et al., "The Sequence of the Human Genome", Science, 291:1304-1351, Feb. 16, 2001; Erratum, Jun. 8, 2001.
Vladimirova, L.U., "Usage of MEK Inhibitors in Oncology: Results and Perspectives", Modern Natural Science Successes, No. 3, https://s.natural-sciences.m/pdf/2015/3/34730.pdf., (2015), pp. 18-30.
Von Bubnoff, et al., "BCR-ABL gene mutations in relation to clinical resistance of Philadelphia-chromosome-positive leukemia to STI571. a prospective study," The Lancet (Feb. 9, 2002) vol. 359, pp. 487-491.
Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).
Wan et al., "Mechanism of Activation of the RAF-ERK Signaling Pathway by Oncogenic Mutations of B-RAF," *Cell* (Mar. 19, 2004) vol. 116. pp. 855-867.
Wardelmann, "Acquired resistance to imatinib in gastrointestinal stromal tumours caused by multiple KIT mutations," The Lancet Oncology, 6(4):249-251 (2005).

(56) References Cited

OTHER PUBLICATIONS

Welker, et al., "Glucocorticoid-Induced Modulation of Cytokine Secretion from Normal and Leukemic Human Myelomonocytic Cells", Int. Arch. Allergy Immunol, 109:110-115 (1996).
Wentland, et al., "3-Quinolinecarboxamides. A Series of Novel Orally-Active Antiherpetic Agents", J. Med. Chem., 36:1580-1596 (1993).
Wilson, et al., "The Structural Basis for the Specificity of Pyridinylimidazole Inhibitors of p38 MAP Kinase", Chemistry & Biology, 4(6):423-431 (1997).
Wilson, et el., "Laser-Jet Delayed Trapping: Electron-Transfer Trapping of the Photoenol from 2-Methylbenzophenone", J. Am. Chem. Soc., 109:4743-4745 (1987).
Wolter, et al., "Copper-Catalyzed Coupling of Aryl Iodides with Aliphatic Alcohols", Organic Letters, 4(6):973-976 (2002).
Wrana, et al., "Mechanism of Activation of the TGF-B Receptor", Nature, 370:341-347 (1994).
Wu, et al., "Discovery of a Novel Family of CDK Inhibitors with the Program LIDAEUS:Structual Basis for Ligand-Induced Disordering of the Acivation Loop", Structure, 11:399-410 (2003).
Yang, et al., "Molecular Mechanism for the Regulation of Protein Kinase B/Akt by Hvdrophobic Motif Phosphorylation", Molecular Cell, 9:1227-1240 (2002).
Yang, et al., "Palladium-Catalyzed Amination of Arly Halides and Sulfonates", Journal of Organometallic Chemistry, 576:125-146 (1999).
Yarden, et al., "Human Proto-oncogene c-kit: a New Cell Surface Receptor Tyrosine Kinase for an Unidentified Ligand", The EMBO Journal, 6(11):3341-3351 (1987).
Yoneda, et al., "A New Synthesis of Purines", J.C.S. Chem. Comm., pq. 551 (1974).
Yonezawa, et al., "Synthesis of Sequentially Controlled Isomeric, Wholly aromatic Polyketones Composed of 2-trifluoromethylbiphenylene and 2,2'-dimethoxybiphenylene Units", Reactive & Functional Polymers, 52:19-30 (2002).
Yoshimoto, et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Dehydrogenase, Glutamate Dehydrogenase, Lactate Dehydrogenase, and Glyceraldehydephosphate Reductase, Malate Dehydrogenase", Journal of Medicinal Chemistry, 19(1):71-98 (1976).
Yoshino, et al., "Organic Phosphorous Compounds. 2. Synthesis and Coronary Vasodilator Activity of (Benzothiazolybenzyl) Phosphonate Derivatives", J. Med. Chem., 32:1528-1532 (1989).
Yu, et al., "Frequency of TPR-MET Rearrangement in Patients with Gastric Carcinoma and in First-Degree Relatives", Cancer, 88(8):1801-1806 (2000).
Zaidi, et al., "New Anti-Mycobacterial Hydantoins", Pharmazie, 35:755-756 (1980).
Zhen, et al., "Structural and Functional Domains Critical for Constitutive Activation of the HGF- Receptor (Met)", Oncogene, 9(6):1691-1697 (1994).
Zinner, et al., "Zur Weiteren Kenntnis Bicyclischer 3.5-Dioxopyrazolidine", Die Pharmazie, 25(5):309-312 (1970).
Zustovich, F. et al., "Sorafenib plus Daily Low-dose Temozolomide for Relapsed Glioblastoma: A Phase II Study", Anticancer Research (2013), 33: pp. 3487-3494.
Zvilichovsky, et al., "Aminolysis and Polymerization of 3-(p-Toluenesulfonoxy) Hydantoin", Israel Journal of Chemistry, 7:547-554 (1969).

COMPOSITIONS OF 1-(4-BROMO-5-(1-ETHYL-7-(METHYLAMINO)-2-OXO-1,2-DIHYDRO-1,6-NAPHTHYRIDIN-3-YL)-2-FLUOROPHEYL)-3-PHENYLUREA

CROSS-REFERENCE TO RELATED APPLICATIONS

This application is a continuation of U.S. Ser. No. 18/178,789 filed Mar. 6, 2023, which is a continuation of U.S. Ser. No. 18/148,766 filed Dec. 30, 2022, which is a continuation of U.S. Ser. No. 17/735,820 filed May 3, 2022, which is a continuation of U.S. Ser. No. 17/180,241 (now U.S. Pat. No. 11,395,818) filed Feb. 19, 2021, which is a continuation of International Application Number PCT/US2020/067560 filed Dec. 30, 2020, which claims priority to U.S. Ser. No. 62/955,073 filed Dec. 30, 2019, U.S. Ser. No. 62/955,062 filed Dec. 30, 2019, U.S. Ser. No. 62/968,695 filed Jan. 31, 2020, and U.S. Ser. No. 62/968,724 filed Jan. 31, 2020, the contents of each of which are incorporated herein by reference in their entirety.

BACKGROUND c-KIT (also known as KIT, CD117, and stem cell factor receptor) is a 145 kDa transmembrane tyrosine kinase protein that acts as a type-III receptor. The c-KIT proto-oncogene, located on chromosome 4q11-21, encodes the c-KIT receptor, whose ligand is the stem cell factor (SCF), steel factor, kit ligand, and mast cell growth factor. The receptor has tyrosine-protein kinase activity and binding of the ligand SCF leads to the autophosphorylation of c-KIT and its association with substrates such as phosphatidylinositol 3-kinase (PI3K). Tyrosine phosphorylation by protein tyrosine kinases is of particular importance in cellular signaling and can mediate signals for major cellular processes, such as proliferation, survival, differentiation, apoptosis, attachment, invasiveness and migration. Defects in c-KIT are a cause of piebaldism, an autosomal dominant genetic developmental abnormality of pigmentation characterized by congenital patches of white skin and hair that lack melanocytes. Gain-of-function mutations of the c-KIT gene and the expression of constitutively phosphorylated c-KIT are found in most gastrointestinal stromal tumors (GIST) and mastocytosis. Further, almost all gonadal seminomas/dysgerminomas exhibit c-KIT membranous staining, and several reports have clarified that some (10-25%) have a c-KIT gene mutation. c-KIT defects have also been associated with testicular tumors including germ cell tumors (GCT) and testicular germ cell tumors (TGCT). C-KIT mutations also have been associated with a subset of cutaneous or acral melanoma.

Oncogenic genomic alterations of PDGFRα kinase or overexpression of PDGFRα kinase have been shown to be causative of human cancers. Missense mutations of PDGFRα kinase have been shown to be causative of a subset of GISTs. PDGFRα mutations are oncogenic drivers in approximately 8-10% of GISTs. The predominant PDGFRα mutation is exon 18 D842V, although other exon 18 mutations including D846Y, N848K, and Y849K, and exon 18 insertion-deletion mutations (INDELs) including RD841-842KI, DI842-843-IM, and HDSN845-848P have also been reported. Furthermore, rare mutations in PDGFRα exons 12 and 14 have also been reported. The PDGFRα exon 18 deletion mutations ΔD842-H845 and ΔI843-D846 have been reported in GIST. Amplification or mutations of PDGRFα have been described in human tissues of malignant peripheral nerve sheath tumors (MPNST). Amplification of PDGFRα has been described in multiple skin lesions of undifferentiated pleomorphic sarcoma and in intimal sarcoma. Amplification of PDGFRα has been linked to a subset of lung cancer patients. 4q12, containing the PDGFRα gene locus, is amplified in 3-7% of lung adenocarcinomas and 8-10% of lung squamous cell carcinomas. PDGFRα amplification is common in pediatric and adult high-grade astrocytomas and identified a poor prognostic group in IDH1 mutant glioblastoma. PDGFRα amplification was frequent in pediatric (29.3%) and adult (20.9%) tumors. PDGFRα amplification was reported to increase with grade and in particular to be associated with a less favorable prognosis in IDH1 mutant de novo GBMs. The PDGFRα locus in PDGFRα-amplified gliomas has been demonstrated to present a PDGFRα exon 8,9 intragenic deletion rearrangement. This intragenic deletion was common, being present in 40% of the glioblastoma multiformes (GBMs) presenting with PDGFRα amplification. Tumors with this rearrangement displayed histologic features of oligodendroglioma, and the PDGFRα exon 8,9 intragenic deletion showed constitutively elevated tyrosine kinase activity. The FIP1L1-PDGFRA fusion protein is oncogenic in a subset of patients with hypereosinophilic syndrome. FIPIL1-PDGFRα fusion has also been identified in eosinophilia-associated acute myeloid leukemia and lymphoblastic T-cell lymphoma.

Such a broad-spectrum c-KIT inhibitor, and formulations thereof, would be of high therapeutic value in the treatment of refractory GIST patients and those suffering from other disorders. There is a need for oral formulations that provide significantly stable products to patients Mutations, deletions, rearrangements, and amplification of the PDGFRα gene are linked to a number of solid and hematological cancers. Given the complex function of the PDGRFα gene and the potential utility for PDGFRα inhibitors in the treatment of various solid and hematological cancers, there is a need for oral formulations of inhibitors with good therapeutic properties.

SUMMARY

Provided herein, in part, are compositions comprising a compound of Formula (I) with the purity and safety aspects to be considered for pharmaceutical preparations. A compound of Formula (I) as described herein has the following structure:

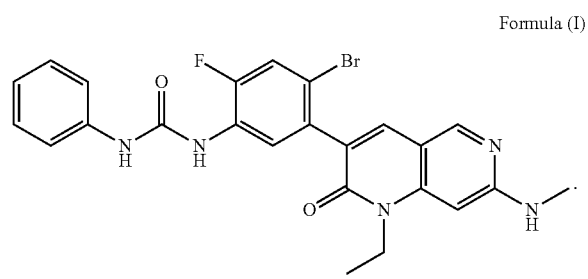 [SMILES: CCn1c(=O)c(-c2cc(NC(=O)Nc3ccccc3)c(F)cc2Br)cc2cnc(NC)cc21]

Formula (I)

Provided herein, in part, are pharmaceutical compositions comprising a compound of Formula (I):

Formula (I)

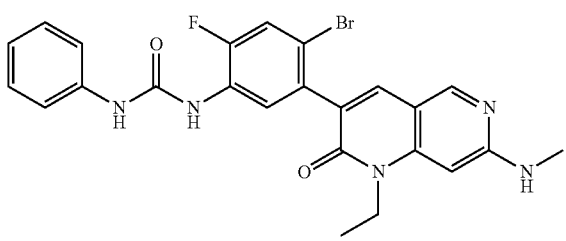

and one or more pharmaceutically acceptable carriers, excipients or diluents, wherein the pharmaceutical composition comprises one or more anilinic substances, each in an amount equal to or less than 3.0% by weight based on the weight of the compound of Formula (I).

Provided herein, in part, are pharmaceutical compositions comprising a compound of Formula (I):

Formula (I)

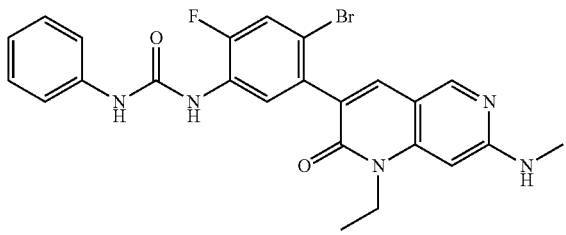

and one or more pharmaceutically acceptable carriers, excipients or diluents, wherein the pharmaceutical composition comprises one or more anilinic substances and a compound represented by Formula (III):

Formula (III)

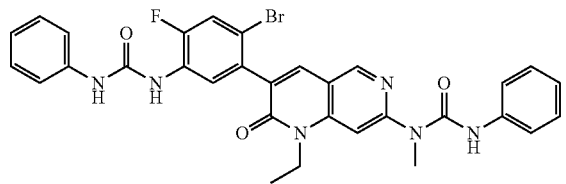

each in an amount equal to or less than 3.0% by weight based on the weight of the compound of Formula (I).

In some embodiments, provided herein is the solid dispersion comprising a compound of Formula (I) and a polymer, wherein the pharmaceutical composition comprises one or more anilinic substances, each in an amount equal to or less than 3.0% by weight based on the weight of the compound of Formula (I).

In some embodiments, provided herein is a pharmaceutical composition comprising the compound of Formula (I) and a pharmaceutically acceptable carrier, wherein the composition has less than 3% w/w of each of: 3-(5-amino-2-bromo-4-fluorophenyl)-1-ethyl-7-(methylamino)-1,6-naphthyridin-2(1H)-one (the compound of Formula (II)), aniline and diphenyl urea.

In an embodiment, provided herein is a pharmaceutical composition comprising the compound of Formula (I) and a pharmaceutically acceptable carrier, wherein the composition has less than 3% w/w of each of: 3-(5-amino-2-bromo-4-fluorophenyl)-1-ethyl-7-(methylamino)-1,6-naphthyridin-2(1H)-one (the compound of Formula (II)), a compound represented by Formula (III):

Formula (III)

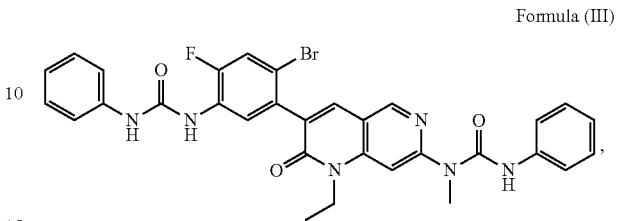

aniline and diphenyl urea.

In an embodiment, described herein is a substantially purified compound represented by Formula (I) having less than about 3.0% by weight of an impurity selected from the group consisting of the compound of Formula (II), aniline, and combinations thereof. In some embodiments, the compound comprises less than 0.5% of the impurity.

In an embodiment, described herein is a substantially purified compound represented by Formula (I) having less than about 3.0% by weight of an impurity selected from the group consisting of the compound of Formula (II), the compound of Formula (III), and combinations thereof. In some embodiments, the compound comprises less than 0.5% of the impurity.

In an embodiment, described herein is a high purity compound represented by the compound of Formula (I) having less than about 3.0% of anilinic substance impurities.

In another embodiment, provided herein is a high purity compound represented by the compound of Formula (I) having less than about 0.05% of a diphenyl urea impurity.

In an embodiment, provided herein is a pharmaceutical composition comprising: (a) an intragranular blend comprising: (i) a solid dispersion comprising a compound represented by Formula (I), wherein the pharmaceutical composition is comprises one or more anilinic substance, each in an amount equal to or less than 3% by weight based on the weight of the compound of Formula (I), and a pharmaceutically acceptable polymer; (ii) one or more fillers; (iii) a disintegrant; (iv) a glidant; and (v) a lubricant; and (b) an extragranular blend comprising: (i) a glidant; and (ii) a lubricant. In some embodiments, each anilinic substance is present in an amount equal to or less than about 5.0% by weight based on the weight of the compound of Formula (I). In some embodiments, each anilinic substance is present in an amount equal to or less than about 4.0% by weight based on the weight of the compound of Formula (I). In some embodiments, each anilinic substance is present in an amount equal to or less than about 2.0% by weight based on the weight of the compound of Formula (I). In some embodiments, each anilinic substance is present in an amount equal to or less than about 1.0% by weight based on the weight of the compound of Formula (I). In some embodiments, each anilinic substance is present in an amount equal to or less than about 0.7% by weight based on the weight of the compound of Formula (I). In some embodiments, each anilinic substance is present in an amount equal to or less than about 0.5% by weight based on the weight of the compound of Formula (I). In some embodiments, each anilinic substance is present in an amount equal to or less than about 0.3% by weight based on the weight of the compound of Formula (I).

In an embodiment, the disclosure provides a pharmaceutical composition comprising: (a) an intragranular blend comprising: (i) about 33% by weight of a solid dispersion based on the total weight of the composition, the solid dispersion comprising a compound represented by Formula (I) and hydroxypropyl methyl cellulose acetate succinate, wherein the solid dispersion comprises about 25% by weight of the compound represented by Formula (I) based on the total weight of the solid dispersion; (ii) about 30% by weight of microcrystalline cellulose based on the total amount of the of the composition; (iii) about 30% by weight of lactose monohydrate based on the total amount of the of the composition; (iv) about 5% by weight of crospovidone based on the total amount of the of the composition; (v) about 0.5% by weight of silicon dioxide based on the total amount of the of the composition; and (vi) about 0.5% by weight of magnesium stearate based on the total amount of the of the composition; and (b) an extragranular blend comprising: (i) about 0.5% by weight of silicon dioxide based on the total amount of the of the composition; and (ii) about 0.5% by weight of magnesium stearate based on the total amount of the composition.

In an embodiment, provided herein is a pharmaceutical composition comprising: (a) an intragranular blend comprising: (i) about 200 mg of a solid dispersion comprising a compound represented by Formula (I), wherein the pharmaceutical composition comprises one or more anilinic substance, each in an amount equal to or less than 3% by weight based on the weight of the compound of Formula (I) and hydroxypropyl methyl cellulose acetate succinate, wherein the solid dispersion comprises about 50 mg of the compound represented by Formula (I); (ii) about 179 mg of microcrystalline cellulose; (iii) about 179 mg of lactose monohydrate; (iv) about 30 mg of crospovidone; (v) about 3 mg of silicon dioxide; and (vi) about 3 mg of magnesium stearate; and (b) an extragranular blend comprising: (i) about 3 mg of silicon dioxide; and (ii) about 3 mg of magnesium stearate. In some embodiments, each anilinic substance is present in an amount equal to or less than about 5.0% by weight based on the weight of the compound of Formula (I). In some embodiments, each anilinic substance is present in an amount equal to or less than about 4.0% by weight based on the weight of the compound of Formula (I). In some embodiments, each anilinic substance is present in an amount equal to or less than about 2.0% by weight based on the weight of the compound of Formula (I). In some embodiments, each anilinic substance is present in an amount equal to or less than about 1.0% by weight based on the weight of the compound of Formula (I). In some embodiments, each anilinic substance is present in an amount equal to or less than about 0.7% by weight based on the weight of the compound of Formula (I). In some embodiments, each anilinic substance is present in an amount equal to or less than about 0.5% by weight based on the weight of the compound of Formula (I). In some embodiments, each anilinic substance is present in an amount equal to or less than about 0.3% by weight based on the weight of the compound of Formula (I).

In an embodiment, provided herein is a tablet providing about 50 mg of a compound represented by Formula (I), wherein the tablet comprises one or more anilinic substance impurities, each in an amount equal to or less than 3% by weight based on the weight of the compound of Formula (I), wherein the tablet comprises: (a) an intragranular blend comprising: (i) about 195 mg to about 205 mg of a solid dispersion that comprises about 50 mg of the compound and hydroxypropyl methyl cellulose acetate succinate; (ii) about 177 mg to about 181 mg of microcrystalline cellulose; (iii) about 177 mg to about 181 mg of lactose monohydrate; and (iv) about 28 mg to about 32 mg of crospovidone; and (b) an extragranular blend comprising: (i) about 2 mg to about 4 mg of silicon dioxide; and (ii) about 2 mg to about 4 mg of magnesium stearate. In some embodiments, each anilinic substance is present in an amount equal to or less than about 5.0% by weight based on the weight of the compound of Formula (I). In some embodiments, each anilinic substance is present in an amount equal to or less than about 4.0% by weight based on the weight of the compound of Formula (I). In some embodiments, each anilinic substance is present in an amount equal to or less than about 2.0% by weight based on the weight of the compound of Formula (I). In some embodiments, each anilinic substance is present in an amount equal to or less than about 1.0% by weight based on the weight of the compound of Formula (I). In some embodiments, each anilinic substance is present in an amount equal to or less than about 0.7% by weight based on the weight of the compound of Formula (I). In some embodiments, each anilinic substance is present in an amount equal to or less than about 0.5% by weight based on the weight of the compound of Formula (I). In some embodiments, each anilinic substance is present in an amount equal to or less than about 0.3% by weight based on the weight of the compound of Formula (I).

In an embodiment, provided herein are methods for treating a disease caused by the kinase activity of c-KIT or PDGFRA, and oncogenic forms thereof, wherein the disease is gastrointestinal stromal tumors (GIST), KIT driven gastrointestinal stromal tumors, PDGFRA driven gastrointestinal stromal tumors, melanoma (e.g., cutaneous melanoma, noncutaneous melanoma, KIT driven melanoma or PGDFRA driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, or non-small cell lung cancer. In some embodiments, melanoma is cutaneous melanoma or noncutaneous melanaoma. In some embodiments, melanoma is cutaneous melanoma. In some embodiments, cutaneous melanoma is superficial spreading melanoma, nodular melanoma, acral-lentiginous melanoma, or amelanotic and desmoplastic melanoma. In some embodiments, melanoma is noncutaneous (non-skin) melanoma. In some embodiments, noncutaneous melanoma is ocular melanoma or mucosal melanoma.

Also provided herein, in another embodiment, is a method of treating a disease selected from the group consisting of gastrointestinal stromal tumors (GIST), NF-1-deficient gastrointestinal stromal tumors, succinate dehydrogenase (SDH)-deficient gastrointestinal stromal tumors, KIT driven gastrointestinal stromal tumors, PDGFRA driven gastrointestinal stromal tumors, melanoma, acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer in a patient in need thereof, comprising administering to the patient a therapeutically effective amount of a composition described herein.

Also provided herein, in another embodiment, is a method of treating a disease selected from the group consisting of gastrointestinal stromal tumors (GIST), KIT driven gastrointestinal stromal tumors, PDGFRA driven gastrointestinal stromal tumors, lung cancer, glioblastoma, a glioma, malignant peripheral nerve sheath sarcoma, and hypereosinophilic syndrome in a patient in need thereof, comprising administering to the patient a therapeutically effective amount of a composition described herein.

Also provided herein, in another embodiment, is a method of treating a disease selected from the group consisting of KIT driven germ cell tumor (e.g., testicular germ cell), KIT driven skin cancer, or KIT driven renal cell carcinoma in a patient in need thereof, comprising administering to the patient a therapeutically effective amount of a composition described herein.

Also provided herein, in another embodiment, is a method of treating a disease selected from the group consisting of penile cancer, PDGFRA driven penile cancer, prostate cancer, PDGFRA driven prostate cancer, PDGFRA driven non-melanoma skin cancer, PDGFRA driven glioma, PDGFRA driven sarcoma, PDGFRA driven glioblastoma, or PDGFRA driven pancreatic cancer in a patient in need thereof, comprising administering to the patient a therapeutically effective amount of a composition or one or more tablets described herein.

Also provided herein, in another embodiment, is a method of treating a disease comprising a PDGFRB mutation selected from the group consisting of vaginal cancer, prostate cancer, penile cancer, non-melanoma skin cancer, melanoma, or breast sarcoma in a patient in need thereof, comprising administering to the patient a therapeutically effective amount of a composition described herein.

In some embodiments, provided herein is a method for treating diseases driven by KIT mutations or PDGFRA mutations in a patient in need thereof, comprising administering to the patient a therapeutically effective amount of a composition or one or more tablets described herein. In some embodiments, provided herein is a method for treating diseases driven by KIT mutations and PDGFRA mutations in a patient in need thereof, comprising administering to the patient a therapeutically effective amount of a composition or one or more tablets described herein. In some embodiments, provided herein is a method for treating diseases driven by KIT mutations or PDGFRA mutations, comprising passenger PDGFRB mutations in a patient in need thereof, comprising administering to the patient a therapeutically effective amount of a composition or one or more tablets described herein. In some embodiments, provided herein is a method for treating a disease selected from the group consisting of gastrointestinal stromal tumors (GIST), KIT driven gastrointestinal stromal tumors, PDGFRA driven gastrointestinal stromal tumors, melanoma (e.g., KIT driven melanoma or PGDFRA driven melanoma or PGDFR driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer in a patient in need thereof, comprising administering to the patient a therapeutically effective amount of a composition or one or more tablets described herein. In some embodiments, the melanoma is cutaneous melanoma or noncutaneous melanaoma. In some embodiments, the melanoma is cutaneous melanoma. In some embodiments, the cutaneous melanoma is superficial spreading melanoma, nodular melanoma, acral-lentiginous melanoma, or amelanotic and desmoplastic melanoma. In some embodiments, the melanoma is noncutaneous (non-skin) melanoma. In some embodiments, the noncutaneous melanoma is ocular melanoma or mucosal melanoma. In some embodiments, the disease is caused by the kinase activity of c-KIT and/or PDGFRA, and/or oncogenic forms thereof. In some embodiments, the disease is selected from the group consisting of KIT driven germ cell tumor (e.g., testicular germ cell), KIT driven skin cancer (e.g., KIT driven cutaneous squamous cell carcinoma, KIT driven Merkel cell carcinoma, uveal melanoma, non-melanoma skin cancer), or KIT driven renal cell carcinoma (e.g., renal cell carcinoma, chromophobe renal cell carcinoma). In some embodiments, the disease is selected from the group consisting of penile cancer, PDGFRA driven penile cancer, prostate cancer, PDGFRA driven prostate cancer, PDGFRA driven non-melanoma skin cancer, PDGFRA driven glioma, PDGFRA driven sarcoma, PDGFRA driven glioblastoma, or PDGFRA driven pancreatic cancer. In some embodiments, the disease comprising a PDGFRB mutation is selected from the group consisting of vaginal cancer, prostate cancer, penile cancer, non-melanoma skin cancer, melanoma, or breast sarcoma.

Also provided herein, in another embodiment, is a use of a composition or tablets described herein for the preparation of a medicament for the treatment of a disease selected from the group consisting of gastrointestinal stromal tumors (GIST), KIT driven gastrointestinal stromal tumors, PDGFRA driven gastrointestinal stromal tumors, melanoma, acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer.

In another embodiment, described herein is a process for the preparation of the solid dispersion comprising a compound of Formula (I)

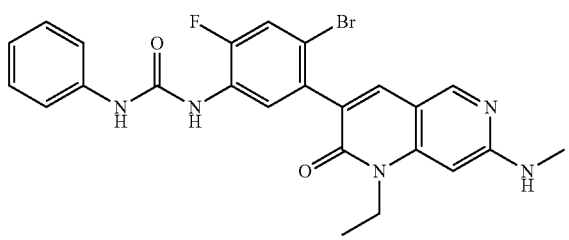

Formula (I)

e.g., a solid dispersion described herein, the process comprising: (a) mixing the compound of Formula (I), a solvent, the polymer and water to obtain a suspension; (b) optionally agitating and/or mixing the suspension while maintaining a temperature of about 10 to about 25° C.; (c) heating the suspension to dissolve the suspended particles prior to introduction into a spray-dryer; and (d) spray-drying the suspension to obtain a spray-dried dispersion; (e) drying the spray-dried dispersion; thereby obtaining the solid dispersion. In some embodiments, a solid dispersion comprising a compound of Formula (I)

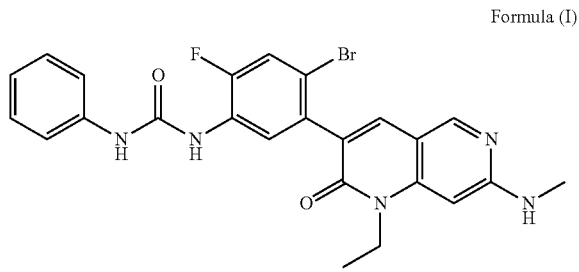 [SMILES: CCn1c(=O)c(-c2cc(NC(=O)Nc3ccccc3)c(F)cc2Br)cc2cnc(NC)cc21]

Formula (I)

e.g., a solid dispersion described herein, is produced by said process.

DETAILED DESCRIPTION

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

As used herein, the term "excipient" refers to a substance that may be beneficial to include in a composition with an active agent. The term "excipient" includes inert substances as well as functional excipients that may result in beneficial properties of the composition. Exemplary excipients include but are not limited to polymers, glidants, sugars, lubricant, salts, buffers, fats, fillers, disintegrating agents, binders, surfactants, high surface area substrates, flavorants, carriers, matrix materials, and so forth.

As used herein, the terms "Anilinic impurity A," "Impurity A," and Compound 2 each refer to the compound 3-(5-amino-2-bromo-4-fluorophenyl)-1-ethyl-7-(methylamino)-1,6-naphthyridin-2(1H)-one, the structure of which is the compound of Formula (II):

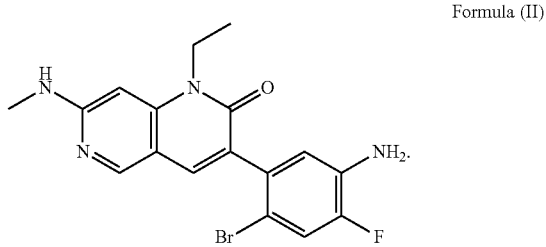 [SMILES: CCn1c(=O)c(-c2cc(N)c(F)cc2Br)cc2cnc(NC)cc21]

Formula (II)

In some embodiments, an anilinic substance may be Impurity A.

As used herein, the terms "Anilinic impurity B," "Impurity B" refer to aniline. In some embodiments, an anilinic substance may be Impurity B.

As used herein, the terms "Anilinic substances," "anilinic substance impurity," "anilinic substance impurities" are alone or together and may include but are not limited to 3-(5-amino-2-bromo-4-fluorophenyl)-1-ethyl-7-(methylamino)-1,6-naphthyridin-2(1H)-one (compound of Formula (II)) or aniline.

As used herein, the terms "Anilinic impurities," "anilinic impurity," "anilinic substance impurity," "anilinic substance impurities" are alone or together and may include but are not limited to 3-(5-amino-2-bromo-4-fluorophenyl)-1-ethyl-7-(methylamino)-1,6-naphthyridin-2(1H)-one (compound of Formula (II)) or aniline.

As used herein, the terms "Individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

As used herein, the terms "Pharmaceutically acceptable" or "pharmacologically acceptable" includes molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

As used herein, the term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

As used herein, the term "pharmaceutical composition" as used herein refers to a composition comprising at least one compound as disclosed herein formulated together with one or more pharmaceutically acceptable carriers, excipients or diluents.

As used herein, the term "therapeutically effective amount" means the amount of the subject compound that will elicit the biological or medical response of a tissue, system or animal, (e.g., mammal or human) that is being sought by the researcher, veterinarian, medical doctor or other clinician. The compounds described herein are administered in therapeutically effective amounts to treat a disorder.

As used herein, the term "treating" includes any effect, e.g., lessening, reducing, modulating, or eliminating, that results in the improvement of the condition, disease, disorder and the like.

As used herein, the term "active agent" means a drug, medicament, pharmaceutical, therapeutic agent, for example, a compound of Formula (I) as described herein.

As used herein, the term "oral formulation" as used herein, refers to a composition or medium used to administer a compound as disclosed herein (e.g., a compound of Formula (I) to a subject in need thereof by oral administration. Typically, an oral formulation is administered via the mouth, however, "oral formulation" as used herein is intended to cover any substance which is administered to a subject and is absorbed across a membrane, e.g., a mucosal membrane, of the gastrointestinal tract, including, e.g., the mouth, esophagus, stomach, small intestine, large intestine, and colon. In one embodiment, the oral formulation is a solid oral formulation. In one embodiment, the oral formulation is a solid oral formulation administered to a subject in need thereof via the mouth.

A "combination therapy" is a treatment that includes the administration of two or more therapeutic agents, e.g., a compound of Formula I and a MAPKAP pathway inhibitor, to a patient. The two or more therapeutic agents may be delivered at the same time, e.g., in separate pharmaceutical compositions or in the same pharmaceutical composition, or they may be delivered at different times. For example, they may be delivered concurrently or during overlapping time periods, and/or one therapeutic agent may be delivered before or after the other therapeutic agent(s). Treatment with a combination therapy optionally includes treatment with either single agent, preceded or followed by a period of concurrent treatment with both agents. However, it is contemplated that during some time period, effective amounts of the two or more therapeutic agents are present within the patient.

All ranges recited herein include the endpoints, including those that recite a range "between" two values. Term "substantially" and "about" is to be construed as modifying a term or value such that it is not an absolute. This includes, at very least, the degree of expected experimental error, technique error and instrument error for a given technique used to measure a value.

Process

In one aspect, provided herein, is a process of preparing a composition comprising a compound of Formula (I)

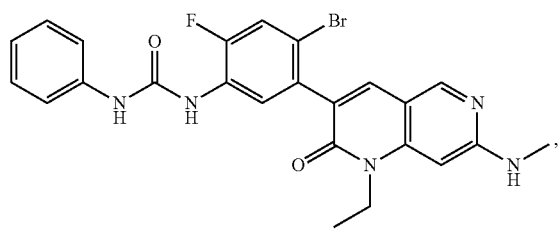

Formula (I)

having one or more anilinic substances, each in an amount equal to or less than 3% by weight of the compound of Formula (I) comprising:

(a) weighing and dispensing the compound of Formula (I), a solvent, polymer and water;
(b) charging and suspending the compound of Formula (I);
(c) optionally agitating and mixing the final suspension while maintaining a temperature of about 10-25° C.; and
(d) passing the resulting suspension through an in-line heat exchanger to dissolve the suspended particles prior to introduction into the spray dryer; and
(e) optionally drying the spray dried compound of Formula (I).
(f) In another embodiment, described herein is a process for the preparation of the solid dispersion comprising a compound of Formula (I)

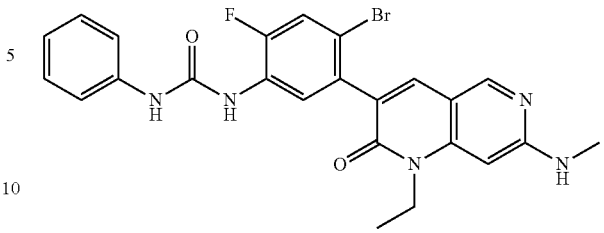

Formula (I)

e.g., a solid dispersion described herein, the process comprising: (a) mixing the compound of Formula (I), a solvent, the polymer and water to obtain a suspension; (b) optionally agitating and/or mixing the suspension while maintaining a temperature of about 10 to about 25° C.; (c) heating the suspension to dissolve the suspended particles prior to introduction into a spray-dryer; and (d) spray-drying the suspension to obtain a spray-dried dispersion; (e) drying the spray-dried dispersion; thereby obtaining the solid dispersion. In some embodiments, heating comprises passing the suspension through an in-line heat exchanger. In some embodiments, a solid dispersion comprising a compound of Formula (I)

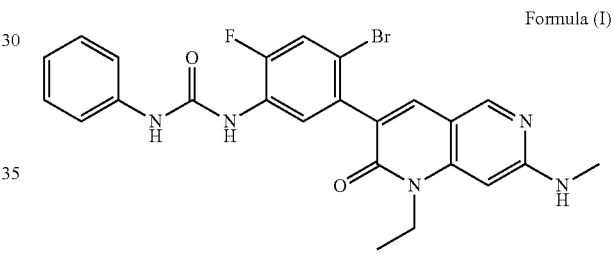

Formula (I)

e.g., a solid dispersion described herein, is produced by said process.

For purposes described herein, one of ordinary skill in the art would understand that anilinic substances are considered impurities in the compositions, pharmaceutical compositions, and solid dispersions as described herein. The concentration of the impurities in the composition, pharmaceutical composition or solid dispersions described herein depend on the concentration of the compound of Formula (I). For example, the concentration of anilinic substances in the composition, pharmaceutical composition or solid dispersion of the inventions described herein would be expected in some embodiments, each anilinic substance is present in an amount equal to or less than about 5.0% by weight based on the weight of the compound of Formula (I) present in the composition, pharmaceutical composition or solid dispersion as described herein. In some embodiments, each anilinic substance is present in an amount equal to or less than about 4.0% by weight based on the weight of the compound of Formula (I). In some embodiments, each anilinic substance is present in an amount equal to or less than about 2.0% by weight based on the weight of the compound of Formula (I). In some embodiments, each anilinic substance is present in an amount equal to or less than about 1.0% by weight based on the weight of the compound of Formula (I). In some embodiments, each anilinic substance is present in an amount equal to or less than about 0.7% by weight based on the weight of the compound of Formula (I). In some embodiments, each anilinic substance is present in an amount equal to or less than about 0.5% by weight based on the weight of the compound of Formula (I). In some embodiments, each anilinic substance is present in an amount equal to or less than about 0.3% by weight based on the weight of the compound of Formula (I).

In some embodiments, the compound of Formula (I), solvent, polymer and water are combined, and the mixture is agitated and mixed to a suspension. In some embodiments, the solvent, water and polymer are combined and agitated prior to the addition of the compound of Formula (I). In some embodiments, the solvent and water are combined and agitated prior to the addition of the polymer and the compound of Formula (I). In some embodiments, the solvent and water are combined and agitated followed by addition of the polymer, followed by addition of the compound of Formula (I).

In some embodiments, the solvent:water ratio may be about 95:5, followed by the addition and dissolution of the polymer. In some embodiments, the solvent:water ratio may be about 90:10, followed by the addition and dissolution of the polymer. In some embodiments, the solvent:water ratio may be about 85:15, followed by the addition and dissolution of the polymer. In some embodiments, the solvent:water ratio may be about 80:20, followed by the addition and dissolution of the polymer. In some embodiments, the solvent:water ratio may be about 75:25, followed by the addition and dissolution of the polymer. In some embodiments, the solvent:water ratio may be about 70:30, followed by the addition and dissolution of the polymer. In some embodiments, the solvent:water ratio may be about 65:35, followed by the addition and dissolution of the polymer. In some embodiments, the solvent:water ratio may be about 60:40, followed by the addition and dissolution of the polymer. In some embodiments, the solvent:water ratio may be about 55:45, followed by the addition and dissolution of the polymer. In some embodiments, the solvent:water ratio may be about 50:50, followed by the addition and dissolution of the polymer.

In some embodiments, the solvent is an organic compound in which the active agent and polymer are mutually soluble. In some embodiments, the solvent is an alcohol, ketone, ether, ester, halogenated alkane, amide, sulfone, acid, or a nitro compound. In some embodiments, the solvent is methanol, ethanol, n-propanol, iso-propanol, or butanol. In some embodiments, the solvent is acetone, methyl ethyl ketone (MEK), or methyl isobutyl ketone (MIBK). In some embodiments, the solvent is methyl acetate, ethyl acetate, or propylacetate. In some embodiments, the solvent is diethylether, tetrahydrofuran (THF), 2-methyl THF, 2,5-dimethyl THF, or 2,2,5,5-tetramethyl THF. In some embodiments, the solvent is acetonitrile, methylene chloride, toluene, 1,1,1-trichloroethane, dimethyl acetamide (DMA), nitromethane, acetic acid, or dimethylsulfoxide (DMSO). Mixtures of solvent and water are suitable as long as the polymer and the Compound of Formula (I) are sufficiently soluble to make the spray-drying process practicable. In some embodiments, the water:solvent mixture is water:acetone. In some embodiments, the water:solvent mixture is water:THF. In some embodiments, the water:solvent mixture is water:methanol. In some embodiments, the water:solvent mixture is water:ethanol. In some embodiments, the water:solvent mixture is water:methyl ethyl ketone. In some embodiments, the water:solvent mixture is water:ethyl acetate. In some embodiments, the water:solvent mixture is water:methylene chloride. In some embodiments, mixtures of solvents are suitable as long as the polymer and the Compound of Formula (I) are sufficiently soluble to make the spray-drying process practicable. In some embodiments, the solvent:solvent mixture is methanol:ethylacetate. In some embodiments, the solvent:solvent mixture ethanol:ethylacetate. In some embodiments, the solvent:solvent mixture is methanol:dichloromethane. In some embodiments, the solvent:solvent mixture ethanol:dichloromethane.

In some embodiments, the temperature range for the agitating and mixing of the final suspension is about 0-25° C. In some embodiments, the temperature range for the agitating and mixing of the final suspension is about 5-25° C. In some embodiments, the temperature range for the agitating and mixing of the final suspension is about 10-25° C. In some embodiments, the temperature range for the agitating and mixing of the final suspension is about 15-25° C. In some embodiments, the temperature range for the agitating and mixing of the final suspension is about 15-24° C. In some embodiments, the temperature range for the agitating and mixing of the final suspension is about 15-23° C. In some embodiments, the temperature range for the agitating and mixing of the final suspension is about 15-22° C. In some embodiments, the temperature range for the agitating and mixing of the final suspension is about 15-21° C. In some embodiments, the temperature range for the agitating and mixing of the final suspension is about 15-20° C. In some embodiments, the temperature range for the agitating and mixing of the final suspension is about 17-25° C. In some embodiments, the temperature range for the agitating and mixing of the final suspension is about 17-24° C. In some embodiments, the temperature range for the agitating and mixing of the final suspension is about 17-23° C. In some embodiments, the temperature range for the agitating and mixing of the final suspension is about 17-22° C. In some embodiments, the temperature range for the agitating and mixing of the final suspension is about 17-21° C. In some embodiments, the temperature range for the agitating and mixing of the final suspension is about 17-20° C. In some embodiments, the temperature range for the agitating and mixing of the final suspension is about 18-25° C. In some embodiments, the temperature range for the agitating and mixing of the final suspension is about 18-24° C. In some embodiments, the temperature range for the agitating and mixing of the final suspension is about 18-23° C. In some embodiments, the temperature range for the agitating and mixing of the final suspension is about 18-22° C. In some embodiments, the temperature range for the agitating and mixing of the final suspension is about 18-21° C. In some embodiments, the temperature range for the agitating and mixing of the final suspension is about 18-20° C.

In some embodiments, the suspension flow rate through the inline heat exchanger operating range may be at about 5-100 kg/hr. In some embodiments, the suspension flow rate through the inline heat exchanger operating range may be at about 5-30 kg/hr. In some embodiments, the suspension flow rate through the inline heat exchanger operating range may be at about 5-25 kg/hr. In some embodiments, the suspension flow rate through the inline heat exchanger operating range may be at about 5-20 kg/hr. In some embodiments, the suspension flow rate through the inline heat exchanger operating range may be at about 5-15 kg/hr. In some embodiments, the suspension flow rate through the inline heat exchanger operating range may be at about 5-10 kg/hr. In some embodiments, the suspension flow rate through the inline heat exchanger operating range may be at about 30-50 kg/hr. In some embodiments, the suspension flow rate is about 35-45 kg/hr. In some embodiments, the suspension flow rate is about 35-40 kg/hr. In some embodiments, the suspension flow rate is about 40-45 kg/hr. In some embodiments, the suspension flow rate is about 42-48 kg/hr. In some embodiments, the suspension flow rate is about 45-50 kg/hr. In some embodiments, the suspension flow rate through the inline heat exchanger operating range may be at about 50-100 kg/hr. In some embodiments, the suspension flow rate is about 50-90 kg/hr. In some embodiments, the suspension flow rate is about 50-80 kg/hr. In some embodiments, the suspension flow rate is about 50-70 kg/hr. In some embodiments, the suspension flow rate is about 50-60 kg/hr.

In some embodiments, the solution temperature near or at the nozzle of the spray dryer may be at about 110-130° C., preferably about 115-125° C., most preferably about 116° C., about 117° C., about 118° C., about 119° C., about 120° C., about 121° C., about 122° C., about 123° C., about 124° C., about 125° C. In some embodiments, the solution temperature near or at the nozzle of the spray dryer may be at about 15-25° C. In some embodiments, the solution temperature near or at the nozzle of the spray dryer may be at about 20-25° C. In some embodiments, the solution temperature near or at the nozzle of the spray dryer may be at about 10-100° C. In some embodiments, the solution temperature near or at the nozzle of the spray dryer may be at about 20-90° C. In some embodiments, the solution temperature near or at the nozzle of the spray dryer may be at about 20-80° C. In some embodiments, the solution temperature near or at the nozzle of the spray dryer may be at about 20-70° C. In some embodiments, the solution temperature near or at the nozzle of the spray dryer may be at about 20-60° C. In some embodiments, the solution temperature near or at the nozzle of the spray dryer may be at about 20-50° C. In some embodiments, the solution temperature near or at the nozzle of the spray dryer may be at about 20-40° C. In some embodiments, the solution temperature near or at the nozzle of the spray dryer may be at about 20-30° C.

In some embodiments, the spray drying nozzle sheath gas pressure may be at about 50-100 psig. In some embodiments, the spry dryer bulk drying gas flow rate may be about 400-500 kg/hr. In some embodiments, the spray dryer chamber outlet temperature may be about 45-75° C. In some embodiments, the spray dryer condenser temperature may be about −5 to about −20° C.

After completion of the spray drying, the spray dried intermediate undergoes an optional secondary spray drying in an agitated vacuum dryer. In some embodiments, the drying temperature may be at about 30-60° C., preferably about 35-55° C., most preferably about 40-50° C. In some embodiments, the drying duration time may not be less than about 3 hours, preferably not less than about 6 hours, not less than about 7 hours, not less than about 8 hours, not less than about 9 hours. In some embodiments, the chamber pressure may be about 30-60 mbar, preferably about 35-55 mbar, most preferably about 40-50 mbar.

In some embodiments, the polymer may be ionic. In some embodiments, the polymer may be non-ionic. In some embodiments, the pharmaceutically acceptable polymer is selected from the group consisting of: polyvinyl pyrrolidone, polyethyleneoxide, polyethylene glycol, poly(vinyl pyrrolidone-co-vinyl acetate), polyoxyethylene-polyoxypropylene block copolymers, graft copolymers comprised of polyethylene glycol, polyvinyl caprolactam and polyvinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate, hydroxypropyl methyl cellulose propionate succinate, hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, carboxymethyl ethylcellulose, hydroxypropyl methylcellulose, hydroxypropyl methylcellulose acetate phthalate, hydroxypropyl methylcellulose propionate phthalate, hydroxypropyl methylcellulose acetate trimellitate, hydroxypropyl methylcellulose propionate trimellitate, cellulose acetate succinate, methyl cellulose acetate succinate, dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1, poly(methacrylic acid-co-methyl methacrylate) 1:2, poly(methacrylic acid-co-ethyl acrylate) 1:1, hydroxyethyl cellulose, methyl cellulose and hydroxy propyl cellulose, poly methacrylic acid-ethyl acrylate, poly methacrylic acid-methyl methacrylate, poly methyl methacrylate-ethyl acrylate, poly trimethylammonioethyl methacrylate chloride-methyl methacrylate-ethyl acrylate and poly(butylmethacrylate-co-(2-dimethylaminoethyl)methacrylate-co-methyl methacrylate), and mixtures thereof. In some embodiments, the pharmaceutically acceptable polymer is selected from the group consisting of polyvinyl pyrrolidone, polyethyleneoxide, polyethylene glycol, poly (vinyl pyrrolidone-co-vinyl acetate), polyoxyethylene-polyoxypropylene block copolymers, graft copolymers comprised of polyethylene glycol, polyvinyl caprolactam and polyvinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate, hydroxypropyl methyl cellulose propionate succinate, hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, carboxymethyl ethylcellulose, hydroxypropyl methylcellulose, hydroxypropyl methylcellulose acetate phthalate, hydroxypropyl methylcellulose propionate phthalate, hydroxypropyl methylcellulose acetate trimellitate, hydroxypropyl methylcellulose propionate trimellitate, cellulose acetate succinate, methyl cellulose acetate succinate, dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1, poly(methacrylic acid-co-methyl methacrylate) 1:2, poly(methacrylic acid-co-ethyl acrylate) 1:1, and mixtures thereof. In some embodiments, the polymer is hydroxypropyl methyl cellulose, hydroxypropyl cellulose, carboxymethyl ethyl cellulose, hydroxypropyl methyl cellulose acetate succinate, hydroxypropyl methyl cellulose phthalate, cellulose acetate phthalate, cellulose acetate trimellitate, polyvinyl alcohols that have at least a portion of their repeat units in hydrolyzed form, polyvinyl pyrrolidone, poloxamers, or blends thereof. In some embodiments, the pharmaceutically acceptable polymer is hydroxypropyl methyl cellulose acetate succinate.

In some embodiment, the resulting composition comprising the compound of Formula (I) comprises one or more anilinic substance, each in an amount equal to or less than 3.0% by weight based on the weight of the compound of Formula (I). Other impurities, which may include diphenyl urea are equal to or less than 0.3% by weight based on the weight of Formula (I).

Identifying the Impurities

The purity of the Compound of Formula (I) may be analyzed, generally by methods such as high-performance liquid chromatography (HPLC), gas chromatography (GC) or thin layer chromatography (TLC), to determine whether the impurities are present at levels suitable for pharmaceutical use. Generally, impurities are identified spectroscopically and provide a chromatographic peak on a chromatogram or as a spot on a TLC panel.

Once a peak position has been associated with a particular impurity, the impurity can be identified in a sample based on its position in the chromatogram, where the position in the chromatogram is measured in minutes between the injection of the sample in a column and elution of the impurity through the detector. The position in the chromatogram is known as the retention time and the ratio between the retention times is known as the relative retention time.

A relatively pure compound may be used as a reference standard. A reference standard is similar to a reference marker, except that the latter can be used not only for detecting impurities, but also for quantifying the amount of impurities present in the sample.

In some embodiments, the anilinic impurities each together or separately are present in an amount equal to or less than about 5% by weight based on the weight of the compound of Formula (I). In some embodiments, the anilinic impurities each together or separately are present in an amount equal to or less than about 4% by weight based on the weight of the compound of Formula (I). In some embodiments, the anilinic impurities each together or separately are present in an amount equal to or less than about 3% by weight based on the weight of the compound of Formula (I). In some embodiments, the anilinic impurities each together or separately are present in an amount equal to or less than about 2% by weight based on the weight of the compound of Formula (I). In some embodiments, the anilinic impurities each together or separately are present in an amount equal to or less than about 1% by weight based on the weight of the compound of Formula (I). In some embodiments, the anilinic impurities each together or separately are present in an amount equal to or less than about 0.75% by weight based on the weight of the compound of Formula (I). In some embodiments, the anilinic impurities each together or separately are present in an amount equal to or less than about 1% by weight based on the weight of the compound of Formula (I). In some embodiments, the anilinic impurities each together or separately are present in an amount equal to or less than about 0.75% by weight based on the weight of the compound of Formula (I). In some embodiments, the anilinic impurities each together or separately are present in an amount equal to or less than about 0.70% by weight based on the weight of the compound of Formula (I). In some embodiments, the anilinic impurities each together or separately are present in an amount equal to or less than about 0.65% by weight based on the weight of the compound of Formula (I). In some embodiments, the anilinic impurities each together or separately are present in an amount equal to or less than about 0.60% by weight based on the weight of the compound of Formula (I). In some embodiments, the anilinic impurities each together or separately are present in an amount equal to or less than about 0.55% by weight based on the weight of the compound of Formula (I). In some embodiments, the anilinic impurities each together or separately are present in an amount equal to or less than about 0.50% by weight based on the weight of the compound of Formula (I). In some embodiments, the anilinic impurities each together or separately are present in an amount equal to or less than about 0.45% by weight based on the weight of the compound of Formula (I). In some embodiments, the anilinic impurities each together or separately are present in an amount equal to or less than about 0.40% by weight based on the weight of the compound of Formula (I). In some embodiments, the anilinic impurities each together or separately are present in an amount equal to or less than about 0.35% by weight based on the weight of the compound of Formula (I). In some embodiments, the anilinic impurities each together or separately are present in an amount equal to or less than about 0.30% by weight based on the weight of the compound of Formula (I). In some embodiments, the anilinic impurities each together or separately are present in an amount equal to or less than about 0.25% by weight based on the weight of the compound of Formula (I). In some embodiments, the anilinic impurities each together or separately are present in an amount equal to or less than about 0.20% by weight based on the weight of the compound of Formula (I). In some embodiments, the anilinic impurities each together or separately are present in an amount equal to or less than about 0.15% by weight based on the weight of the compound of Formula (I). In some embodiments, the anilinic impurities each together or separately are present in an amount equal to or less than about 0.1% by weight based on the weight of the compound of Formula (I). In some embodiments the anilinic impurities are represented by one or more anilinic impurities selected from 3-(5-amino-2-bromo-4-fluorophenyl)-1-ethyl-7-(methylamino)-1,6-naphthyridin-2(1H)-one, aniline, and a combination thereof.

In some embodiments, the diphenyl urea impurity is present in an amount equal to or less than about 0.30% by weight based on the weight of the compound of Formula (I) which means from about 0.0001% to a maximum of about 0.30%. In some embodiments, the diphenyl urea impurity is present in an amount equal to or less than about 0.20% by weight based on the weight of the compound of Formula (I) which means from about 0.0001% to a maximum of about 0.20%. In some embodiments, the diphenyl urea impurity is present in an amount equal to or less than about 0.10% by weight based on the weight of the compound of Formula (I) which means from about 0.0001% to a maximum of about 0.10%. In some embodiments, the diphenyl urea impurity is present in an amount equal to or less than about 0.075% by weight based on the weight of the compound of Formula (I) which means from about 0.0001% to a maximum of about 0.075%. In some embodiments, the diphenyl urea impurity is present in an amount equal to or less than about 0.05% by weight based on the weight of the compound of Formula (I) which means from about 0.0001% to a maximum of about 0.05%. In some embodiments, the diphenyl urea impurity is present in an amount equal to or less than about 0.04% by weight based on the weight of the compound of Formula (I) which means from about 0.0001% to a maximum of about 0.04%. In some embodiments, the diphenyl urea impurity is present in an amount equal to or less than about 0.03% by weight based on the weight of the compound of Formula (I) which means from about 0.0001% to a maximum of about 0.03%. In some embodiments, the diphenyl urea impurity is present in an amount equal to or less than about 0.02% by weight based on the weight of the compound of Formula (I) which means from about 0.0001% to a maximum of about 0.02%. In some embodiments, the diphenyl urea impurity is present in an amount equal to or less than about 0.01% by weight based on the weight of the compound of Formula (I) which means from about 0.0001% to a maximum of about 0.01%.

In another general aspect, provided herein is a pharmaceutical composition comprising compound of Formula (I) having purity by HPLC of greater than about 95%. In some embodiments, the purity by HPLC is greater than about 96%. In some embodiments, the purity by HPLC is greater than about 97%. In some embodiments, the purity by HPLC is greater than about 98%. In some embodiments, the purity by HPLC is greater than about 99%. In some embodiments, the purity by HPLC is greater than about 99.5%. In some embodiments, the purity by HPLC is greater than about 99.8%. In some embodiments, the purity by HPLC is greater than about 99.9%. In some embodiments, the purity by HPLC is greater than about 90%. In some embodiments, the purity by HPLC is greater than about 92%. In some embodiments, the purity by HPLC is greater than about 94%.

Dispersions of the active agent and pharmaceutically acceptable polymer as described herein may be made by a spray-drying process. As used herein, the term "spray-dried dispersion" or "spray-dried powdered dispersion" means a product of a spray-drying process wherein the product comprises a dispersion of at least one active agent and at least one excipient, such as a polymer.

In the spray-drying process, the active agent and one or more polymers are dissolved in a common solvent. "Common" here means that the solvent, which can be a mixture of compounds, will dissolve both the active agent and the polymer(s). After both active agent and polymer have been dissolved, the solvent is rapidly removed by evaporation in the spray-drying apparatus, resulting in the formation of a substantially homogeneous solid dispersion. In such dispersions, the active agent is dispersed as homogeneously as possible throughout the polymer and can be thought of as a solid solution of active agent dispersed in the polymer(s).

The solvent is removed by the spray-drying process. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's *Chemical Engineers' Handbook*, pages 20-54 to 20-57 (Sixth Edition 1984). More details on spray-drying processes and equipment are reviewed by Marshall, "Atomization and Spray-Drying," 50 *Chem. Eng. Prog. Monogr. Series* 2 (1954), and Masters, *Spray Drying Handbook* (Fourth Edition 1985). Further, additional process and spray-drying techniques and equipment are described generally in U.S. Pat. Nos. 8,343,550 and 7,780,988. The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, a portion of the heat required for evaporation of solvent may be provided by heating the spray solution.

The drying gas may be virtually any gas, but to minimize the risk of fire or explosions due to ignition of flammable vapors, and to minimize undesirable oxidation of the active agent, concentration-enhancing polymer, or other materials in the dispersion, an inert gas such as nitrogen, nitrogen-enriched air, or argon is utilized. The temperature of the drying gas at the gas inlet of apparatus is typically from about 60° C. to about 300° C. The temperature of the product particles, drying gas, and evaporated solvent at the outlet or distal end of collection cone typically ranges from about 0° C. to about 100° C.

Solvents suitable for spray-drying process can be any organic compound in which the active agent and polymer are mutually soluble. The solvent should have relatively low toxicity and be removed from the dispersion to a level that is acceptable according to The International Committee on Harmonization (ICH) guidelines. Removal of solvent to this level may require a subsequent processing step such as tray-drying or secondary drying. In some embodiments, the solvent is an alcohol, ketone, ether, ester, halogenated alkane, amide, sulfone, acid, or a nitro compound. In some embodiments, the solvent is methanol, ethanol, n-propanol, iso-propanol, or butanol. In some embodiments, the solvent is acetone, methyl ethyl ketone (MEK), or methyl isobutyl ketone (MIBK). In some embodiments, the solvent is methyl acetate, ethyl acetate, or propylacetate. In some embodiments, the solvent is diethylether, tetrahydrofuran (THF), 2-methyl THF, 2,5-dimethyl THF, or 2,2,5,5-tetramethyl THF. In some embodiments, the solvent is acetonitrile, methylene chloride, toluene, 1,1,1-trichloroethane, dimethyl acetamide (DMA), nitromethane, acetic acid, or dimethylsulfoxide (DMSO). Mixtures of solvent and water are suitable as long as the polymer and the compound of Formula (I) are sufficiently soluble to make the spray-drying process practicable. In some embodiments, the water:solvent mixture is water:acetone. In some embodiments, the water:solvent mixture is water:THF. In some embodiments, the water:solvent mixture is water:methanol. In some embodiments, the water:solvent mixture is water:ethanol. In some embodiments, the water:solvent mixture is water:methyl ethyl ketone. In some embodiments, the water:solvent mixture is water:ethyl acetate. In some embodiments, the water:solvent mixture is water:methylene chloride. In some embodiments, mixtures of solvents are suitable as long as the polymer and the Compound of Formula (I) are sufficiently soluble to make the spray-drying process practicable. In some embodiments, the solvent:solvent mixture is methanol:ethylacetate. In some embodiments, the solvent:solvent mixture ethanol:ethylacetate. In some embodiments, the solvent:solvent mixture is methanol:dichloromethane. In some embodiments, the solvent:solvent mixture ethanol:dichloromethane.

The composition of the solvent-bearing feed will depend on the desired ratio of active agent-to-polymer in the dispersion and the solubility of the active agent and polymer in the solvent. Generally, it is desirable to use as high a combined active agent and polymer concentration in the solvent-bearing feed as possible, provided the active agent and polymer are dissolved in the solvent at the temperature range of the process, to reduce the total amount of solvent that must be removed to form the solid amorphous dispersion. In some embodiments, the solvent-bearing feed has a combined active agent and polymer concentration of at least about 0.01 wt % to at least about 20 wt %. In some embodiments, the solvent-bearing feed has a combined active agent and polymer concentration of at least about 0.01 wt %. In some embodiments, the solvent-bearing feed has a combined active agent and polymer concentration of at least about 0.1 wt %. In some embodiments, the solvent-bearing feed has a combined active agent and polymer concentration of at least about 0.5 wt %. In some embodiments, the solvent-bearing feed has a combined active agent and polymer concentration of at least about 1.0 wt %. In some embodiments, the solvent-bearing feed has a combined active agent and polymer concentration of at least about 2.0 wt %. In some embodiments, the solvent-bearing feed has a combined active agent and polymer concentration of at least about 3.0 wt %. In some embodiments, the solvent-bearing feed has a combined active agent and polymer concentration of at least about 4.0 wt %. In some embodiments, the solvent-bearing feed has a combined active agent and polymer concentration of at least about 5.0 wt %. In some embodiments, the solvent-bearing feed has a combined active agent and polymer concentration of at least about 6.0 wt %. In some embodiments, the solvent-bearing feed has a combined active agent and polymer concentration of at least about 7.0 wt %. In some embodiments, the solvent-bearing feed has a combined active agent and polymer concentration of at least about 8.0 wt %. In some embodiments, the solvent-bearing feed has a combined active agent and polymer concentration of at least about 9.0 wt %. In some embodiments, the solvent-bearing feed has a combined active agent and polymer concentration of at least about 10.0 wt %.

The average residence time of particles in the drying chamber should be at least 10 seconds, preferably at least 20 seconds. Typically, following solidification, the powder formed stays in the spray-drying chamber for about 5 to 60 seconds, causing further evaporation of solvent. The final solvent content of the solid dispersion as it exits the dryer should be low, since this reduces the mobility of active agent molecules in the dispersion, thereby improving its stability. Generally, the solvent content of the dispersion as it leaves the spray-drying chamber should be less than about 10 wt %. In some embodiments, the solvent content of the dispersion as it leaves the spray-drying chamber is less than about 9 wt %. In some embodiments, the solvent content of the dispersion as it leaves the spray-drying chamber is less than about 8 wt %. In some embodiments, the solvent content of the dispersion as it leaves the spray-drying chamber is less than about 7 wt %. In some embodiments, the solvent content of the dispersion as it leaves the spray-drying chamber is less than about 6 wt %. In some embodiments, the solvent content of the dispersion as it leaves the spray-drying chamber is less than about 5 wt %. In some embodiments, the solvent content of the dispersion as it leaves the spray-drying chamber is less than about 4 wt %. In some embodiments, the solvent content of the dispersion as it leaves the spray-drying chamber is less than about 3 wt %. In some embodiments, the solvent content of the dispersion as it leaves the spray-drying chamber is less than about 2 wt %. In some embodiments, the solvent content of the dispersion as it leaves the spray-drying chamber is less than about 1 wt %. In some embodiments, the acetone content of the dispersion as it leaves the spray-drying chamber is less than about 0.5 wt %. In some embodiments, the acetone content of the dispersion as it leaves the spray-drying chamber is less than about 0.3 wt %. In some embodiments, the acetone content of the dispersion as it leaves the spray-drying chamber is less than about 0.1 wt. A subsequent processing step, such as tray-drying, may be used to remove the solvent to this level.

Pharmaceutical Compositions and Formulations

Such compositions or pharmaceutical compositions, for example, can be in a form such as a tablet, capsule, pill, powder, liquids, suspensions, emulsions, granules, sustained release formulations, solution, and suspension. The pharmaceutical composition may be in an oral formulation suitable for single administration of precise dosages.

The compound of Formula (I) as described herein may be formed into a finished dosage form. The finished dosage form comprises one of more of a liquid, solid or semi-solid dosage forms depending on the route of administration.

The excipients employed in the pharmaceutical compositions can impart good powder flow and compression characteristics to the material being compressed. Desirable characteristics of excipients can include high-compressibilities as to allow for strong tablets to be made at low compression forces; good powder flow properties that can improve the powder flow of other excipients in the composition; and cohesiveness, for example to prevent a tablet from crumbling during processing, shipping, and handling. Such properties are imparted to these excipients through pretreatment steps, such as dry granulation (e.g., by roller compaction, slugging), wet granulation, spray drying spheronization (e.g., spray dried dispersion, solid nanodispersions) or crystallization (e.g., salt forms) of a pharmaceutical composition. They may be classified according to the role that they play in the final tablet. Other excipients which give physical characteristics to a finished tablet are coloring and flavoring agents (e.g., in the case of chewable tablets). Examples of excipients are described, for example, in the *Handbook of Pharmaceutical Excipients* ($5^{th}$ edition), edited by Raymond C. Rowe, Paul J. Sheskey, and Sian C. Owen; Publisher: Pharmaceutical Press.

As described herein, pharmaceutical compositions can also comprise a pharmaceutically acceptable polymer. The pharmaceutically acceptable polymers may be ionic or nonionic. Exemplary pharmaceutically acceptable polymers include polyvinyl pyrrolidone, polyethyleneoxide, polyethylene glycol, poly(vinyl pyrrolidone-co-vinyl acetate), polyoxyethylene-polyoxypropylene block copolymers, graft copolymers comprised of polyethylene glycol, polyvinyl caprolactam and polyvinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate, hydroxypropyl methyl cellulose propionate succinate, hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, carboxymethyl ethylcellulose, hydroxypropyl methylcellulose, hydroxypropyl methylcellulose acetate phthalate, hydroxypropyl methylcellulose propionate phthalate, hydroxypropyl methylcellulose acetate trimellitate, hydroxypropyl methylcellulose propionate trimellitate, cellulose acetate succinate, methyl cellulose acetate succinate, dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1, poly(methacrylic acid-co-methyl methacrylate) 1:2, poly(methacrylic acid-co-ethyl acrylate) 1:1, hydroxyethyl cellulose, methyl cellulose and hydroxy propyl cellulose, poly methacrylic acid-ethyl acrylate, poly methacrylic acid-methyl methacrylate, poly methyl methacrylate-ethyl acrylate, poly trimethylammonioethyl methacrylate chloride-methyl methacrylate-ethyl acrylate and poly(butylmethacrylate-co-(2-dimethylaminoethyl)methacrylate-co-methyl methacrylate), or mixtures thereof. In some embodiments, the pharmaceutically acceptable polymers is selected from the group consisting of polyvinyl pyrrolidone, polyethyleneoxide, polyethylene glycol, poly(vinyl pyrrolidone-co-vinyl acetate), polyoxyethylene-polyoxypropylene block copolymers, graft copolymers comprised of polyethylene glycol, polyvinyl caprolactam and polyvinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate, hydroxypropyl methyl cellulose propionate succinate, hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, carboxymethyl ethylcellulose, hydroxypropyl methylcellulose, hydroxypropyl methylcellulose acetate phthalate, hydroxypropyl methylcellulose propionate phthalate, hydroxypropyl methylcellulose acetate trimellitate, hydroxypropyl methylcellulose propionate trimellitate, cellulose acetate succinate, methyl cellulose acetate succinate, dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1, poly(methacrylic acid-co-methyl methacrylate) 1:2, poly(methacrylic acid-co-ethyl acrylate) 1:1, and mixtures thereof. In some embodiments, the pharmaceutically acceptable polymer is hydroxypropyl methyl cellulose acetate succinate.

The pharmaceutical composition provided herein can contain one or more fillers, which are added, for example, to increase the bulk weight of the blend resulting in a practical size for compression. Fillers that may be used include one or more of calcium salts such as calcium phosphate dibasic and sugars such as lactose, sucrose, dextrose, microcrystalline cellulose, mannitol, and maltodextrin. Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. In some embodiments, the filler is microcrystalline cellulose, which can be manufactured by the controlled hydrolysis of alpha-cellulose. Suitable microcrystalline cellulose will have an average particle size of from about 20 nm to about 200 nm. Suitable microcrystalline cellulose includes Avicel PH 101, Avicel PH 102, Avicel PH 103, Avicel PH 105 and Avicel PH 200, e.g., manufactured by FMC Corporation. In some embodiments, the filler is lactose.

The pharmaceutical composition can also include a lubricant. The term "lubricant" as used herein is typically added to prevent the tableting materials from sticking to punches, minimize friction during tablet compression, and to allow for removal of the compressed tablet from the die. Examples of lubricants include, but are not limited to, colloidal silica, magnesium trisilicate, talc, magnesium carbonate, magnesium oxide, glycerylbehaptate, polyethylene glycol, ethylene oxide polymers (e.g., Carowax), sodium lauryl sulfate, magnesium stearate, aluminum stearate, calcium stearate, sodium stearyl fumarate, stearic acid, magnesium lauryl stearate, and mixtures of magnesium stearate with sodium lauryl sulfate. Exemplary lubricants include calcium stearate, magnesium stearate and sodium stearyl fumarate. In some embodiments, the lubricant is magnesium stearate.

The pharmaceutical composition provided herein can also contain a glidant. The term "glidant" as used herein is a substance added to a powder that can improve its flowability, such as by reducing inter-particle friction. Exemplary glidants include but are not limited to colloidal silicas, colloidal silicon dioxide, fumed silica, CAB-O-SIL® M-5P, AEROSIL®, talc, Syloid*, starch, and magnesium aluminum silicates. In some embodiments, the glidant is silicon dioxide. It should be noted that excipients may serve multiple functions. In some embodiments, the lubricant, for example magnesium stearate, may also function as a glidant.

A disintegrant may be present in an amount necessary to expedite dissolution (e.g., increase the rate of tablet disintegration). The term "disintegrant" as used herein refers to an excipient which can oppose the physical forces of particle bonding in a tablet or capsule when the oral formulation is placed in an aqueous environment. Disintegrants include starch derivatives and salts of carboxymethylcellulose. Examples of pharmaceutically acceptable disintegrants include, but are not limited to, starches, e.g., sodium starch glycolate, pregelatinized starch; clays; celluloses; alginates; gums; cross-linked polymers, e.g., cross-linked polyvinyl pyrrolidone (e.g., Polyplasdone™, polyvinyl polypyrrolidone, crospovidone), cross-linked calcium carboxymethylcellulose and cross-linked sodium carboxymethylcellulose (sodium croscarmellose); and soy polysaccharides. In some embodiments, the disintegrant is crospovidone (e.g, PVP-XL).

In some embodiments, described herein is a pharmaceutical composition comprising a compound represented by Formula (I) and one or more pharmaceutically acceptable carriers, excipients or diluents, wherein the pharmaceutical composition comprises one or more anilinic substances each in an amount equal to or less than about 3.0% by weight based on the weight of the compound of Formula (I). In some embodiments, the one or more anilinic substances is the compound of Formula (II) and is present in the composition in an amount of less than about 1% by weight based on the weight of the compound of Formula (I). In some embodiments, the one or more anilinic substances is the compound of Formula (II) and is present in the composition in an amount of less than about 0.1% by weight to about 0.5% by weight based on the weight of the compound of Formula (I). In some embodiments, the one or more anilinic substances is the compound of Formula (II) and is present in the composition in an amount of less than about 0.01% by weight to about 0.1% by weight based on the weight of the compound of Formula (I). In some embodiments, the composition comprises less than about 1% (w/w) of 3-(5-amino-2-bromo-4-fluorophenyl)-1-ethyl-7-(methylamino)-1,6-naphthyridin-2(1H)-one. In some embodiments, the composition comprises about 0.1% (w/w) to about 0.5% (w/w) of 3-(5-amino-2-bromo-4-fluorophenyl)-1-ethyl-7-(methylamino)-1,6-naphthyridin-2(1H)-one. In some embodiments, the composition comprises about 0.01% (w/w) to about 0.1% (w/w) of 3-(5-amino-2-bromo-4-fluorophenyl)-1-ethyl-7-(methylamino)-1,6-naphthyridin-2(1H)-one.

In some embodiments, the composition further comprises less than 10% by weight of a compound represented by Formula (III):

Formula (III)

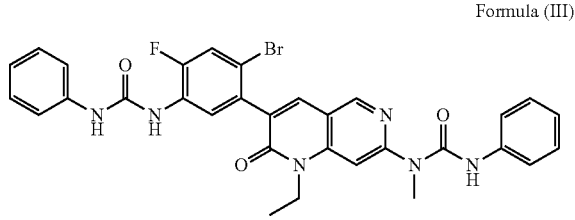 [SMILES: CCn1c(=O)c(-c2cc(NC(=O)Nc3ccccc3)c(F)cc2Br)cc2cnc(N(C)C(=O)Nc3ccccc3)cc21]

based on the weight of the compound of Formula (I).

In some embodiments, the composition further comprises less than 3% by weight of a compound represented by Formula (III):

Formula (III)

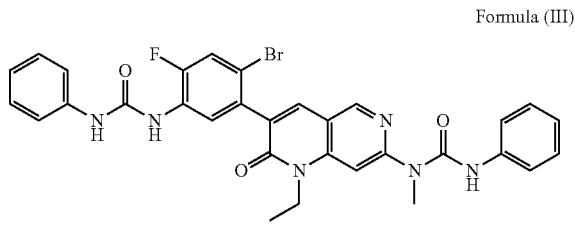

based on the weight of the compound of Formula (I).

In some embodiments, the composition further comprises less than 1% by weight of a compound represented by Formula (III):

Formula (III)

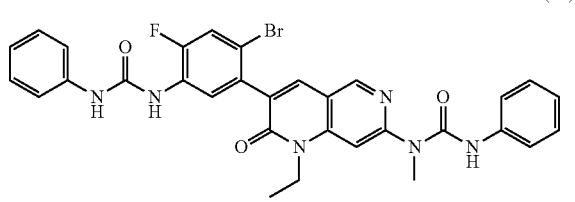

based on the weight of the compound of Formula (I).

In some embodiments, the composition further comprises less than about 0.1% by weight to about 0.5% by weight of a compound represented by Formula (III):

Formula (III)

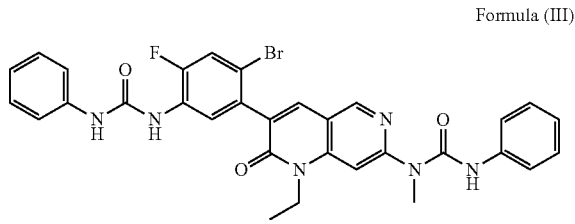 [SMILES: CCn1c(=O)c(-c2cc(NC(=O)Nc3ccccc3)c(F)cc2Br)cc2cnc(N(C)C(=O)Nc3ccccc3)cc21]

based on the weight of the compound of Formula (I).

In some embodiments, the composition further comprises about 0.01% by weight to about 0.1% by weight of a compound represented by Formula (III):

Formula (III)

based on the weight of the compound of Formula (I).

In some embodiments, described herein is a pharmaceutical composition comprising a compound represented by Formula (I) and one or more pharmaceutically acceptable carriers, excipients or diluents, wherein the pharmaceutical composition comprises less than about 10% by weight of a compound represented by Formula (III) based on the weight of the compound of Formula (I). In some embodiments, described herein is a pharmaceutical composition comprising a compound represented by Formula (I) and one or more pharmaceutically acceptable carriers, excipients or diluents, wherein the pharmaceutical composition comprises less than about 7% by weight of a compound represented by Formula (III) based on the weight of the compound of Formula (I). In some embodiments, described herein is a pharmaceutical composition comprising a compound represented by Formula (I) and one or more pharmaceutically acceptable carriers, excipients or diluents, wherein the pharmaceutical composition comprises less than about 5% by weight of a compound represented by Formula (III) based on the weight of the compound of Formula (I). In some embodiments, described herein is a pharmaceutical composition comprising a compound represented by Formula (I) and one or more pharmaceutically acceptable carriers, excipients or diluents, wherein the pharmaceutical composition comprises less than about 3% by weight of a compound represented by Formula (III) based on the weight of the compound of Formula (I). In some embodiments, described herein is a pharmaceutical composition comprising a compound represented by Formula (I) and one or more pharmaceutically acceptable carriers, excipients or diluents, wherein the pharmaceutical composition comprises less than about 1% by weight of a compound represented by Formula (III) based on the weight of the compound of Formula (I). In some embodiments, described herein is a pharmaceutical composition comprising a compound represented by Formula (I) and one or more pharmaceutically acceptable carriers, excipients or diluents, wherein the pharmaceutical composition comprises less than about 0.1% by weight of a compound represented by Formula (III) based on the weight of the compound of Formula (I). In some embodiments, described herein is a pharmaceutical composition comprising a compound represented by Formula (I) and one or more pharmaceutically acceptable carriers, excipients or diluents, wherein the pharmaceutical composition comprises less than about 0.01% by weight of a compound represented by Formula (III) based on the weight of the compound of Formula (I).

In another embodiment, described herein is a pharmaceutical composition comprising the compound of Formula (I) and one or more pharmaceutically acceptable carriers, excipients or diluents, wherein the pharmaceutical composition comprises one or more anilinic substances and a compound represented by Formula (III):

Formula (III)

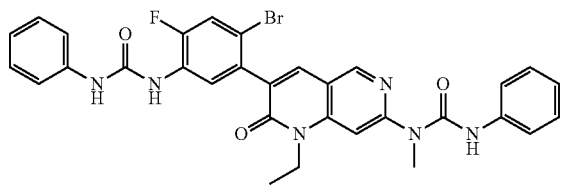

each in an amount equal to or less than 3.0% by weight based on the weight of the compound of Formula (I).

In some embodiments, the composition has equal to or less than about 0.5% by weight one or more anilinic substances based on the weight of the compound of Formula (I). In some embodiments, the composition equal to or less than about 0.3% by weight anilinic substances based on the weight of the compound of Formula (I). In some embodiments, the one or more anilinic substances is selected from the group consisting of a compound represented by Formula (II):

Formula (II)

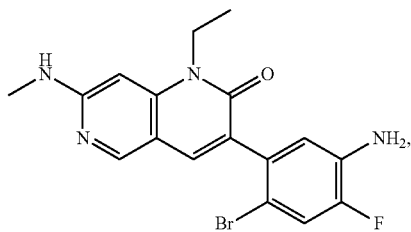

aniline, and a combination thereof. In some embodiments, the one or more anilinic substances is a compound represented by Formula (II):

Formula (II)

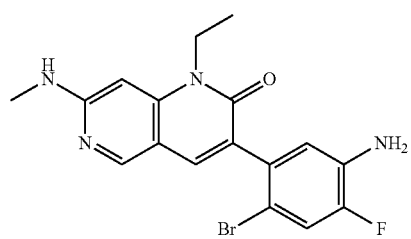

and is present in the composition in an amount of less than about 1% by weight based on the weight of the compound of Formula (I). In some embodiments, the one or more anilinic substances is a compound represented by Formula (II):

Formula (II)

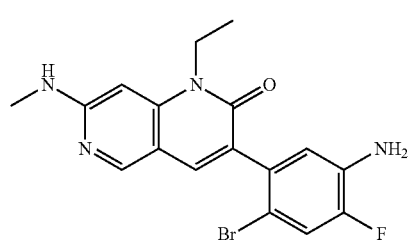

and is present in the composition in an amount of less than about 0.1% by weight to about 0.5% by weight based on the weight of the compound of Formula (I). In some embodiments, the one or more anilinic substances is a compound represented by Formula (II):

Formula (II)

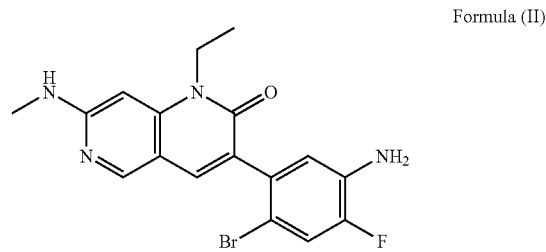 [SMILES: CCn1c(=O)c(-c2cc(N)c(F)cc2Br)cc2cnc(NC)cc21]

and is present in the composition in an amount of less than about 0.01% by weight to about 0.1% by weight based on the weight of the compound of Formula (I). In some embodiments, the compound of Formula (III) is present in the composition in an amount of less than about 1% by weight based on the weight of the compound of Formula (I). In some embodiments, the compound of Formula (III) is present in the composition in an amount of less than about 0.1% by weight to about 0.5% by weight by weight based on the weight of the compound of Formula (I). In some embodiments, the compound of Formula (III) is present in the composition in an amount of less than about 0.01% by weight to about 0.1% by weight by weight based on the weight of the compound of Formula (I).

In some embodiments, described herein is a solid dispersion comprising a compound represented by Formula (I) and one or more pharmaceutically acceptable carriers, excipients or diluents, wherein the solid dispersion comprises one or more anilinic substances each in an amount equal to or less than about 3.0% by weight based on the weight of the compound of Formula (I). In some embodiments, the one or more anilinic substances is the compound of Formula (II) and is present in the composition in an amount of less than about 1% by weight based on the weight of the compound of Formula (I). In some embodiments, the one or more anilinic substances is the compound of Formula (II) and is present in the composition in an amount of less than about 0.1% by weight to about 0.5% by weight based on the weight of the compound of Formula (I). In some embodiments, the one or more anilinic substances is the compound of Formula (II) and is present in the composition in an amount of less than about 0.01% by weight to about 0.1% by weight based on the weight of the compound of Formula (I). In some embodiments, the solid dispersion comprises less than about 1% (w/w) of 3-(5-amino-2-bromo-4-fluorophenyl)-1-ethyl-7-(methylamino)-1,6-naphthyridin-2(1H)-one (the compound of Formula (II). In some embodiments, the solid dispersion comprises about 0.1% (w/w) to about 0.5% (w/w) of 3-(5-amino-2-bromo-4-fluorophenyl)-1-ethyl-7-(methylamino)-1,6-naphthyridin-2(1H)-one (the compound of Formula (II). In some embodiments, the solid dispersion comprises about 0.01% (w/w) to about 0.1% (w/w) of 3-(5-amino-2-bromo-4-fluorophenyl)-1-ethyl-7-(methylamino)-1,6-naphthyridin-2(1H)-one (the compound of Formula (II).

In some embodiments, the solid dispersion further comprises less than 10% by weight of a compound represented by Formula (III):

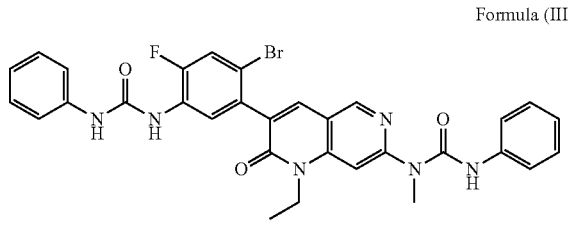

Formula (III)

based on the weight of the compound of Formula (I).

In some embodiments, the solid dispersion further comprises less than 3% by weight of a compound represented by Formula (III):

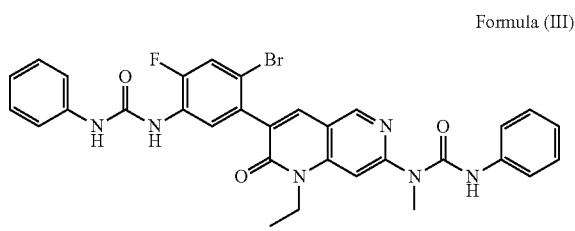 [SMILES: CCn1c(=O)c(-c2cc(NC(=O)Nc3ccccc3)c(F)cc2Br)cc2cnc(N(C)C(=O)Nc3ccccc3)cc21]

Formula (III)

based on the weight of the compound of Formula (I).

In some embodiments, the solid dispersion comprises less than 1% by weight of a compound represented by Formula (III):

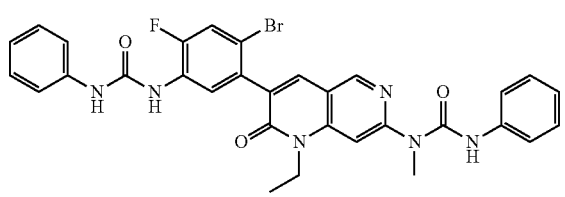

Formula (III)

based on the weight of the compound of Formula (I).

In some embodiments, the solid dispersion comprises less than about 0.1% by weight to about 0.5% by weight of a compound represented by Formula (III):

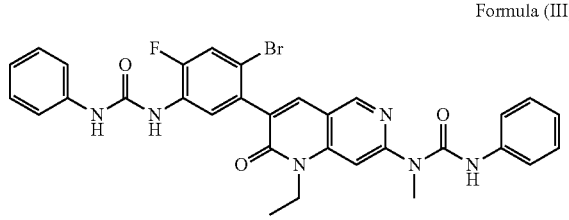

Formula (III)

based on the weight of the compound of Formula (I).

In some embodiments, the solid dispersion comprises about 0.01% by weight to about 0.1% by weight of a compound represented by Formula (III):

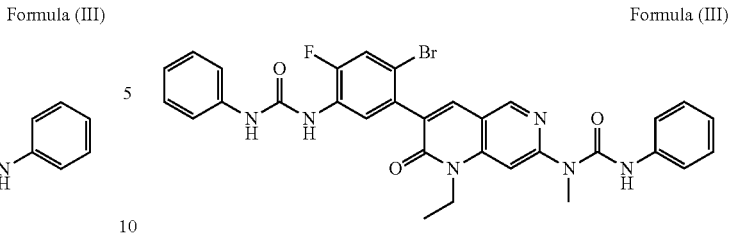

Formula (III)

based on the weight of the compound of Formula (I).

In some embodiments, described herein is a solid dispersion comprising a polymer and a compound represented by Formula (I) and a pharmaceutically acceptable polymer, wherein the solid dispersion comprises one or more anilinic substance, each in an amount equal to or less than about 0.50% by weight based on the weight of the compound of Formula (I). In some embodiments, the one or more anilinic substances is the compound of Formula (II) and is present in the composition in an amount of less than about 0.1% based on the weight of the compound of Formula (I). In some embodiments, the one or more anilinic substances is the compound of Formula (II) and is present in the composition in an amount of less than about 0.01% by weight to about 0.1% by weight based on the weight of the compound of Formula (I). In some embodiments, the solid dispersion comprises about 0.1% (w/w) to about 0.5% (w/w) of 3-(5-amino-2-bromo-4-fluorophenyl)-1-ethyl-7-(methylamino)-1,6-naphthyridin-2(1H)-one (the compound of Formula (II). In some embodiments, the solid dispersion comprises about 0.01% (w/w) to about 0.1% (w/w) of 3-(5-amino-2-bromo-4-fluorophenyl)-1-ethyl-7-(methylamino)-1,6-naphthyridin-2(1H)-one (the compound of Formula (II)).

In some embodiments, the solid dispersion further comprises less than about 0.1% by weight to about 0.5% by weight of a compound represented by Formula (III):

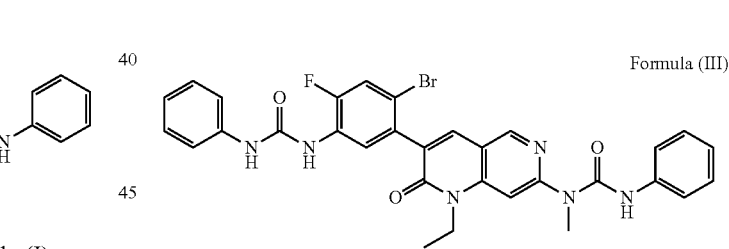

Formula (III)

based on the weight of the compound of Formula (I).

In some embodiments, the solid dispersion further comprises about 0.01% by weight to about 0.1% by weight of a compound represented by Formula (III):

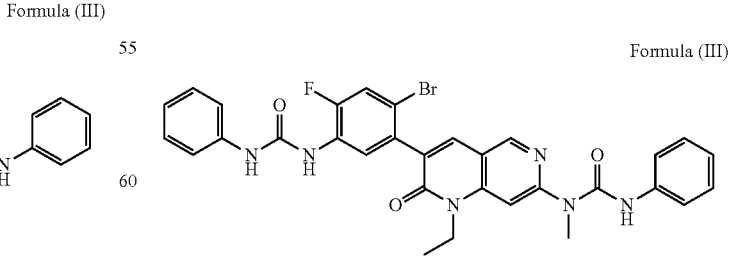

Formula (III)

based on the weight of the compound of Formula (I).

In some embodiments, the solid dispersion comprises from about 10% to about 50%, or from about 10% to about 30%, or from about 20% to about 30%, by weight of the compound represented by Formula (I) based on the total weight of the solid dispersion. In some embodiments, the pharmaceutical compositions may comprise about 25% by weight of the compound represented by Formula (I) based on the total weight of the solid dispersion.

The solid dispersion provided herein comprises, in some embodiments, a pharmaceutically acceptable polymer selected from the group consisting of polyvinyl pyrrolidone, polyethyleneoxide, polyethylene glycol, poly(vinyl pyrrolidone-co-vinyl acetate), polyoxyethylene-polyoxypropylene block copolymers, graft copolymers comprised of polyethylene glycol, polyvinyl caprolactam and polyvinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate, hydroxypropyl methyl cellulose propionate succinate, hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, carboxymethyl ethylcellulose, hydroxypropyl methylcellulose, hydroxypropyl methylcellulose acetate phthalate, hydroxypropyl methylcellulose propionate phthalate, hydroxypropyl methylcellulose acetate trimellitate, hydroxypropyl methylcellulose propionate trimellitate, cellulose acetate succinate, methyl cellulose acetate succinate, dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1, poly(methacrylic acid-co-methyl methacrylate) 1:2, poly(methacrylic acid-co-ethyl acrylate) 1:1, hydroxyethyl cellulose, methyl cellulose and hydroxy propyl cellulose, poly methacrylic acid-ethyl acrylate, poly methacrylic acid-methyl methacrylate, poly methyl methacrylate-ethyl acrylate, poly trimethylammonioethyl methacrylate chloride-methyl methacrylate-ethyl acrylate and poly(butylmethacrylate-co-(2-dimethylaminoethyl)methacrylate-co-methyl methacrylate), and mixtures thereof. The solid dispersion provided herein comprises, in some embodiments, a pharmaceutically acceptable polymer selected from the group consisting of polyvinyl pyrrolidone, polyethyleneoxide, polyethylene glycol, poly(vinyl pyrrolidone-co-vinyl acetate), polyoxyethylene-polyoxypropylene block copolymers, graft copolymers comprised of polyethylene glycol, polyvinyl caprolactam and polyvinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate, hydroxypropyl methyl cellulose propionate succinate, hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, carboxymethyl ethylcellulose, hydroxypropyl methylcellulose, hydroxypropyl methylcellulose acetate phthalate, hydroxypropyl methylcellulose propionate phthalate, hydroxypropyl methylcellulose acetate trimellitate, hydroxypropyl methylcellulose propionate trimellitate, cellulose acetate succinate, methyl cellulose acetate succinate, dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1, poly(methacrylic acid-co-methyl methacrylate) 1:2, poly(methacrylic acid-co-ethyl acrylate) 1:1, and mixtures thereof. For example, the pharmaceutically acceptable polymer in the formulation provided herein is hydroxypropyl methyl cellulose acetate succinate.

In some embodiments, the solid dispersion comprises the compound represented by Formula (I) and the pharmaceutically acceptable polymer in a ratio from about 40:60 to about 10:90 or from about 30:70 to about 20:80. In some embodiments, the compound represented by Formula (I) and the pharmaceutically acceptable polymer may be in a ratio of about 25:75.

Also provided herein is a pharmaceutical composition comprising: (a) an intragranular blend comprising: (i) a solid spray-dried dispersion comprising a compound represented by Formula (I), and a pharmaceutically acceptable polymer; (ii) one or more fillers; (iii) a disintegrant; (iv) a glidant; and (v) a lubricant; and (b) an extragranular blend comprising: (i) a glidant; and (ii) a lubricant.

In some embodiments, the blend of the internal and extragranular blends is in a ratio of from about 90:10 to about 99.5:0.5. For example, the blend of the internal and extragranular blends may be in a ratio of about 99:1.

In some embodiments, the solid dispersion of the intragranular blend comprises from about 10% to about 50%, or from about 10% to about 30%, or from about 20% to about 30% by weight of the compound represented by Formula (I) based on the total weight of the solid spray-dried dispersion. In some embodiments, the solid spray-dried dispersion may comprise about 25% by weight of the compound represented by Formula (I) based on the total weight of the solid spray-dried dispersion.

In some embodiments, the pharmaceutical composition comprises a pharmaceutically acceptable polymer selected from the group consisting of polyvinyl pyrrolidone, polyethyleneoxide, polyethylene glycol, poly(vinyl pyrrolidone-co-vinyl acetate), polyoxyethylene-polyoxypropylene block copolymers, graft copolymers comprised of polyethylene glycol, polyvinyl caprolactam and polyvinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate, hydroxypropyl methyl cellulose propionate succinate, hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, carboxymethyl ethylcellulose, hydroxypropyl methylcellulose, hydroxypropyl methylcellulose acetate phthalate, hydroxypropyl methylcellulose propionate phthalate, hydroxypropyl methylcellulose acetate trimellitate, hydroxypropyl methylcellulose propionate trimellitate, cellulose acetate succinate, methyl cellulose acetate succinate, dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1, poly(methacrylic acid-co-methyl methacrylate) 1:2, poly(methacrylic acid-co-ethyl acrylate) 1:1, hydroxyethyl cellulose, methyl cellulose and hydroxy propyl cellulose, poly methacrylic acid-ethyl acrylate, poly methacrylic acid-methyl methacrylate, poly methyl methacrylate-ethyl acrylate, poly trimethylammonioethyl methacrylate chloride-methyl methacrylate-ethyl acrylate and poly(butylmethacrylate-co-(2-dimethylaminoethyl)methacrylate-co-methyl methacrylate), and mixtures thereof. In some embodiments, the pharmaceutical composition comprises a pharmaceutically acceptable polymer selected from the group consisting of polyvinyl pyrrolidone, polyethyleneoxide, polyethylene glycol, poly(vinyl pyrrolidone-co-vinyl acetate), polyoxyethylene-polyoxypropylene block copolymers, graft copolymers comprised of polyethylene glycol, polyvinyl caprolactam and polyvinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate, hydroxypropyl methyl cellulose propionate succinate, hydroxypropyl methyl cellulose phthalate, cellulose acetate phthalate, cellulose acetate trimellitate, methyl cellulose acetate phthalate, hydroxypropyl cellulose acetate phthalate, cellulose acetate terephthalate, cellulose acetate isophthalate, carboxymethyl ethylcellulose, hydroxypropyl methylcellulose, hydroxypropyl methylcellulose acetate phthalate, hydroxypropyl methylcellulose propionate phthalate, hydroxypropyl methylcellulose acetate trimellitate, hydroxypropyl methylcellulose propionate trimellitate, cellulose acetate succinate, methyl cellulose acetate succinate, dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1, poly(methacrylic acid-co-methyl methacrylate) 1:2, poly(methacrylic acid-co-ethyl acrylate) 1:1, and mixtures thereof. For example, the pharmaceutically acceptable polymer is hydroxypropyl methyl cellulose acetate succinate.

In some embodiments, the pharmaceutical composition comprises the compound represented by Formula (I) and the pharmaceutically acceptable polymer in a ratio from about 40:60 to about 10:90, or from about 30:70 to about 20:80. In some embodiments, the compound represented by Formula (I) and the pharmaceutically acceptable polymer may be in a ratio of about 25:75.

In some embodiments, the intragranular blend of the pharmaceutical composition comprises one or more fillers, wherein the total amount of the one or more fillers is from about 40% to about 80% by weight based on the total weight of the pharmaceutical composition. One or more fillers are lactose, maltodextrin, mannitol, microcrystalline cellulose, pregelatinized starch, sucrose esters, or hydrates thereof. In some embodiments, the intragranular blend comprises two fillers. When the intragranular blend comprises two fillers, each filler may independently be present in an amount from about 20% to about 40%, e.g., about 33%, by weight based on the total weight of the pharmaceutical composition. In some embodiments, one filler may be microcrystalline cellulose and the other filler may be lactose monohydrate.

In some embodiments, the intragranular blend of the pharmaceutical composition comprises from about 1% to about 10% by weight, e.g., about 5%, of the disintegrant based on the total weight of the pharmaceutical composition. The disintegrant is crospovidone, croscarmellose sodium, sodium starch glycolate, microcrystalline cellulose, or pregelatinized starch. In some embodiments, the disintegrant in the intragranular blend may be crospovidone.

In some embodiments, the glidant of the intragranular blend is present in an amount from about 0.1% to about 1%, e.g., about 0.5%, based on the total weight of the pharmaceutical composition. For example, the glidant of the intragranular blend may be silicon dioxide.

In some embodiments, the glidant of the extragranular blend is present in an amount from about 0.1% to about 1%, e.g., about 0.5%, based on the total weight of the pharmaceutical composition. In some embodiments, the glidant of the extragranular blend may be silicon dioxide.

In some embodiments, the lubricant of the intragranular blend is present in an amount from about 0.1% to about 1%, e.g., about 0.5%, based on the total weight of the pharmaceutical composition. In some embodiments, the lubricant of the intragranular blend is magnesium stearate, calcium stearate, glyceryl monostearate, hydrogenated castor oil, sodium lauryl sulfate, sodium stearyl fumarate, stearic acid, zinc stearate, talc, microcrystalline cellulose, or sucrose esters. For example, the lubricant of the intragranular blend may be magnesium stearate.

In some embodiments, the lubricant of the extragranular blend is present in an amount from about 0.1% to about 1%, e.g., about 0.5%, based on the total weight of the pharmaceutical composition. In some embodiments, the lubricant of the extragranular blend is magnesium stearate, calcium stearate, glyceryl monostearate, hydrogenated castor oil, sodium lauryl sulfate, sodium stearyl fumarate, stearic acid, zinc stearate, talc, microcrystalline cellulose, or sucrose esters. As an example, the lubricant of the extragranular blend may be magnesium stearate.

In some embodiments, the composition comprises less than or equal to about 10% by weight of one or more anilinic substances based on the weight of the compound of Formula (I). In some embodiments, the composition comprises less than or equal to about 7% by weight of one or more anilinic substances based on the weight of the compound of Formula (I). In some embodiments, the composition comprises less than or equal to about 5% by weight of one or more anilinic substances based on the weight of the compound of Formula (I). In some embodiments, the composition comprises less than or equal to about 3% by weight of one or more anilinic substances based on the weight of the compound of Formula (I). In some embodiments, the composition comprises less than about 10% by weight of 3-(5-amino-2-bromo-4-fluorophenyl)-1-ethyl-7-(methylamino)-1,6-naphthyridin-2 (1H)-one (the compound of Formula (II)) based on the weight of the compound of Formula (I). In some embodiments, the composition comprises less than about 7% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the composition comprises less than about 5% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the composition comprises less than about 3% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the composition comprises less than about 2% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the composition comprises less than about 1% by weight of 3-(5-amino-2-bromo-4-fluorophenyl)-1-ethyl-7-

(methylamino)-1,6-naphthyridin-2(1H)-one (the compound of Formula (II)) based on the weight of the compound of Formula (I). In some embodiments, the composition comprises about 0.1% by weight to about 0.5% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the composition comprises about 0.01% by weight to about 0.1% by weight of 3-(5-amino-2-bromo-4-fluorophenyl)-1-ethyl-7-(methylamino)-1,6-naphthyridin-2(1H)-one (the compound of Formula (II) based on the weight of the compound of Formula (I).

In some embodiments, the composition comprises less than 10% by weight of a compound represented by Formula (III):

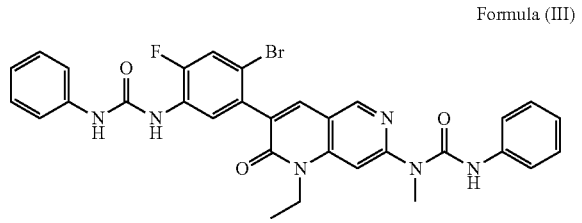 [SMILES: CCn1c(=O)c(-c2cc(NC(=O)Nc3ccccc3)c(F)cc2Br)cc2cnc(N(C)C(=O)Nc3ccccc3)cc21]

Formula (III)

based on the weight of the compound of Formula (I).

In some embodiments, the composition comprises less than 7% by weight of a compound represented by Formula (III):

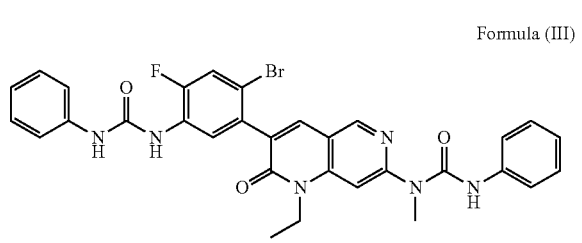 [SMILES: CCn1c(=O)c(-c2cc(NC(=O)Nc3ccccc3)c(F)cc2Br)cc2cnc(N(C)C(=O)Nc3ccccc3)cc21]

Formula (III)

based on the weight of the compound of Formula (I).

In some embodiments, the composition comprises less than 5% by weight of a compound represented by Formula (III):

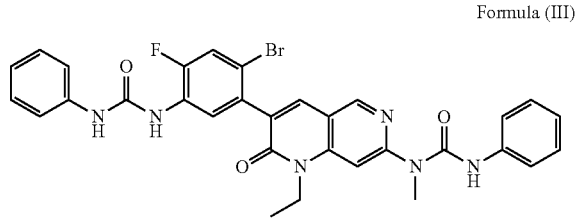 [SMILES: CCn1c(=O)c(-c2cc(NC(=O)Nc3ccccc3)c(F)cc2Br)cc2cnc(N(C)C(=O)Nc3ccccc3)cc21]

Formula (III)

based on the weight of the compound of Formula (I).

In some embodiments, the composition comprises less than 3% by weight of a compound represented by Formula (III):

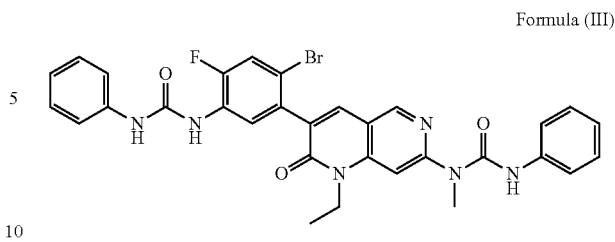

Formula (III)

based on the weight of the compound of Formula (I).

In some embodiments, the composition comprises less than 1% by weight of a compound represented by Formula (III):

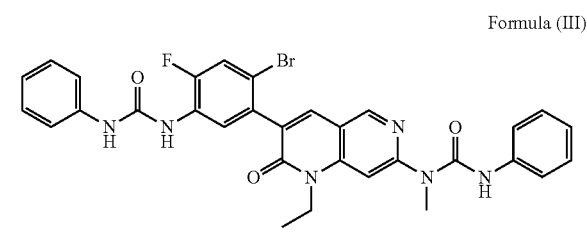 [SMILES: CCn1c(=O)c(-c2cc(NC(=O)Nc3ccccc3)c(F)cc2Br)cc2cnc(N(C)C(=O)Nc3ccccc3)cc21]

Formula (III)

based on the weight of the compound of Formula (I).

In some embodiments, the composition comprises less than about 0.1% by weight to about 0.5% by weight of a compound represented by Formula (III):

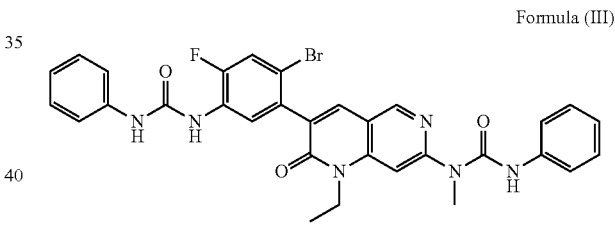

Formula (III)

based on the weight of the compound of Formula (I).

In some embodiments, the composition comprises about 0.01% by weight to about 0.1% by weight of a compound represented by Formula (III):

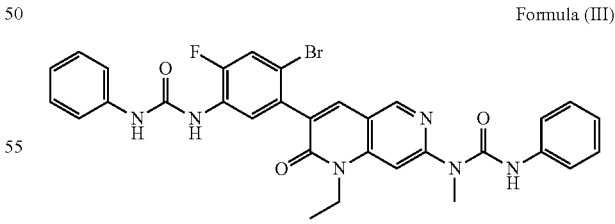

Formula (III)

based on the weight of the compound of Formula (I).

In some embodiments, provided herein is a pharmaceutical composition comprising: (a) an intragranular blend comprising: (i) about 33% by weight of a solid spray-dried dispersion based on the total weight of the pharmaceutical composition, the solid spray-dried dispersion comprising a compound represented by Formula (I) having a purity by HPLC of greater than 95% and hydroxypropyl methyl cellulose acetate succinate, wherein the solid spray-dried dispersion comprises about 25% by weight of the compound represented by Formula (I) based on the total weight of the solid spray-dried dispersion; (ii) about 30% by weight of microcrystalline cellulose based on the total amount of the of the pharmaceutical composition; (iii) about 30% by weight of lactose monohydrate based on the total amount of the of the pharmaceutical composition; (iv) about 5% by weight of crospovidone based on the total amount of the of the pharmaceutical composition; (v) about 0.5% by weight of silicon dioxide based on the total amount of the of the pharmaceutical composition; and (vi) about 0.5% by weight of magnesium stearate based on the total amount of the of the pharmaceutical composition; and (b) an extragranular blend comprising: (i) about 0.5% by weight of silicon dioxide based on the total amount of the of the pharmaceutical composition; and (ii) about 0.5% by weight of magnesium stearate based on the total amount of the of the pharmaceutical composition.

In some embodiments, provided herein is a pharmaceutical composition comprising: (a) an intragranular blend comprising: (i) about 200 mg of a solid spray-dried dispersion comprising a compound represented by Formula (I) and hydroxypropyl methyl cellulose acetate succinate, wherein the solid spray-dried dispersion comprises about 50 mg of the compound represented by Formula (I); (ii) about 179 mg of microcrystalline cellulose; (iii) about 179 mg of lactose monohydrate; (iv) about 30 mg of crospovidone; (v) about 3 mg of silicon dioxide; and (vi) about 3 mg of magnesium stearate; and (b) an extragranular blend comprising: (i) about 3 mg of silicon dioxide; and (ii) about 3 mg of magnesium stearate.

The pharmaceutical compositions may also be provided as tablets. Tablets may be uncoated, film, or sugar coated bisected, embossed, plain, layered, or sustained-release. They can be made in a variety of sizes, shapes, and colors. Tablets may be swallowed, chewed, or dissolved in the buccal cavity or beneath the tongue.

In some embodiments, provided herein is a tablet providing about 50 mg of a compound represented by Formula (I), wherein the tablet comprises: (a) an intragranular blend comprising: (i) about 195 mg to about 205 mg of a solid spray-dried dispersion that comprises about 50 mg of the compound and hydroxypropyl methyl cellulose acetate succinate; (ii) about 177 mg to about 181 mg of microcrystalline cellulose; (iii) about 177 mg to about 181 mg of lactose monohydrate; and (iv) about 28 mg to about 32 mg of crospovidone; and (b) an extragranular blend comprising: (i) about 2 mg to about 4 mg of silicon dioxide; and (ii) about 2 mg to about 4 mg of magnesium stearate.

In some embodiments, the tablet comprises less than or equal to about 10% by weight of one or more anilinic substances based on the weight of the compound of Formula (I). In some embodiments, the tablet comprises less than or equal to about 7% by weight of one or more anilinic substances based on the weight of the compound of Formula (I). In some embodiments, the tablet comprises less than or equal to about 5% by weight of one or more anilinic substances based on the weight of the compound of Formula (I). In some embodiments, the tablet comprises less than or equal to about 3% by weight of one or more anilinic substances based on the weight of the compound of Formula (I). In some embodiments, the tablet comprises less than about 10% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the tablet comprises less than about 7% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the tablet comprises less than about 5% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the tablet comprises less than about 3% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the tablet comprises less than about 2% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the tablet comprises less than about 1% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the tablet comprises about 0.1% by weight to about 0.5% by weight of 3-(5-amino-2-bromo-4-fluorophenyl)-1-ethyl-7-(methylamino)-1,6-naphthyridin-2(1H)-one (the compound of Formula (II)) based on the weight of the compound of Formula (I). In some embodiments, the tablet comprises about 0.01% by weight to about 0.1% by weight of 3-(5-amino-2-bromo-4-fluorophenyl)-1-ethyl-7-(methylamino)-1,6-naphthyridin-2 (1H)-one (the compound of Formula (II) based on the weight of the compound of Formula (I).

In some embodiments, the tablet comprises less than 10% by weight of a compound represented by Formula (III):

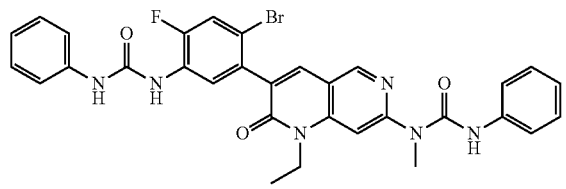

Formula (III)

based on the weight of the compound of Formula (I).

In some embodiments, the tablet comprises less than 7% by weight of a compound represented by Formula (III):

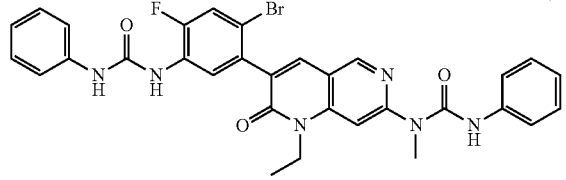

Formula (III)

based on the weight of the compound of Formula (I).

In some embodiments, the tablet comprises less than 5% by weight of a compound represented by Formula (III):

Formula (III)

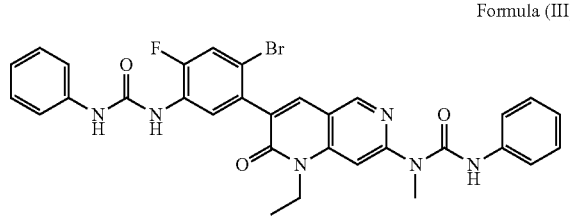

based on the weight of the compound of Formula (I).

In some embodiments, the tablet comprises less than 3% by weight of a compound represented by Formula (III):

Formula (III)

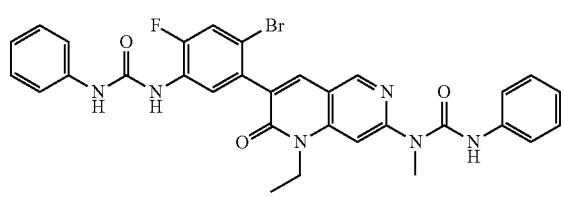

based on the weight of the compound of Formula (I).

In some embodiments, the tablet comprises less than 1% by weight of a compound represented by Formula (III):

Formula (III)

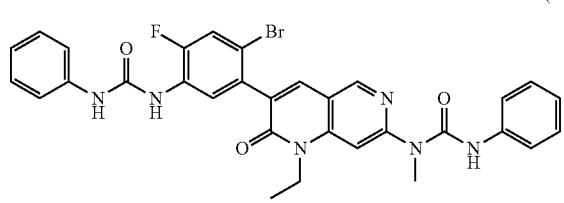

based on the weight of the compound of Formula (I).

In some embodiments, the tablet comprises less than about 0.1% by weight to about 0.5% by weight of a compound represented by Formula (III):

Formula (III)

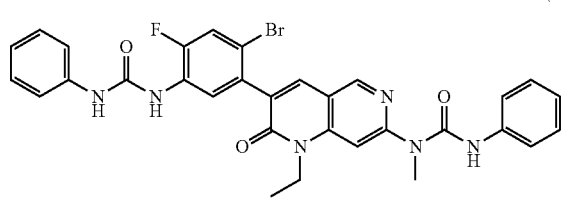

based on the weight of the compound of Formula (I).

In some embodiments, the tablet comprises about 0.01% by weight to about 0.1% by weight of a compound represented by Formula (III):

Formula (III)

based on the weight of the compound of Formula (I).

Methods of Treatment

A pharmaceutical composition comprising a compound of Formula (I) and one or more pharmaceutically acceptable carriers, excipients or diluents, wherein the pharmaceutical composition comprises one or more anilinic substances each present in an amount equal to or less than about 3.0% by weight based on the weight of the compound of Formula (I) as described herein is a broad-spectrum inhibitor of c-KIT.

Disorders that can be treated be the compound of Formula (I) include, but are not limited to: gastrointestinal stromal tumors (GIST), NF-1-deficient gastrointestinal stromal tumors, succinate dehydrogenase (SDH)-deficient gastrointestinal stromal tumors, KIT driven gastrointestinal stromal tumors, PDGFRA driven gastrointestinal stromal tumors, melanoma, acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, non-small cell lung cancer, lung cancer, glioblastoma, a glioma, malignant peripheral nerve sheath sarcoma, hypereosinophilic syndrome, KIT driven germ cell tumor (e.g., testicular germ cell), KIT driven skin cancer, KIT driven renal cell carcinoma, penile cancer, PDGFRA driven penile cancer, prostate cancer, PDGFRA driven prostate cancer, PDGFRA driven non-melanoma skin cancer, PDGFRA driven glioma, PDGFRA driven sarcoma, PDGFRA driven glioblastoma, PDGFRA driven pancreatic cancer, or a disease vaginal cancer, prostate cancer, penile cancer, non-melanoma skin cancer, melanoma, or breast sarcoma (e.g., a vaginal cancer, prostate cancer, penile cancer, non-melanoma skin cancer, melanoma, or breast sarcoma comprising a PDGFRB mutation).

Accordingly, provided herein, in another embodiment, is a method of treating a disease selected from the group consisting of gastrointestinal stromal tumors (GIST), KIT driven gastrointestinal stromal tumors, PDGFRA driven gastrointestinal stromal tumors, melanoma, acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer in a patient in need thereof, comprising administering to the patient a therapeutically effective amount of a composition described herein.

Also provided herein, in another embodiment, is a method of treating a disease selected from the group consisting of gastrointestinal stromal tumors (GIST), KIT driven gastrointestinal stromal tumors, PDGFRA driven gastrointestinal stromal tumors, lung cancer, glioblastoma, a glioma, malignant peripheral nerve sheath sarcoma, and hypereosinophilic syndrome in a patient in need thereof, comprising administering to the patient a therapeutically effective amount of a composition described herein. In some embodiments, the disease is gastrointestinal stromal tumors (GIST).

Also provided herein, in another embodiment, is a method of treating a disease selected from the group consisting of KIT driven germ cell tumor (e.g., testicular germ cell), KIT driven skin cancer, or KIT driven renal cell carcinoma in a patient in need thereof, comprising administering to the patient a therapeutically effective amount of a composition described herein.

Also provided herein, in another embodiment, is a method of treating a disease selected from the group consisting of penile cancer, PDGFRA driven penile cancer, prostate cancer, PDGFRA driven prostate cancer, PDGFRA driven non-melanoma skin cancer, PDGFRA driven glioma, PDGFRA driven sarcoma, PDGFRA driven glioblastoma, or PDGFRA driven pancreatic cancer in a patient in need thereof, comprising administering to the patient a therapeutically effective amount of a composition described herein.

Also provided herein, in another embodiment, is a method of treating a disease comprising a PDGFRB mutation selected from the group consisting of vaginal cancer, prostate cancer, penile cancer, non-melanoma skin cancer, melanoma, or breast sarcoma in a patient in need thereof, comprising administering to the patient a therapeutically effective amount of a composition described herein.

In some embodiments, provided herein is a method for treating diseases driven by KIT mutations or PDGFRA mutations in a patient in need thereof, comprising administering to the patient a therapeutically effective amount of a composition or one or more tablets described herein. In some embodiments, provided herein is a method for treating diseases driven by KIT mutations and PDGFRA mutations in a patient in need thereof, comprising administering to the patient a therapeutically effective amount of a composition or one or more tablets described herein. In some embodiments, provided herein is a method for treating diseases driven by KIT mutations or PDGFRA mutations, comprising passenger PDGFRB mutations in a patient in need thereof, comprising administering to the patient a therapeutically effective amount of a composition described herein.

In some embodiments, provided herein is a method for treating a disease selected from the group consisting of gastrointestinal stromal tumors (GIST), KIT driven gastrointestinal stromal tumors, PDGFRA driven gastrointestinal stromal tumors, melanoma (e.g., KIT driven melanoma or PGDFRA driven melanoma or PGDFR driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer in a patient in need thereof, comprising administering to the patient a therapeutically effective amount of a composition or one or more tablets described herein. In some embodiments, the melanoma is cutaneous melanoma or noncutaneous melanaoma. In some embodiments, the melanoma is cutaneous melanoma. In some embodiments, the cutaneous melanoma is superficial spreading melanoma, nodular melanoma, acral-lentiginous melanoma, or amelanotic and desmoplastic melanoma. In some embodiments, the melanoma is noncutaneous (non-skin) melanoma. In some embodiments, the noncutaneous melanoma is ocular melanoma or mucosal melanoma. In some embodiments, the disease is caused by the kinase activity of c-KIT and/or PDGFRA, and/or oncogenic forms thereof. In some embodiments, the disease is selected from the group consisting of KIT driven germ cell tumor (e.g., testicular germ cell), KIT driven skin cancer (e.g., KIT driven cutaneous squamous cell carcinoma, KIT driven Merkel cell carcinoma, uveal melanoma, non-melanoma skin cancer), or KIT driven renal cell carcinoma (e.g., renal cell carcinoma, chromophobe renal cell carcinoma). In some embodiments, the disease is selected from the group consisting of penile cancer, PDGFRA driven penile cancer, prostate cancer, PDGFRA driven prostate cancer, PDGFRA driven non-melanoma skin cancer, PDGFRA driven glioma, PDGFRA driven sarcoma, PDGFRA driven glioblastoma, or PDGFRA driven pancreatic cancer. In some embodiments, the disease comprising a PDGFRB mutation is selected from the group consisting of vaginal cancer, prostate cancer, penile cancer, non-melanoma skin cancer, melanoma, or breast sarcoma.

Also provided herein, in another embodiment, is a use of a composition described herein for the preparation of a medicament for the treatment of a disease selected from the group consisting of gastrointestinal stromal tumors (GIST), KIT driven gastrointestinal stromal tumors, PDGFRA driven gastrointestinal stromal tumors, melanoma, acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer. In some embodiments, the preparation of a medicament for the treatment of a disease selected from the group consisting of gastrointestinal stromal tumors (GIST), KIT driven gastrointestinal stromal tumors, PDGFRA driven gastrointestinal stromal tumors, lung cancer, glioblastoma, a glioma, malignant peripheral nerve sheath sarcoma, and hypereosinophilic syndrome.

In some embodiments, provided herein is a method of treating a disease selected from the group consisting of gastrointestinal stromal tumors (GIST), KIT driven gastrointestinal stromal tumors, PDGFRA driven gastrointestinal stromal tumors, melanoma (e.g., cutaneous melanoma, non-cutaneous melanoma, KIT driven melanoma or PGDFRA driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer, comprising administering to a patient in need thereof a therapeutically effective amount of a pharmaceutical composition comprising a compound of Formula (I) and one or more pharmaceutically acceptable carriers, excipients or diluents, wherein the pharmaceutical composition comprises one or more anilinic substances each present in an amount equal to or less than about 3.0% by weight based on the weight of the compound of Formula (I). In some embodiments, the disease is caused by the kinase activity of: c-KIT and/or PDGFRA, and/or oncogenic forms thereof. In some embodiments, the disease is gastrointestinal stromal tumors (GIST). In some embodiments, the disease is KIT driven gastrointestinal stromal tumors. In some embodiments, the disease is PDGFRA driven gastrointestinal stromal tumors. In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, provided herein, is a method of treating or preventing a PDGFR kinase-mediated tumor growth of tumor progression comprising administering to a patient in need thereof a therapeutically effective amount of the pharmaceutical composition comprising a compound of Formula (I) and one or more pharmaceutically acceptable carriers, excipients or diluents, wherein the pharmaceutical composition comprises one or more anilinic substances each present in an amount equal to or less than about 3.0% by weight based on the weight of the compound of Formula (I). In some embodiments, the tumor growth or tumor progression is caused by PDGFRα kinase overexpression, oncogenic PDGFRα missense mutations, oncogenic deletion PDGFRα mutations, oncogenic PDGFRα gene rearrangements leading to PDGFRα fusion proteins, PDGFRα intragenic in-frame deletions, and/or oncogenic PDGFRα gene amplification. In some embodiments, a pharmaceutical composition comprising a compound of Formula (I) and one or more pharmaceutically acceptable carriers, excipients or diluents, wherein the pharmaceutical composition comprises one or more anilinic substances each present in an amount equal to or less than about 3.0% by weight based on the weight of the compound of Formula (I) is administered to a cancer patient wherein the cancer is PDGFRA driven gastrointestinal stromal tumors, lung adenocarcinoma, squamous cell lung cancer, glioblastoma, glioma, pediatric glioma, astrocytomas, sarcomas, gastrointestinal stromal tumors, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, or lymphoblastic T-cell lymphoma. In some embodiments, the disease is PDGFRA driven gastrointestinal stromal tumors (GIST). In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, a pharmaceutical composition comprising a compound of Formula (I) and one or more pharmaceutically acceptable carriers, excipients or diluents, wherein the pharmaceutical composition comprises one or more anilinic substances each present in an amount equal to or less than about 3.0% by weight based on the weight of the compound of Formula (I) is administered as a single agent or in combination with other cancer targeted therapeutic agents, cancer-targeted biologicals, immune checkpoint inhibitors, or chemotherapeutic agents.

In some embodiments, the methods of treatment described herein comprise administering a composition of the compound of Formula (I) described herein, to a subject in need thereof prior to surgery (as a neoadjuvant therapy). In some embodiments, the methods of treatment described herein comprise administering a composition of the compound of Formula (I) described herein, to a subject in need thereof after to surgery (as an adjuvant therapy).

A solid dispersion comprising a compound of Formula (I) and a pharmaceutically acceptable polymer, wherein the pharmaceutical composition comprises one or more anilinic substances each present in an amount equal to or less than about 3.0% by weight based on the weight of the compound of Formula (I) as described herein is a broad-spectrum inhibitor of c-KIT. In some embodiments, provided herein is a method of treating a disease selected from the group consisting of gastrointestinal stromal tumors (GIST), KIT driven gastrointestinal stromal tumors, PDGFRA driven gastrointestinal stromal tumors, melanoma (e.g., cutaneous melanoma, noncutaneous melanoma, KIT driven melanoma or PGDFRA driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer, comprising administering to a patient in need thereof a therapeutically effective amount of the solid dispersion comprising a compound of Formula (I) and a pharmaceutically acceptable polymer, wherein the pharmaceutical composition comprises one or more anilinic substances each present in an amount equal to or less than about 3.0% by weight based on the weight of the compound of Formula (I). In some embodiments, the disease is caused by the kinase activity of c-KIT and/or PDGFRA, and/or oncogenic forms thereof. In some embodiments, the disease is gastrointestinal stromal tumors (GIST). In some embodiments, the disease is KIT driven gastrointestinal stromal tumors. In some embodiments, the disease is PDGFRA driven gastrointestinal stromal tumors. In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, provided herein, is a method of treating or preventing a PDGFR kinase-mediated tumor growth of tumor progression comprising administering to a patient in need thereof a therapeutically effective amount of a solid dispersion comprising a compound of Formula (I) and a pharmaceutically acceptable polymer, wherein the pharmaceutical composition comprises one or more anilinic substances each present in an amount equal to or less than about 3.0% by weight based on the weight of the compound of Formula (I). In some embodiments, the tumor growth or tumor progression is caused by PDGFRα kinase overexpression, oncogenic PDGFRα missense mutations, oncogenic deletion PDGFRα mutations, oncogenic PDGFRα gene rearrangements leading to PDGFRα fusion proteins, PDGFRα intragenic in-frame deletions, and/or oncogenic PDGFRα gene amplification. In some embodiments, a solid dispersion comprising a compound of Formula (I) and a pharmaceutically acceptable polymer, wherein the pharmaceutical composition comprises one or more anilinic substances each present in an amount equal to or less than about 3.0% by weight based on the weight of the compound of Formula (I) is administered to a cancer patient wherein the cancer is PDGFRA driven gastrointestinal stromal tumors, lung adenocarcinoma, squamous cell lung cancer, glioblastoma, glioma, pediatric glioma, astrocytomas, sarcomas, gastrointestinal stromal tumors, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, or lymphoblastic T-cell lymphoma. In some embodiments, the disease is PDGFRA driven gastrointestinal stromal tumors (GIST). In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, a solid dispersion comprising a compound of Formula (I) and a pharmaceutically acceptable polymer, wherein the pharmaceutical composition comprises one or more anilinic substances each present in an amount equal to or less than about 3.0% by weight based on the weight of the compound of Formula (I) is administered as a single agent or in combination with other cancer targeted therapeutic agents, cancer-targeted biologicals, immune checkpoint inhibitors, or chemotherapeutic agents.

A solid dispersion comprising a compound of Formula (I) and a pharmaceutically acceptable polymer, having a purity by HPLC of greater than about 95% as described herein is a broad-spectrum inhibitor of c-KIT. In some embodiments, provided herein is a method of treating a disease selected from the group consisting of gastrointestinal stromal tumors (GIST), KIT driven gastrointestinal stromal tumors, PDGFRA driven gastrointestinal stromal tumors, melanoma (e.g., cutaneous melanoma, noncutaneous melanoma, KIT driven melanoma or PGDFRA driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer, comprising administering to a patient in need thereof a therapeutically effective amount of a solid dispersion comprising a compound of Formula (I) and a pharmaceutically acceptable polymer, having a purity by HPLC of greater than about 95%. In some embodiments, the disease is caused by the kinase activity of: c-KIT and/or PDGFRA, and/or oncogenic forms thereof. In some embodiments, the disease is gastrointestinal stromal tumors (GIST). In some embodiments, the disease is KIT driven gastrointestinal stromal tumors. In some embodiments, the disease is PDGFRA driven gastrointestinal stromal tumors. In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, provided herein, is a method of treating or preventing a PDGFR kinase-mediated tumor growth of tumor progression comprising administering to a patient in need thereof a therapeutically effective amount of a solid dispersion comprising a compound of Formula (I) and a pharmaceutically acceptable polymer, having a purity by HPLC of greater than about 95%. In some embodiments, the tumor growth or tumor progression is caused by PDGFRα kinase overexpression, oncogenic PDGFRα missense mutations, oncogenic deletion PDGFRα mutations, oncogenic PDGFRα gene rearrangements leading to PDGFRα fusion proteins, PDGFRα intragenic in-frame deletions, and/or oncogenic PDGFRα gene amplification. In some embodiments, a solid dispersion comprising a compound of Formula (I) and a pharmaceutically acceptable polymer, having a purity by HPLC of greater than about 95% is administered to a cancer patient wherein the cancer is PDGFRA driven gastrointestinal stromal tumors, lung adenocarcinoma, squamous cell lung cancer, glioblastoma, glioma, pediatric glioma, astrocytomas, sarcomas, gastrointestinal stromal tumors, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, or lymphoblastic T-cell lymphoma. In some embodiments, the disease is PDGFRA driven gastrointestinal stromal tumors (GIST). In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, a solid dispersion comprising a compound of Formula (I) and a pharmaceutically acceptable polymer, having a purity by HPLC of greater than about 95% is administered as a single agent or in combination with other cancer targeted therapeutic agents, cancer-targeted biologicals, immune checkpoint inhibitors, or chemotherapeutic agents.

A compound of Formula (I), wherein the compound comprises one or more anilinic substances each present in an amount equal to or less than about 3.0% by weight based on the weight of the compound of Formula (I) as described herein is a broad-spectrum inhibitor of c-KIT. In some embodiments, provided herein is a method of treating a disease selected from the group consisting of gastrointestinal stromal tumors (GIST), KIT driven gastrointestinal stromal tumors, PDGFRA driven gastrointestinal stromal tumors, melanoma (e.g., cutaneous melanoma, noncutaneous melanoma, KIT driven melanoma or PGDFRA driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer, comprising administering to a patient in need thereof a therapeutically effective amount of a compound of Formula (I), wherein the compound comprises one or more anilinic substances each present in an amount equal to or less than about 3.0% by weight based on the weight of the compound of Formula (I). In some embodiments, the disease is caused by the kinase activity of: c-KIT and/or PDGFRA, and/or oncogenic forms thereof. In some embodiments, the disease is gastrointestinal stromal tumors (GIST). In some embodiments, the disease is KIT driven gastrointestinal stromal tumors. In some embodiments, the disease is PDGFRA driven gastrointestinal stromal tumors. In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, provided herein, is a method of treating or preventing a PDGFR kinase-mediated tumor growth of tumor progression comprising administering to a patient in need thereof a therapeutically effective amount of a compound of Formula (I), wherein the compound comprises one or more anilinic substances each present in an amount equal to or less than about 3.0% by weight based on the weight of the compound of Formula (I). In some embodiments, the tumor growth or tumor progression is caused by PDGFRα kinase overexpression, oncogenic PDGFRα missense mutations, oncogenic deletion PDGFRα mutations, oncogenic PDGFRα gene rearrangements leading to PDGFRα fusion proteins, PDGFRα intragenic in-frame deletions, and/or oncogenic PDGFRα gene amplification. In some embodiments, a compound of Formula (I), wherein the compound comprises one or more anilinic substances each present in an amount equal to or less than about 3.0% by weight based on the weight of the compound of Formula (I) is administered to a cancer patient wherein the cancer is PDGFRA driven gastrointestinal stromal tumors, lung adenocarcinoma, squamous cell lung cancer, glioblastoma, glioma, pediatric glioma, astrocytomas, sarcomas, gastrointestinal stromal tumors, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, or lymphoblastic T-cell lymphoma. In some embodiments, the disease is PDGFRA driven gastrointestinal stromal tumors (GIST). In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, a compound of Formula (I), wherein the compound comprises one or more anilinic substances each present in an amount equal to or less than about 3.0% by weight based on the weight of the compound of Formula (I) is administered as a single agent or in combination with other cancer targeted therapeutic agents, cancer-targeted biologicals, immune checkpoint inhibitors, or chemotherapeutic agents.

In some embodiments, a pharmaceutical composition comprising a compound of Formula (I) and one or more pharmaceutically acceptable carriers, excipients or diluents, wherein the pharmaceutical composition comprises one or more anilinic substances each present in an amount equal to or less than about 3.0% by weight based on the weight of the compound of Formula (I) as described herein is used in the preparation of a medicament for the treatment of a disease selected from the group consisting of gastrointestinal stromal tumors (GIST), KIT driven gastrointestinal stromal tumors, PDGFRA driven gastrointestinal stromal tumors, melanoma (e.g., cutaneous melanoma, noncutaneous melanoma, KIT driven melanoma or PGDFRA driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer. In some embodiments, the disease is caused by the kinase activity of: c-KIT and/or PDGFRA, and/or oncogenic forms thereof. In some embodiments, the disease is gastrointestinal stromal tumors (GIST). In some embodiments, the disease is KIT driven gastrointestinal stromal tumors. In some embodiments, the disease is PDGFRA driven gastrointestinal stromal tumors. In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, a pharmaceutical composition comprising a compound of Formula (I) and one or more pharmaceutically acceptable carriers, excipients or diluents, wherein the pharmaceutical composition comprises one or more anilinic substances each present in an amount equal to or less than about 3.0% by weight based on the weight of the compound of Formula (I) is used in the preparation of a medicament for treating or preventing a PDGFR kinase-mediated tumor growth of tumor. In some embodiments, the tumor growth or tumor progression is caused by PDGFRα kinase overexpression, oncogenic PDGFRα missense mutations, oncogenic deletion PDGFRα mutations, oncogenic PDGFRα gene rearrangements leading to PDGFRα fusion proteins, PDGFRα intragenic in-frame deletions, and/or oncogenic PDGFRα gene amplification. In some embodiments, a pharmaceutical composition comprising a compound of Formula (I) and one or more pharmaceutically acceptable carriers, excipients or diluents, wherein the pharmaceutical composition comprises one or more anilinic substances each present in an amount equal to or less than about 3.0% by weight based on the weight of the compound of Formula (I) is used in the preparation of a medicament for the treatment of a disease wherein the disease is PDGFRA driven gastrointestinal stromal tumors, lung adenocarcinoma, squamous cell lung cancer, glioblastoma, glioma, pediatric glioma, astrocytomas, sarcomas, gastrointestinal stromal tumors, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, or lymphoblastic T-cell lymphoma. In some embodiments, the disease is PDGFRA driven gastrointestinal stromal tumors (GIST). In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome.

In some embodiments, a solid dispersion comprising a compound of Formula (I) and a pharmaceutically acceptable polymer, wherein the solid dispersion comprises one or more anilinic substances each present in an amount equal to or less than about 3.0% by weight based on the weight of the compound of Formula (I) as described herein is used in the preparation of a medicament for the treatment of a disease selected from the group consisting of gastrointestinal stromal tumors (GIST), KIT driven gastrointestinal stromal tumors, PDGFRA driven gastrointestinal stromal tumors, melanoma (e.g., cutaneous melanoma, noncutaneous melanoma, KIT driven melanoma or PGDFRA driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer. In some embodiments, the disease is caused by the kinase activity of: c-KIT and/or PDGFRA, and/or oncogenic forms thereof. In some embodiments, the disease is gastrointestinal stromal tumors (GIST). In some embodiments, the disease is KIT driven gastrointestinal stromal tumors. In some embodiments, the disease is PDGFRA driven gastrointestinal stromal tumors. In some embodiments, the disease is lung cancer. In some embodiments, the disease is glioblastoma.

In some embodiments, the disease is a glioma. In some embodiments, the disease is malignant peripheral nerve sheath sarcoma. In some embodiments, the disease is a hypereosinophilic syndrome. In some embodiments, a solid dispersion comprising a compound of Formula (I) and a pharmaceutically acceptable polymer, wherein the solid dispersion comprises one or more anilinic substances each present in an amount equal to or less than about 3.0% by weight based on the weight of the compound of Formula (I) is used in the preparation of a medicament for treating or preventing a PDGFR kinase-mediated tumor growth of tumor. In some embodiments, the tumor growth or tumor progression is caused by PDGFRα kinase overexpression, oncogenic PDGFRα missense mutations, oncogenic deletion PDGFRα mutations, oncogenic PDGFRα gene rearrangements leading to PDGFRα fusion proteins, PDGFRα intragenic in-frame deletions, and/or oncogenic PDGFRα gene amplification. In some embodiments, a solid dispersion comprising a compound of Formula (I) and a pharmaceutically acceptable polymer, wherein the solid dispersion comprises one or more anilinic substances each present in an amount equal to or less than about 3.0% by weight based on the weight of the compound of Formula (I) is used in the preparation of a medicament for the treatment of a disease wherein the disease is PDGFRA driven gastrointestinal stromal tumors, lung adenocarcinoma, squamous cell lung cancer, glioblastoma, glioma, pediatric glioma, astrocytomas, sarcomas, gastrointestinal stromal tumors, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, or lymphoblastic T-cell lymphoma. In some embodiments, the disease is PDGFRA driven gastrointestinal stromal tumors (GIST). In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome.

In some embodiments, a solid dispersion comprising a compound of Formula (I) and a pharmaceutically acceptable polymer, having a purity by HPLC of greater than about 95% is used in the preparation of a medicament for the treatment of a disease selected from the group consisting of gastrointestinal stromal tumors (GIST), KIT driven gastrointestinal stromal tumors, PDGFRA driven gastrointestinal stromal tumors, melanoma (e.g., cutaneous melanoma, non-cutaneous melanoma, KIT driven melanoma or PGDFRA driven melanoma), acute myeloid leukemia, germ cell tumors of the seminoma or dysgerminoma, mastocytosis, mast cell leukemia, lung adenocarcinoma, squamous cell lung cancer, glioblastoma, glioma, pediatric glioma, astrocytomas, sarcomas, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, lymphoblastic T-cell lymphoma, and non-small cell lung cancer. In some embodiments, the disease is caused by the kinase activity of: c-KIT and/or PDGFRA, and/or oncogenic forms thereof. In some embodiments, the disease is gastrointestinal stromal tumors (GIST). In some embodiments, the disease is KIT driven gastrointestinal stromal tumors. In some embodiments, the disease is PDGFRA driven gastrointestinal stromal tumors. In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome. In some embodiments, a solid dispersion comprising a compound of Formula (I) and a pharmaceutically acceptable polymer, having a purity by HPLC of greater than about 95% is used in the preparation of a medicament for treating or preventing a PDGFR kinase-mediated tumor growth of tumor. In some embodiments, the tumor growth or tumor progression is caused by PDGFRα kinase overexpression, oncogenic PDGFRα missense mutations, oncogenic deletion PDGFRα mutations, oncogenic PDGFRα gene rearrangements leading to PDGFRα fusion proteins, PDGFRα intragenic in-frame deletions, and/or oncogenic PDGFRα gene amplification. In some embodiments, a solid dispersion comprising a compound of Formula (I) and a pharmaceutically acceptable polymer, having a purity by HPLC of greater than about 95% is used in the preparation of a medicament for the treatment of a disease wherein the disease is PDGFRA driven gastrointestinal stromal tumors, lung adenocarcinoma, squamous cell lung cancer, glioblastoma, glioma, pediatric glioma, astrocytomas, sarcomas, gastrointestinal stromal tumors, malignant peripheral nerve sheath sarcoma, intimal sarcomas, hypereosinophilic syndrome, idiopathic hypereosinophilic syndrome, chronic eosinophilic leukemia, eosinophilia-associated acute myeloid leukemia, or lymphoblastic T-cell lymphoma. In some embodiments, the disease is PDGFRA driven gastrointestinal stromal tumors (GIST). In some embodiments, the disease is lung cancer. In some embodiments, the disease is glioblastoma. In some embodiments, the disease is a glioma. In some embodiments, the disease is malignant peripheral nerve sheath sarcoma. In some embodiments, the disease is a hypereosinophilic syndrome.

In some embodiments, each anilinic substance is present in an amount equal to or less than about 5.0% by weight based on the weight of the compound of Formula (I). In some embodiments, each anilinic substance is present in an amount equal to or less than about 4.0% by weight based on the weight of the compound of Formula (I). In some embodiments, each anilinic substance is present in an amount equal to or less than about 2.0% by weight based on the weight of the compound of Formula (I). In some embodiments, each anilinic substance is present in an amount equal to or less than about 1.0% by weight based on the weight of the compound of Formula (I). In some embodiments, each anilinic substance is present in an amount equal to or less than about 0.7% by weight based on the weight of the compound of Formula (I). In some embodiments, each anilinic substance is present in an amount equal to or less than about 0.5% by weight based on the weight of the compound of Formula (I). In some embodiments, each anilinic substance is present in an amount equal to or less than about 0.3% by weight based on the weight of the compound of Formula (I).

In some embodiments, the diphenyl urea impurity is present in an amount equal to or less than about 0.30% by weight based on the weight of the compound of Formula (I) which means from about 0.0001% to a maximum of about 0.30%. In some embodiments, the diphenyl urea impurity is present in an amount equal to or less than about 0.20% by weight based on the weight of the compound of Formula (I) which means from about 0.0001% to a maximum of about 0.20%. In some embodiments, the diphenyl urea impurity is present in an amount equal to or less than about 0.10% by weight based on the weight of the compound of Formula (I) which means from about 0.0001% to a maximum of about 0.10%. In some embodiments, the diphenyl urea impurity is present in an amount equal to or less than about 0.075% by weight based on the weight of the compound of Formula (I) which means from about 0.0001% to a maximum of about 0.075%. In some embodiments, the diphenyl urea impurity is present in an amount equal to or less than about 0.05% by weight based on the weight of the compound of Formula (I) which means from about 0.0001% to a maximum of about 0.05%. In some embodiments, the diphenyl urea impurity is present in an amount equal to or less than about 0.04% by weight based on the weight of the compound of Formula (I) which means from about 0.0001% to a maximum of about 0.04%. In some embodiments, the diphenyl urea impurity is present in an amount equal to or less than about 0.03% by weight based on the weight of the compound of Formula (I) which means from about 0.0001% to a maximum of about 0.03%. In some embodiments, the diphenyl urea impurity is present in an amount equal to or less than about 0.02% by weight based on the weight of the compound of Formula (I) which means from about 0.0001% to a maximum of about 0.02%. In some embodiments, the diphenyl urea impurity is present in an amount equal to or less than about 0.01% by weight based on the weight of the compound of Formula (I) which means from about 0.0001% to a maximum of about 0.01%.

The pharmaceutical compositions described herein may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result is achieved.

Combination Therapy

The present disclosure describes combination therapies that involve the administration of the compound of Formula (I) or a pharmaceutically acceptable salt thereof, or a composition comprising the compound of Formula (I) or a pharmaceutically acceptable salt thereof described herein, and one or more therapeutic agents. The combination therapies described herein can be used by themselves, or in further combination with one or more additional therapeutic agents (e.g., one or more additional therapeutic agents described below). For example, the compound of Formula (I) or a pharmaceutically acceptable salt thereof, or a composition comprising the compound of Formula (I) or a pharmaceutically acceptable salt thereof described herein can be administered together with a cancer targeted therapeutic agent, a cancer-targeted biological, an immune checkpoint inhibitor, or a chemotherapeutic agent. The therapeutic agents can be administered together with or sequentially with another therapeutic agent described herein in a combination therapy.

Combination therapy can be achieved by administering two or more therapeutic agents, each of which is formulated and administered separately. In one embodiment, a composition comprising the compound of Formula (I) or a pharmaceutically acceptable salt thereof described herein is administered in a separate formulation than a formulation comprising the one or more additional therapeutic agents, e.g., one more additional therapeutic agents described herein. Alternatively, combination therapy can be achieved by administering two or more therapeutic agents in a single formulation.

Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc.

In some embodiments, the additional therapeutic agent that may be administered according to the present disclosure include, but are not limited to, cytotoxic agents, cisplatin, doxorubicin, etoposide, irinotecan, topotecan, paclitaxel, docetaxel, the epothilones, tamoxifen, 5-fluorouracil, methotrexate, temozolomide, cyclophosphamide, lonafarib, tipifarnib, 4-((5-((4-(3-chlorophenyl)-3-oxopiperazin-1-yl)methyl)-1H-imidazol-1-yl)methyl)benzonitrile hydrochloride, (R)-1-((1H-imidazol-5-yl)methyl)-3-benzyl-4-(thiophen-2-ylsulfonyl)-2,3,4,5-tetrahydro-1H-benzo diazepine-7-carbonitrile, cetuximab, imatinib, interferon alfa-2b, pegylated interferon alfa-2b, aromatase combinations, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, leucovorin, oxaliplatin, pentostatine, vinblastine, vincristine, vindesine, bleomycin, dactinomycin, daunorubicin, epirubicin, idarubicin, mithramycin, deoxycoformycin, mitomycin-C, L-asparaginase, teniposide 17α-ethinyl estradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, 17α-hydroxyprogesterone, aminoglutethimide, estramustine, medroxyprogesterone acetate, leuprolide acetate, flutamide, toremifene citrate, goserelin acetate, carboplatin, hydroxyurea, amsacrine, procarbazine, mitotane, mitoxantrone, levamisole, vinorelbine, anastrazole, letrozole, capecitabine, raloxifene, droloxafine, hexamethylmelamine, bevacizumab, trastuzumab, tositumomab, bortezomib, ibritumomab tiuxetan, arsenic trioxide, porfimer sodium, cetuximab, thio-TEPA, altretamine, fulvestrant, exemestane, rituximab, alemtuzumab, dexamethasone, bicalutamide, chlorambucil, and valrubicin.

In some embodiments, the additional therapeutic agent that can be administered may include, without limitation, an AKT inhibitor, alkylating agent, all-trans retinoic acid, anti-androgen, azacitidine, BCL2 inhibitor, BCL-XL inhibitor, BCR-ABL inhibitor, BTK inhibitor, BTK/LCK/LYN inhibitor, CDK1/2/4/6/7/9 inhibitor, CDK4/6 inhibitor, CDK9 inhibitor, CBP/p300 inhibitor, EGFR inhibitor, endothelin receptor antagonist, RAF inhibitor, MEK inhibitor, ERK inhibitor, farnesyltransferase inhibitor, FLT3 inhibitor, glucocorticoid receptor agonist, HDM2 inhibitor, histone deacetylase inhibitor, IKKO inhibitor, immunomodulatory drug (IMiD), ingenol, ITK inhibitor, JAK1/JAK2/JAK3/TYK2 inhibitor, MTOR inhibitor, PI3 kinase inhibitor, dual PI3 kinase/MTOR inhibitor, proteasome inhibitor, protein kinase C agonist, SUV39H1 inhibitor, TRAIL, VEGFR2 inhibitor, Wnt/0-catenin signaling inhibitor, decitabine, and anti-CD20 monoclonal antibody.

In some embodiments, the additional therapeutic agent is an immunomodulatory agent selected from the group consisting of CTLA4 inhibitors such as, but not limited to ipilimumab and tremelimumab; PD1 inhibitors such as, but not limited to pembrolizumab, and nivolumab; PDL1 inhibitors such as, but not limited to atezolizumab (formerly MPDL3280A), durvalumab (formerly MEDI4736), avelumab, PDR001; 4 1BB or 4 1BB ligand inhibitors such as, but not limited to urelumab and PF-05082566; OX40 ligand agonists such as, but not limited to MEDI6469; GITR agents such as, but not limited to TRX518; CD27 inhibitors such as, but not limited to varlilumab; TNFRSF25 or TL1A inhibitors; CD40 agonists such as, but not limited to CP-870893; HVEM or LIGHT or LTA or BTLA or CD160 inhibitors; LAG3 inhibitors such as, but not limited to BMS-986016; TIM3 inhibitors; Siglecs inhibitors; ICOS or ICOS ligand agonists; B7 H3 inhibitors such as, but not limited to MGA271; B7 H4 inhibitors; VISTA inhibitors; HHLA2 or TMIGD2 inhibitors; inhibitors of Butyrophilins, including BTNL2 inhibitors; CD244 or CD48 inhibitors; inhibitors of TIGIT and PVR family members; KIRs inhibitors such as, but not limited to lirilumab; inhibitors of ILTs and LIRs; NKG2D and NKG2A inhibitors such as, but not limited to IPH2201; inhibitors of MICA and MICB; CD244 inhibitors; CSF1R inhibitors such as, but not limited to emactuzumab, cabiralizumab, pexidartinib, ARRY382, BLZ945; IDO inhibitors such as, but not limited to INCB024360; thalidomide, lenalidomide, TGFβ inhibitors such as, but not limited to galunisertib; adenosine or CD39 or CD73 inhibitors; CXCR4 or CXCL12 inhibitors such as, but not limited to ulocuplumab and (3S,6S,9S,12R,17R,20S,23S,26S,29S,34aS)-N-((S)-1-amino-5-guanidino-1-oxopentan-2-yl)-26,29-bis(4-aminobutyl)-17-((S)-2-((S)-2-((S)-2-(4-fluorobenzamido)-5-guanidinopentanamido)-5-guanidinopentanamido)-3-(naphthalen-2-yl)propanamido)-6-(3-guanidinopropyl)-3,20-bis(4-hydroxybenzyl)-1,4,7,10,18,21,24,27,30-nonaoxo-9,23-bis(3-ureidopropyl)triacontahydro-1H,16H-pyrrolo[2,1-p][1,2]dithia[5,8,11,14,17,20,23,26,29]nonaazacyclodotriacontine-12-carboxamide BKT140; phosphatidylserine inhibitors such as, but not limited to bavituximab; SIRPA or CD47 inhibitors such as, but not limited to CC-90002; VEGF inhibitors such as, but not limited to bevacizumab; and neuropilin inhibitors such as, but not limited to MNRP1685A.

In some embodiments, the additional therapeutic agent is a chemotherapeutic agent selected from the group consisting of chemotherapeutic agents including but not limited to anti-tubulin agents (paclitaxel, paclitaxel protein-bound particles for injectable suspension such as nab-paclitaxel, eribulin, docetaxel, ixabepilone, vincristine), vinorelbine, DNA-alkylating agents (including cisplatin, carboplatin, oxaliplatin, cyclophosphamide, ifosfamide, temozolomide), DNA intercalating agents (including doxorubicin, pegylated liposomal doxorubicin, daunorubicin, idarubicin, and epirubicin), 5-fluorouracil, capecitabine, cytarabine, decitabine, 5-aza cytadine, gemcitabine and methotrexate.

In some embodiments, the additional therapeutic agent is selected from the group consisting of paclitaxel, paclitaxel protein-bound particles for injectable suspension, eribulin, docetaxel, ixabepilone, vincristine, vinorelbine, cisplatin, carboplatin, oxaliplatin, cyclophosphamide, ifosfamide, temozolomide, doxorubicin, pegylated liposomal doxorubicin, daunorubicin, idarubicin, epirubicin, 5-fluorouracil, capecitabine, cytarabine, decitabine, 5-azacytadine, gemcitabine, methotrexate, erlotinib, gefitinib, lapatinib, everolimus, temsirolimus, LY2835219, LEE011, PD 0332991, crizotinib, cabozantinib, sunitinib, pazopanib, sorafenib, regorafenib, axitinib, dasatinib, imatinib, nilotinib, vemurafenib, dabrafenib, trametinib, idelasib, quizartinib, tamoxifen, fulvestrant, anastrozole, letrozole, exemestane, abiraterone acetate, enzalutamide, nilutamide, bicalutamide, flutamide, cyproterone acetate, prednisone, dexamethasone, irinotecan, camptothecin, topotecan, etoposide, etoposide phosphate, mitoxantrone, vorinostat, romidepsin, panobinostat, valproic acid, belinostat, DZNep 5-aza-2'-deoxycytidine, bortezomib, carfilzomib, thalidomide, lenalidomide, pomalidomide, trastuzumab, pertuzumab, cetuximab, panitumumab, ipilimumab, labrolizumab, nivolumab, MPDL3280A, bevacizumab, aflibercept, brentuximab vedotin, ado-trastuzumab emtansine, radiotherapy, and sipuleucel T.

In some embodiments, the additional therapeutic agent is a kinase inhibitor selected from the group consisting of erlotinib, gefitinib, lapatanib, everolimus, temsirolimus, LY2835219, LEE011, PD 0332991, crizotinib, cabozantinib, sunitinib, pazopanib, sorafenib, regorafenib, axitinib, dasatinib, imatinib, nilotinib, vemurafenib, dabrafenib, trametinib, idelalisib, and quizartinib.

In some embodiments, the additional therapeutic agent is an anti-PD1 therapeutic. Examples of anti-PD1 therapeutics that may be administered in combination with the compound of Formula (I) or pharmaceutically acceptable salt thereof or a composition comprising the compound of Formula (I) or pharmaceutically acceptable salt thereof described herein include, but are not limited to, nivolumab, pidilizumab, cemiplimab, tislelizumab, AMP-224, AMP-514, and pembrolizumab.

In some embodiments, the additional therapeutic agent is selected from the group consisting of immunomodulatory agents including but not limited to anti-PD-L1 therapeutics including atezolizumab, durvalumab, BMS-936559, and avelumab, anti-TIM3 therapeutics including TSR-022 and MBG453, anti-LAG3 therapeutics including relatlimab, LAG525, and TSR-033, CD40 agonist therapeutics including SGN-40, CP-870,893 and R07009789, anti-CD47 therapeutics including Hu5F9-G4, anti-CD20 therapeutics, anti-CD38 therapeutics, and other immunomodulatory therapeutics including thalidomide, lenalidomide, pomalidomide, prednisone, and dexamethasone. In some embodiments, the additional therapeutic agent is avelumab.

In some embodiments, the additional therapeutic agent is a chemotherapeutic agent selected from the group consisting of anti-tubulin agents (e.g., paclitaxel, paclitaxel protein-bound particles for injectable suspension, eribulin, abraxane, docetaxel, ixabepilone, taxiterem, vincristine or vinorelbine), LHRH antagonists including but not limited to leuprolide, goserelin, triptorelin, or histrelin, anti-androgen agents including but not limited to abiraterone, flutamide, bicalutamide, nilutamide, cyproterone acetate, enzalutamide, and apalutamide, anti-estrogen agents including but not limited to tamoxifen, fulvestrant, anastrozole, letrozole, and exemestane, DNA-alkylating agents (including cisplatin, carboplatin, oxaliplatin, cyclophosphamide, ifosfamide, and temozolomide), DNA intercalating agents (including doxorubicin, pegylated liposomal doxorubicin, daunorubicin, idarubicin, and epirubicin), 5-fluorouracil, capecitabine, cytarabine, decitabine, 5-aza cytadine, gemcitabine methotrexate, bortezomib, and carfilzomib.

In some embodiments, the additional therapeutic agent is selected from the group consisting of targeted therapeutics including kinase inhibitors erlotinib, gefitinib, lapatanib, everolimus, temsirolimus, abemaciclib, LEE011, palbociclib, crizotinib, cabozantinib, sunitinib, pazopanib, sorafenib, regorafenib, axitinib, dasatinib, imatinib, nilotinib, vemurafenib, dabrafenib, trametinib, cobimetinib, binimetinib, idelalisib, quizartinib, avapritinib, BLU-667, BLU-263, Loxo 292, larotrectinib, and quizartinib, anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, and rucaparib, topoisomerase I inhibitors including but not limited to irinotecan, camptothecin, and topotecan, topoisomerase II inhibitors including but not limited to etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNep and 5-aza-2'-deoxycytidine, proteasome inhibitors including but not limited to bortezomib and carfilzomib, thalidomide, lenalidomide, pomalidomide, biological agents including but not limited to trastuzumab, ado-trastuzumab, pertuzumab, cetuximab, panitumumab, ipilimumab, tremelimumab, vaccines including but not limited to sipuleucel-T, and radiotherapy.

In some embodiments, the additional therapeutic agent is selected from the group consisting of an inhibitor of the TIE2 immunokinase including rebastinib or ARRY-614.

In some embodiments, the additional therapeutic agent is selected from the group consisting of an inhibitor of the TIE2 immunokinase including rebastinib or ARRY-614, and an anti-PD1 therapeutic.

In some embodiments, the additional therapeutic agent is selected from the group consisting of anti-angiogenic agents including AMG386, bevacizumab and aflibercept, and antibody-drug-conjugates (ADCs) including brentuximab vedotin, trastuzumab emtansine, and ADCs containing a payload such as a derivative of camptothecin, a pyrrolobenzodiazepine dimer (PBD), an indolinobenzodiazepine dimer (IGN), DM1, DM4, MMAE, or MMAF.

In some embodiments, the additional therapeutic agent is selected from a luteinizing hormone-releasing hormone (LHRH) analog, including goserelin and leuprolide. In some embodiments, the additional therapeutic agent is selected from the group consisting of selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatinib, nilotinib, decatanib, panitumumab, amrubicin, oregovomab, Lep-etu, nolatrexed, azd2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, ipilumumab, vemurafenib, and mixtures thereof.

In some embodiments, the additional therapeutic agent is an HSP90 inhibitor (e.g., AT13387). In some embodiments, the additional therapeutic agent is cyclophosphamide. In some embodiments, the additional therapeutic agent is an AKT inhibitor (e.g., perifosine). In some embodiments, the additional therapeutic agent is a BCR-ABL inhibitor (e.g., nilotinib). In some embodiments, the additional therapeutic agent is an mTOR inhibitor (e.g., RAD001). In some embodiments, the additional therapeutic agent is an FGFR inhibitor (e.g., erdafitinib, K0947, or BGJ398). In some embodiments, the additional therapeutic agent is an anti-PDL1 therapeutic. In some embodiments, the additional therapeutic agent is a Bcl2 inhibitor (e.g., venetoclax). In some embodiments, the additional therapeutic agent is an autophagy inhibitor (e.g., hydroxychloroquine). In some embodiments, the additional therapeutic agent is a MET inhibitor.

EXAMPLES

The present disclosure is not to be limited in scope by the specific embodiments disclosed in the examples which are intended as illustrations of a few aspects of the disclosure and any embodiments that are functionally equivalent are within the scope of this disclosure. Indeed, various modifications in addition to those shown and described herein will become apparent to those skilled in the art and are intended to fall within the scope of the appended claims.

In the Examples provided below, the following abbreviations are used: "HPMCAS-HG" refers to hydroxymethylpropyl cellulose acetate succinate (high PH solubility grade); "SDD" refers to spray-dried dispersion; and "PVP-XL" refers to cross-linked polyvinylpyrrolidone. "Compound 1" refers to the compound of Formula (I) described herein. "Compound 2" refers to the compound 3-(5-amino-2-bromo-4-fluorophenyl)-1-ethyl-7-(methylamino)-1,6-naphthyridin-2(1H)-one, which has the structure:

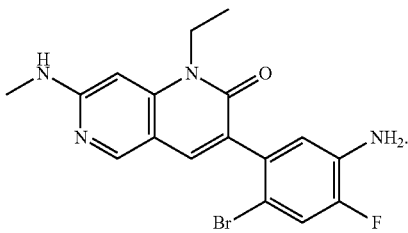 [SMILES: CCn1c(=O)c(-c2cc(N)c(F)cc2Br)cc2cnc(NC)cc21]

Unless otherwise stated, percentages amounts of the compound of Formula (I) in the solid dispersions described below indicate weight percentages of the compound of Formula (I) with respect to the total weight of the solid dispersion.

As used below in Example 1, the "w/w suspension fraction" is the fraction of a component, as a weight percentage, of the suspension used to prepare the spray-dried dispersion based on the amount of Compound 1 in the suspension.

Example 1. Preparation of a Spray-Dried Dispersion Comprising Compound 1 and HPMCAS-HG Suspension preparation. HPMCAS-HG is added to a purified water and acetone solution and mixed to ensure dissolution of the polymer. Compound 1 is added to the solution, and the suspension is mixed at a temperature of 15-25° C. The mixing remains on for the remainder of spray drying process.

Startup/shutdown solvent preparation and use. Purified water and acetone are mixed. The startup and shutdown solvent are sprayed at the beginning and end of the spray drying cycle.

Spray Drying. The suspension is passed through an inline heat exchanger (flow rate of 38-51 kg/hr) which heats the suspension to a temperature range of 112-124° C. to dissolve the suspended particles prior to spray drying. The solution is then spray dried in a pharmaceutical spray dryer (PSD-2 or equivalent) equipped with a capillary nozzle assisted with nitrogen sheath gas pressure of 65-85 psig using 400-500 kg/hr bulk drying gas, 50-70° C. chamber outlet temperature and −10° C. condenser temperature.

Secondary drying. The partially wet spray-dried intermediate resulting from the preparation described above is dried to provide an SDD comprising Compound 1 and HPMCAS-HG using agitated vacuum dryer at temperature range of 40-50° C. and chamber pressure of 40-50 mbar.

Analytical Method for Determining Amount of Impurities in Compound of Formula (I) (Compound 1).

| Equipment, Reagents, and Impurity Marker Solutions | |
|---|---|
| Equipment | |
| HPLC system | Suitable RP-HPLC equipped with a photodiode array UV detector and data system. |
| Column | Zorbax Bonus RP, 4.6 × 150 mm, 3.5 µm (Agilent) equipped with HPLC column filter (0.5 µm), or equivalent |

| HPLC Instrument Parameters for Identification, Assay, Degradation Products, and Uniformity of Dosage Units | | |
|---|---|---|
| Parameter | Value | |
| Column temperature | 40° C. | |
| Autosampler temperature | 20° C. | |
| Flow rate | 1.0 mL/min | |
| Injection volume | 3 µL | |
| Detection | UV at 240 nm Spectra collection 200-400 nm | |
| Acquisition run time | 20 minutes | |
| Mobile phase | Mobile Phase A: purified water Mobile Phase B: acetonitrile | |
| Seal and needle wash | THF:HPLC-grade water:FA, 75:25:0.1 (v/v/v) | |
| Diluent | THF:purified water:FA, 75:25:0.1 (v/v/v) | |
| Gradient | Minutes | % Mobile Phase A | % Mobile Phase B |
| | 0 | 80 | 20 |
| | 6.0 | 20 | 80 |
| | 16.0 | 0 | 100 |
| | 16.1 | 80 | 20 |
| | 20.0 | 80 | 20 |
| Post analysis column wash | Post analysis column wash shall be performed in accordance with testing site procedure | |

Abbreviations: FA: formic acid; THF: tetrahydrofuran; UV: ultraviolet; v: volume.

| Attribute | Impurities | Lot 1 made by the process of example 1 | Lot 2 made by the process of example 1 | Lot 3 made by the process of example 1 | Lot 4 made by the process of example 1 |
|---|---|---|---|---|---|
| Related Substances (% w/w with respect to the weight of Compound 1) | Impurity A | 0.14% | 0.13% | 0.16% | 0.15% |
| | Impurity B | <0.05% | <0.05% | <0.05% | <0.05% |
| | Diphenyl urea | <0.05% | <0.05% | <0.05% | <0.05% |

Example 2. Preparation of a Spray-Dried Dispersion Comprising Compound 1 and HPMCAS-HG Solution preparation. Compound 1 is added to a purified water and THF solution and mixed to ensure dissolution of the compound. HPMCAS-HG is added to the solution and mixed at ambient temperature until the polymer dissolves. Startup/shutdown solvent preparation and use. Purified water and THF are mixed. The startup and shutdown solvent are sprayed at the beginning and end of the spray drying cycle.

Spray Drying. The solution is then spray dried in a pharmaceutical spray dryer at 175-205 g/min spray rate using 1550-2150 g/min bulk drying gas flow rate and 40-50° C. chamber outlet temperature.

Secondary drying. The partially wet spray-dried intermediate resulting from the preparation described above is dried to provide an SDD comprising Compound 1 and HPMCAS-HG using tray dryer at temperature range of 15-45° C.

Example 3. Purity Studies of a Solid Dispersion of the Compound of Formula (I)

Purity studies on samples (Lot 1, Lot 2, Lot 3, and Lot 4) of a solid dispersion of the compound of Formula (I) were conducted using HPLC. Each lot was prepared according to the process outlined in Example 1. Results of the study are shown in Table 1 below.

TABLE 1

Purity by HPLC for a solid dispersion of the compound of Formula (I).

| Lot Number | Lot 1 | Lot 2 | Lot 3 | Lot 4 |
|---|---|---|---|---|
| Appearance | White powder | White powder | White powder | White powder |
| Identification (HPLC) | Rep 1: 100.0% | Rep 1: 100.0% | Rep 1: 100.0% | Rep 1: 100.0% |
| | Rep 2: 99.9% | Rep 2: 100.0% | Rep 2: 100.0% | Rep 2: 100.0% |
| Compound 1 Assay (% w/w) | 24.8 | 24.9 | 24.9 | 24.9 |
| Compound 2 (% w/w with respect to the weight of Compound 1) | 0.14 | 0.13 | 0.13 | 0.13 |

Legend: LOD: Levels of Detection Solid Dispersions.

Example 4. Preparation of Compound of Formula (III) Reference Standard 3-(5-amino-2-bromo-4-fluorophenyl)-1-ethyl-7-(methylamino)-1,6-naphthyridin-2(1H)-one (40 g), phenyl isocyanate (30 g, 2.7 equiv.), pyridine (3 eq) and methanesulfonic acid (1 eq) were combined in a solvent comprised of 1-methyl-2-pyrrolidinone (10 vol) and tetrahydrofuran (5 vol). The mixture was stirred at 50° C. for 7 days with occasional addition of additional 0.1-0.2 eq of phenyl isocyanate (0.1-0.2 eq) to obtain crude 1-(3-(2-bromo-4-fluoro-5-(3-phenylureido)phenyl)-1-ethyl-2-oxo-1,2-dihydro-1,6-naphthyridin-7-yl)-1-methyl-3-phenylurea wet cake. The crude wetcake was crystallized from 1-methyl-2-pyrrolidi- none (4 vol) and methanol (8 vol) to obtain 57 g of 1-(3-(2-bromo-4-fluoro-5-(3-phenylureido)phenyl)-1-ethyl-2-oxo-1,2-dihydro-1,6-naphthyridin-7-yl)-1-methyl-3-phenylurea. MS m/z: 629 (M+1). $^1$H NMR (400 MHz, DMSO-d$_6$): δ 11.44 (s, 1H), 9.12 (s, 1H), 8.84 (s, 1H), 8.74 (s, 1H), 8.29 and 8.27 (d, 1H), 8.02 (s, 1H), 7.72 and 7.70 (d, 1H), 7.59 and 7.57 (d, 2H), 7.45 and 7.43 (d, 2H), 7.34-7.26 (m, 4H), 7.24 (s, 1H), 7.06-6.97 (m, 2H), 4.35-4.28 (m, 2H), 3.53 (s, 3H), 1.27-1.23 (t, 3H).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A pharmaceutical composition for orally delivering a compound represented by Formula (I):

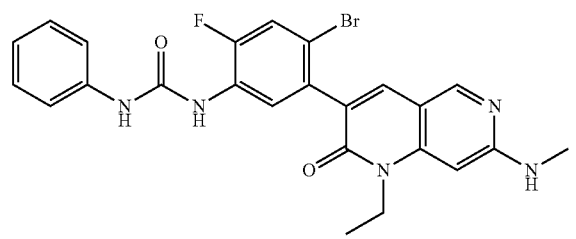

Formula (I)

the pharmaceutical composition comprising:
a solid dispersion comprising:
(a) 50 mg of the compound wherein the compound is present in amorphous form; and
(b) hydroxypropyl methyl cellulose acetate succinate;
wherein diphenyl urea is present in the pharmaceutical composition in amount equal to or less than about 10% by weight based on the total weight of the pharmaceutical composition.

2. The pharmaceutical composition of claim 1, wherein diphenyl urea is present in the pharmaceutical composition in amount equal to or less than about 3% by weight based on the total weight of the pharmaceutical composition.

3. The pharmaceutical composition of claim 1, wherein diphenyl urea is present in the pharmaceutical composition in amount equal to or less than about 1% by weight based on the total weight of the pharmaceutical composition.

4. The pharmaceutical composition of claim 1, wherein diphenyl urea is present in the pharmaceutical composition in amount equal to or less than about 0.5% by weight based on the total weight of the pharmaceutical composition.

5. A pharmaceutical composition for oral delivery, comprising:
a solid dispersion comprising:
(a) an amorphous form of a compound represented by Formula (I):

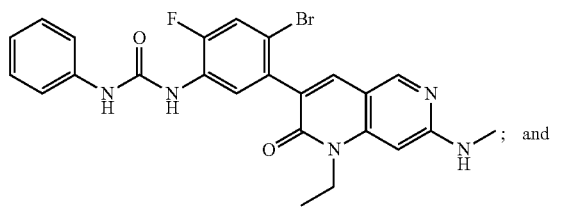

Formula (I)

; and (b) hydroxypropyl methyl cellulose acetate succinate;
wherein diphenyl urea is present in the pharmaceutical composition in amount equal to or less than about 10% by weight based on the total weight of the pharmaceutical composition.

6. The pharmaceutical composition of claim 5, wherein diphenyl urea is present in the pharmaceutical composition in amount equal to or less than about 3% by weight based on the total weight of the pharmaceutical composition.

7. The pharmaceutical composition of claim 5, wherein diphenyl urea is present in the pharmaceutical composition in amount equal to or less than about 1% by weight based on the total weight of the pharmaceutical composition.

8. The pharmaceutical composition of claim 5, wherein diphenyl urea is present in the pharmaceutical composition in amount equal to or less than about 0.5% by weight based on the total weight of the pharmaceutical composition.

9. A pharmaceutical composition for oral delivery, comprising:
a solid dispersion and one or more pharmaceutically acceptable carriers, wherein the solid dispersion comprises:
(a) an amorphous form of a compound represented by Formula (I):

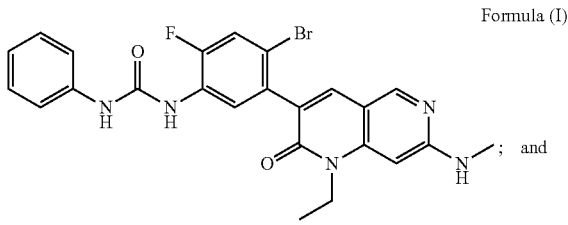 [SMILES: CCn1c(=O)c(-c2cc(NC(=O)Nc3ccccc3)c(F)cc2Br)cc2cnc(NC)cc21]

Formula (I)

; and (b) hydroxypropyl methyl cellulose acetate succinate;
wherein diphenyl urea is present in the pharmaceutical composition in amount equal to or less than about 10% by weight based on the total weight of the pharmaceutical composition.

10. The pharmaceutical composition of claim 9, wherein diphenyl urea is present in the pharmaceutical composition in amount equal to or less than about 3% by weight based on the total weight of the pharmaceutical composition.

11. The pharmaceutical composition of claim 9, wherein diphenyl urea is present in the pharmaceutical composition in amount equal to or less than about 1% by weight based on the total weight of the pharmaceutical composition.

12. The pharmaceutical composition of claim 9, wherein diphenyl urea is present in the pharmaceutical composition in amount equal to or less than about 0.5% by weight based on the total weight of the pharmaceutical composition.

* * * * *